United States Patent
Miller et al.

(10) Patent No.: US 9,017,323 B2
(45) Date of Patent: Apr. 28, 2015

(54) DEVICES AND METHODS FOR FORMING A FISTULA

(75) Inventors: Gary H. Miller, Milpitas, CA (US);
Adam L. Berman, Austin, TX (US);
William E. Cohn, Bellaire, TX (US);
Dana R. Mester, Austin, TX (US);
Damian A. Jelich, Austin, TX (US)

(73) Assignee: TVA Medical, Inc., Austin, TX (US)

( * ) Notice: Subject to any disclaimer, the term of this patent is extended or adjusted under 35 U.S.C. 154(b) by 724 days.

(21) Appl. No.: 13/298,169

(22) Filed: Nov. 16, 2011

(65) Prior Publication Data
US 2012/0302935 A1    Nov. 29, 2012

Related U.S. Application Data

(60) Provisional application No. 61/414,357, filed on Nov. 16, 2010.

(51) Int. Cl.
*A61B 18/00* (2006.01)
*A61M 1/36* (2006.01)
*A61B 17/3207* (2006.01)
*A61B 18/14* (2006.01)
*A61B 17/00* (2006.01)
*A61B 19/00* (2006.01)

(52) U.S. Cl.
CPC ...... *A61M 1/3655* (2013.01); *A61B 17/320725* (2013.01); *A61B 18/1492* (2013.01); *A61B 2017/00778* (2013.01); *A61B 2017/00876* (2013.01); *A61B 2017/320791* (2013.01); *A61B 2018/00083* (2013.01); *A61B 2018/00107* (2013.01); *A61B 2018/00577* (2013.01); *A61B 2018/144* (2013.01); *A61B 2019/5425* (2013.01); *A61B 2019/5466* (2013.01)

(58) Field of Classification Search
None
See application file for complete search history.

(56) References Cited

U.S. PATENT DOCUMENTS

| 5,830,222 A | 11/1998 | Makower |
| 5,830,224 A | 11/1998 | Cohn et al. |
| 6,004,330 A | 12/1999 | Middleman et al. |

(Continued)

FOREIGN PATENT DOCUMENTS

| EP | 0889705 A1 | 1/1999 |
| JP | 3493464 B2 | 2/2004 |

(Continued)

OTHER PUBLICATIONS

International Preliminary Report on Patentability received for PCT Patent Application No. PCT/US2011/061026, mailed on May 30, 2013, 8 pages.

(Continued)

*Primary Examiner* — Brian T Gedeon
*Assistant Examiner* — Ankit Tejani
(74) *Attorney, Agent, or Firm* — Morrison & Foerster LLP

(57) ABSTRACT

Described here are devices, systems and methods for forming a fistula between two blood vessels. Generally, the systems may comprise a first catheter which may comprise a fistula-forming element. The fistula-forming element may comprise one or more electrodes, mechanical cutting elements, laser sources, or combinations thereof, and may be used to assist in fistula formation. In some instances, a system may comprise a second catheter, which may comprise a fistula-forming element. One or more of the catheters may comprise one or more markers, magnetic alignment elements, and/or one shape-changing elements.

24 Claims, 71 Drawing Sheets

(56) References Cited

U.S. PATENT DOCUMENTS

| | | | |
|---|---|---|---|
| 6,032,677 A | 3/2000 | Blechman et al. | |
| 6,099,542 A | 8/2000 | Cohn et al. | |
| 6,217,575 B1 | 4/2001 | DeVore et al. | |
| 6,256,525 B1 | 7/2001 | Yang et al. | |
| 6,287,306 B1 | 9/2001 | Kroll et al. | |
| 6,302,875 B1 | 10/2001 | Makower et al. | |
| 6,357,447 B1 | 3/2002 | Swanson et al. | |
| 6,379,353 B1 * | 4/2002 | Nichols | 606/41 |
| 6,400,976 B1 | 6/2002 | Champeau | |
| 6,461,356 B1 | 10/2002 | Patterson | |
| 6,464,665 B1 | 10/2002 | Heuser | |
| 6,475,214 B1 | 11/2002 | Moaddeb | |
| 6,527,769 B2 | 3/2003 | Langberg et al. | |
| 6,542,766 B2 | 4/2003 | Hall et al. | |
| 6,569,162 B2 | 5/2003 | He | |
| 6,656,173 B1 | 12/2003 | Palermo | |
| 6,663,625 B1 | 12/2003 | Ormsby et al. | |
| 6,669,709 B1 | 12/2003 | Cohn et al. | |
| 6,676,657 B2 | 1/2004 | Wood | |
| 6,719,756 B1 | 4/2004 | Muntermann | |
| 6,780,181 B2 | 8/2004 | Kroll et al. | |
| 6,849,073 B2 | 2/2005 | Hoey et al. | |
| 6,855,143 B2 | 2/2005 | Davison et al. | |
| 6,911,026 B1 | 6/2005 | Hall et al. | |
| 6,932,814 B2 | 8/2005 | Wood | |
| 6,960,209 B2 | 11/2005 | Clague et al. | |
| 6,971,983 B1 | 12/2005 | Cancio | |
| 7,060,063 B2 | 6/2006 | Marion et al. | |
| 7,155,293 B2 | 12/2006 | Westlund et al. | |
| 7,189,231 B2 | 3/2007 | Clague et al. | |
| 7,231,260 B2 | 6/2007 | Wallace et al. | |
| 7,288,075 B2 | 10/2007 | Parihar et al. | |
| 7,306,598 B2 | 12/2007 | Truckai et al. | |
| 7,341,063 B2 | 3/2008 | Garbibaldi et al. | |
| 7,387,636 B2 | 6/2008 | Cohn et al. | |
| 7,628,768 B2 | 12/2009 | Faul et al. | |
| 7,702,387 B2 | 4/2010 | Stevenson et al. | |
| 7,744,596 B2 | 6/2010 | Young et al. | |
| 7,811,281 B1 | 10/2010 | Rentrop | |
| 7,828,814 B2 | 11/2010 | Brenneman et al. | |
| 7,846,172 B2 | 12/2010 | Makower | |
| 7,857,809 B2 | 12/2010 | Drysen | |
| 7,881,797 B2 * | 2/2011 | Griffin et al. | 607/40 |
| 7,955,326 B2 | 6/2011 | Paul et al. | |
| 7,967,769 B2 | 6/2011 | Faul et al. | |
| 8,010,208 B2 | 8/2011 | Nimer et al. | |
| 8,048,016 B2 | 11/2011 | Faul et al. | |
| 8,052,680 B2 | 11/2011 | Hassett et al. | |
| 8,062,321 B2 | 11/2011 | Heuser et al. | |
| 8,075,555 B2 | 12/2011 | Truckai et al. | |
| 8,088,171 B2 | 1/2012 | Brenneman | |
| 8,100,899 B2 | 1/2012 | Doty et al. | |
| 8,118,809 B2 | 2/2012 | Paul et al. | |
| 8,135,467 B2 | 3/2012 | Markowitz et al. | |
| 8,192,425 B2 | 6/2012 | Mirza et al. | |
| 8,226,592 B2 | 7/2012 | Brenneman et al. | |
| 8,231,618 B2 | 7/2012 | Viswanathan et al. | |
| 8,236,014 B2 | 8/2012 | Brenneman et al. | |
| 8,273,095 B2 | 9/2012 | Brenneman et al. | |
| 8,409,196 B2 | 4/2013 | Durgin et al. | |
| 8,414,572 B2 | 4/2013 | Davison et al. | |
| 8,439,909 B2 | 5/2013 | Wang et al. | |
| 8,486,064 B2 | 7/2013 | Van Wyk et al. | |
| 8,649,879 B2 | 2/2014 | DiGiore et al. | |
| 8,700,179 B2 | 4/2014 | Pianca et al. | |
| 8,790,341 B2 | 7/2014 | Pappone et al. | |
| 2004/0236360 A1 | 11/2004 | Cohn et al. | |
| 2005/0033401 A1 | 2/2005 | Cunniffe et al. | |
| 2006/0079897 A1 | 4/2006 | Harrison et al. | |
| 2006/0111704 A1 * | 5/2006 | Brenneman et al. | 606/41 |
| 2008/0065019 A1 | 3/2008 | Heuser et al. | |
| 2008/0091192 A1 | 4/2008 | Paul et al. | |
| 2008/0119879 A1 | 5/2008 | Brenneman et al. | |
| 2009/0076324 A1 | 3/2009 | Takayama et al. | |
| 2009/0112119 A1 | 4/2009 | Kim | |
| 2009/0275876 A1 | 11/2009 | Brenneman et al. | |
| 2010/0004623 A1 | 1/2010 | Hamilton, Jr. et al. | |
| 2010/0010488 A1 | 1/2010 | Kassab et al. | |
| 2010/0130835 A1 | 5/2010 | Brenneman et al. | |
| 2010/0204691 A1 | 8/2010 | Bencini | |
| 2010/0222664 A1 | 9/2010 | Lemon et al. | |
| 2010/0256616 A1 | 10/2010 | Katoh et al. | |
| 2010/0292685 A1 | 11/2010 | Katoh et al. | |
| 2011/0015657 A1 | 1/2011 | Brenneman et al. | |
| 2011/0112427 A1 | 5/2011 | Phillips et al. | |
| 2011/0118735 A1 | 5/2011 | Abou-Marie et al. | |
| 2011/0201990 A1 | 8/2011 | Franano | |
| 2011/0270149 A1 | 11/2011 | Faul et al. | |
| 2011/0288392 A1 | 11/2011 | de la Rama et al. | |
| 2012/0010556 A1 | 1/2012 | Faul et al. | |
| 2012/0035539 A1 | 2/2012 | Tegg | |
| 2012/0059398 A1 | 3/2012 | Pate et al. | |
| 2012/0089123 A1 | 4/2012 | Organ et al. | |
| 2012/0101423 A1 | 4/2012 | Brenneman | |
| 2012/0116354 A1 | 5/2012 | Heuser | |
| 2012/0157992 A1 | 6/2012 | Smith et al. | |
| 2012/0281330 A1 | 11/2012 | Abbott et al. | |
| 2012/0302935 A1 | 11/2012 | Miller et al. | |
| 2013/0056876 A1 | 3/2013 | Harvey et al. | |
| 2013/0110105 A1 | 5/2013 | Vankov | |
| 2013/0172881 A1 | 7/2013 | Hill et al. | |
| 2013/0190754 A1 | 7/2013 | Paul et al. | |
| 2013/0226170 A1 | 8/2013 | Seddon et al. | |
| 2013/0282000 A1 | 10/2013 | Parsonage | |
| 2014/0094791 A1 | 4/2014 | Hull et al. | |
| 2014/0100557 A1 | 4/2014 | Bohner et al. | |
| 2014/0166098 A1 | 6/2014 | Kian et al. | |

FOREIGN PATENT DOCUMENTS

| | | |
|---|---|---|
| WO | 97/33522 A1 | 9/1997 |
| WO | 2012/068273 A1 | 5/2012 |

OTHER PUBLICATIONS

International Search Report and Written Opinion received for PCT Patent Application No. PCT/US2011/061026, mailed on Feb. 23, 2012, 8 pages.

International Search Report received for PCT Patent Application No. PCT/US2013/064657, mailed on Jan. 10, 2014, 2 pages.

Office Action Received for Australian Patent Application No. 2011328926, issued on Jun. 2, 2014, 4 pages.

Written Opinion received for Singapore Patent Application No. 201303477-2, mailed on Oct. 14, 2014, 10 pages.

International Search Report and Written Opinion received for PCT Patent Application No. PCT/US2014/029731, mailed on Aug. 22, 2014, 12 pages.

Written Opinion received for PCT Patent Application No. PCT/US2013/064657, mailed on Jan. 10, 2014, 10 pages.

* cited by examiner

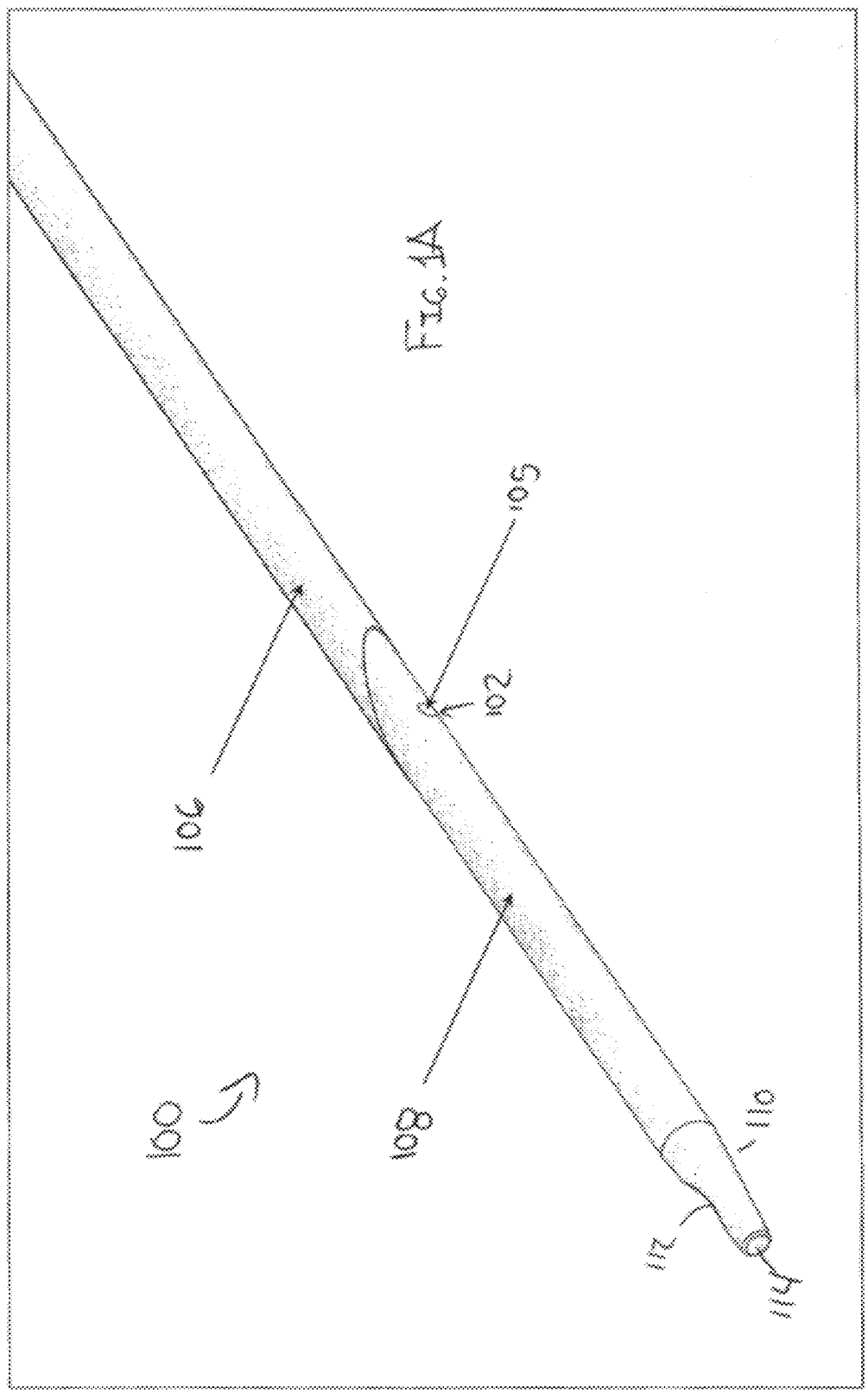

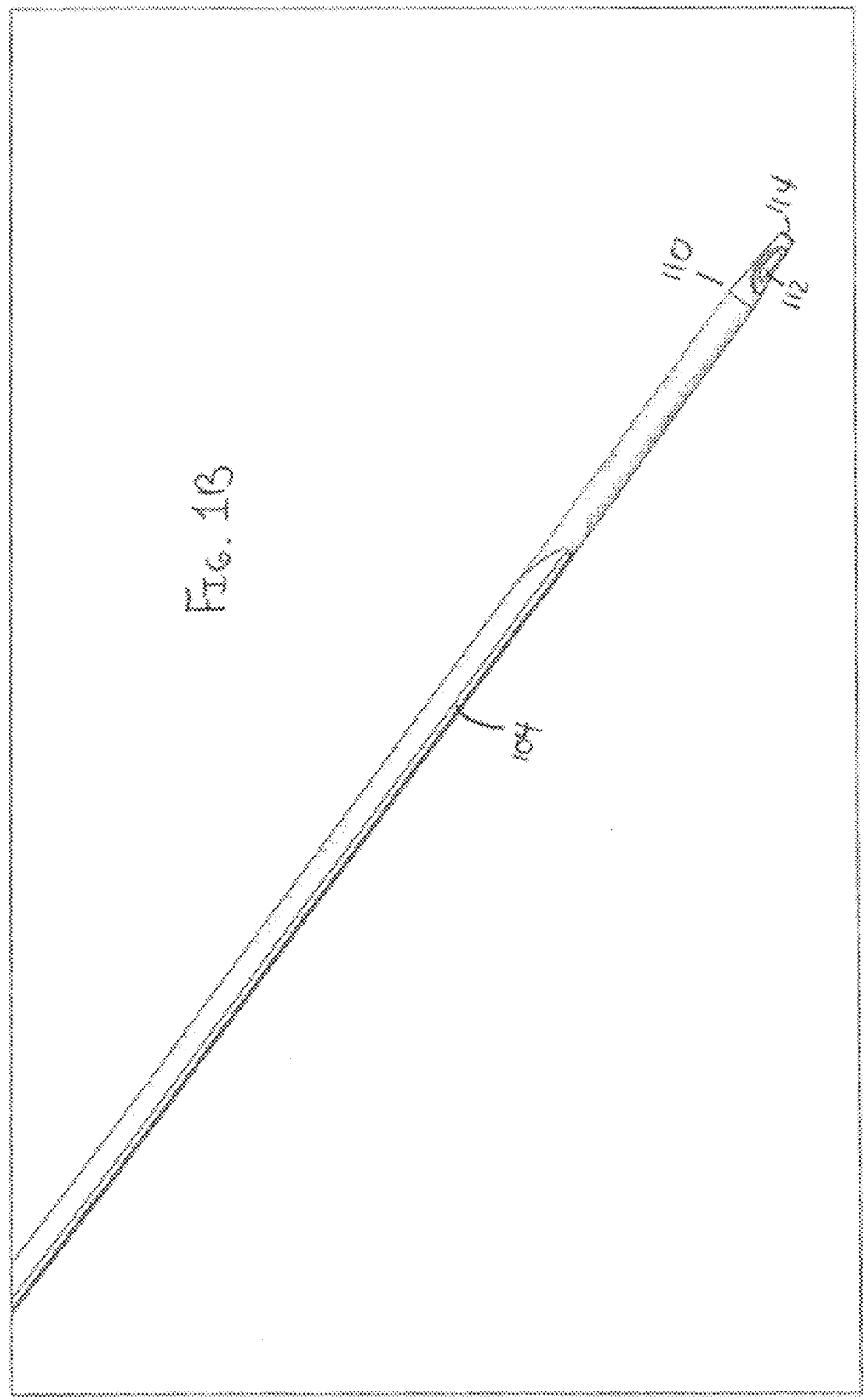

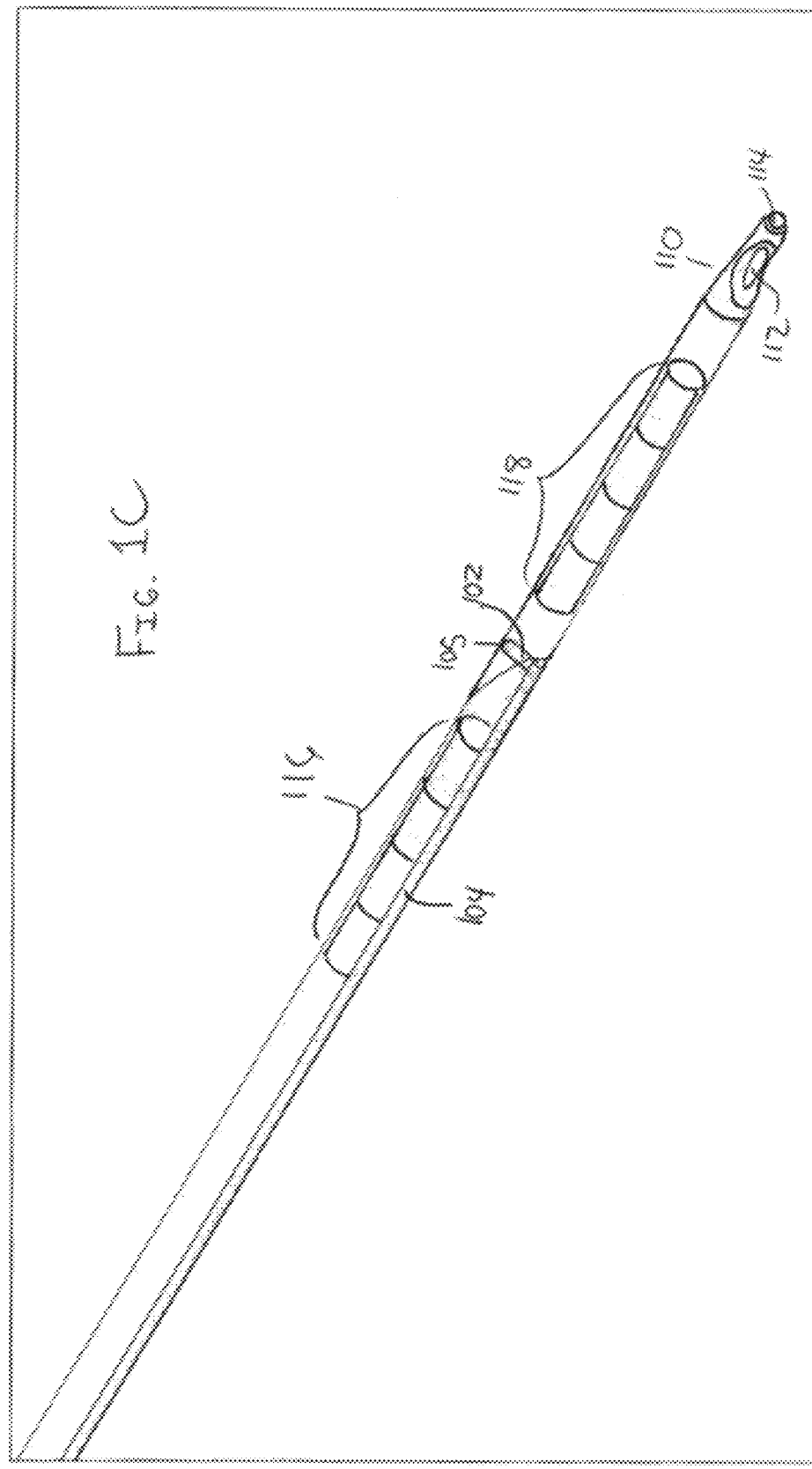

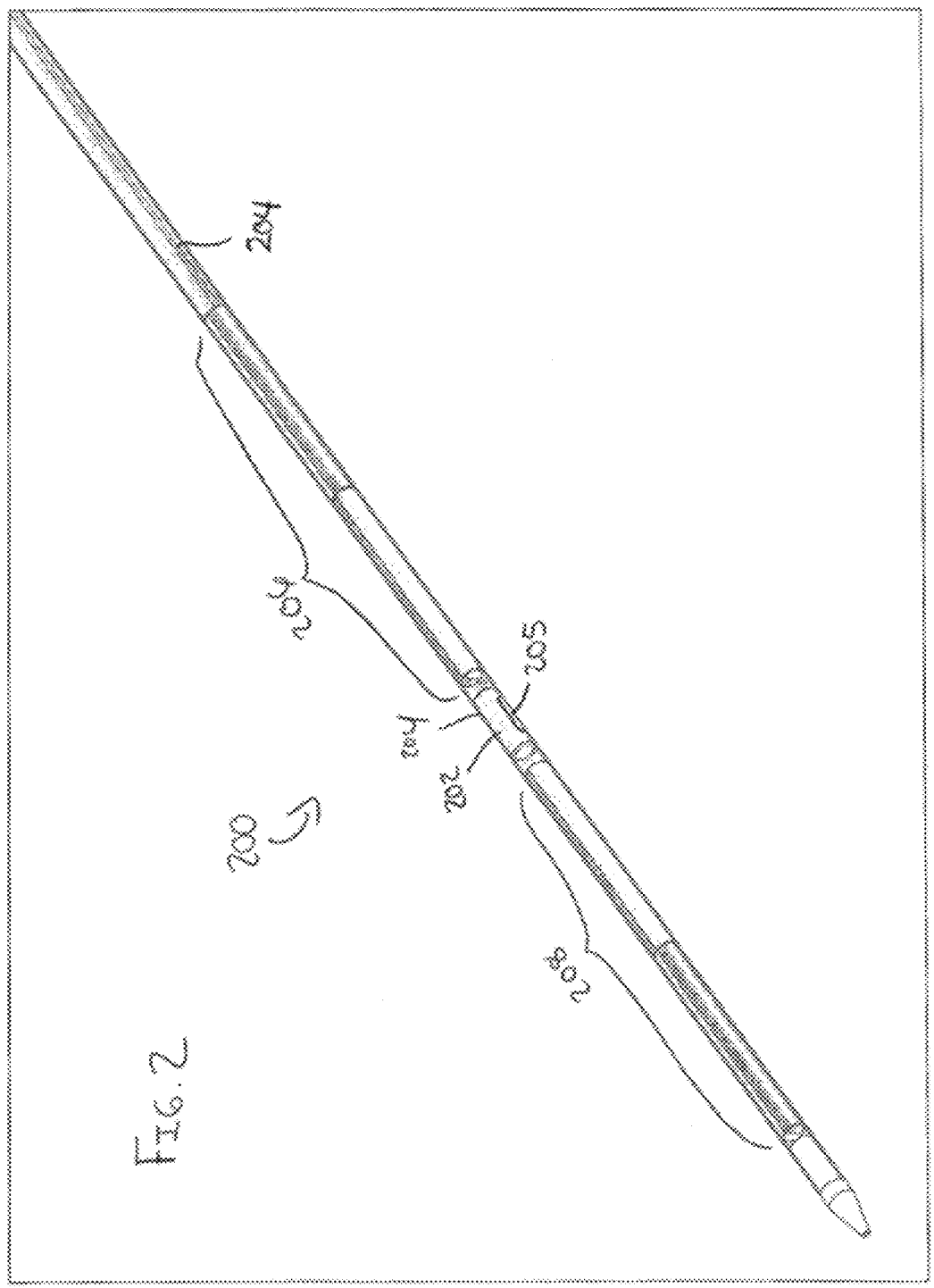

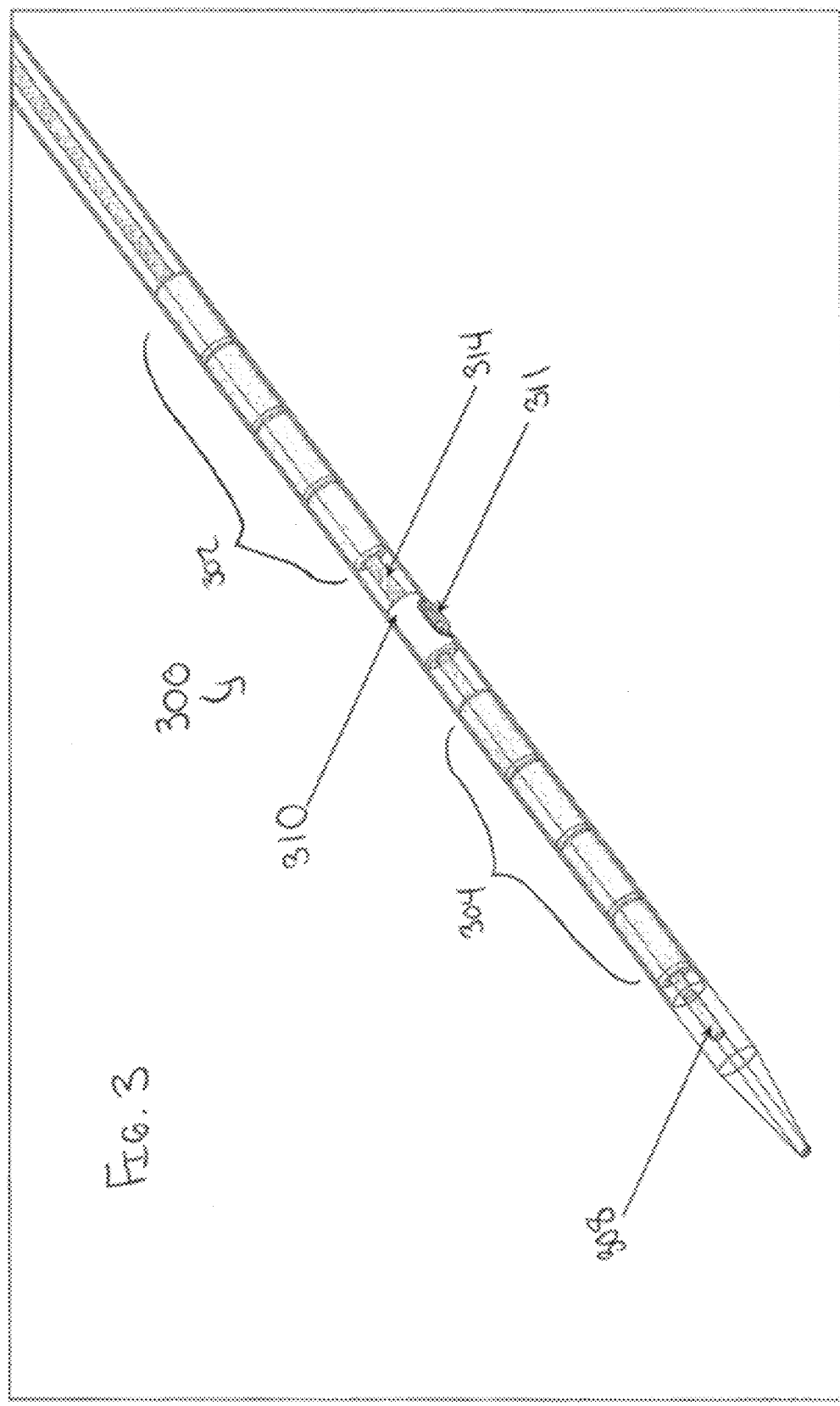

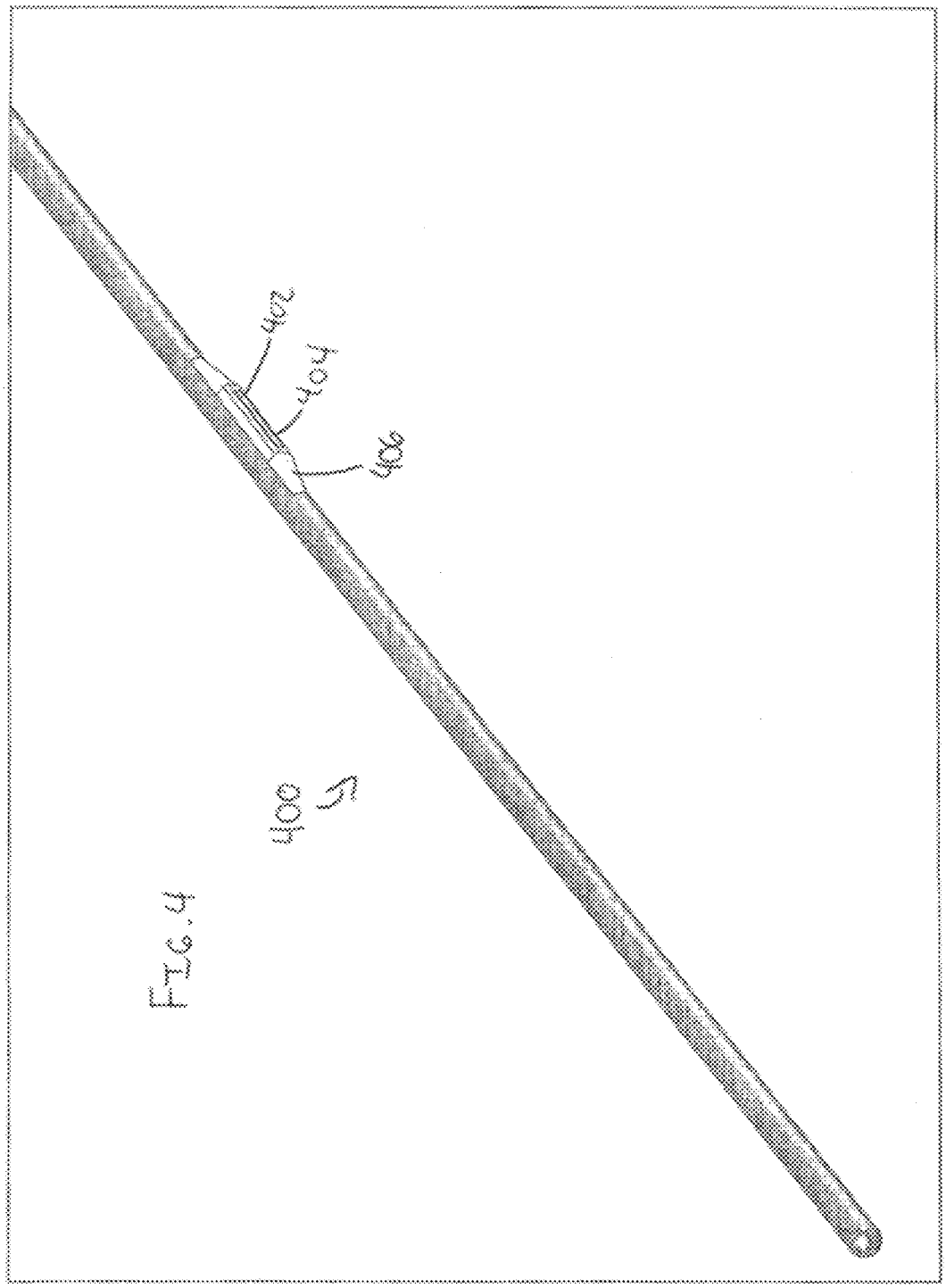

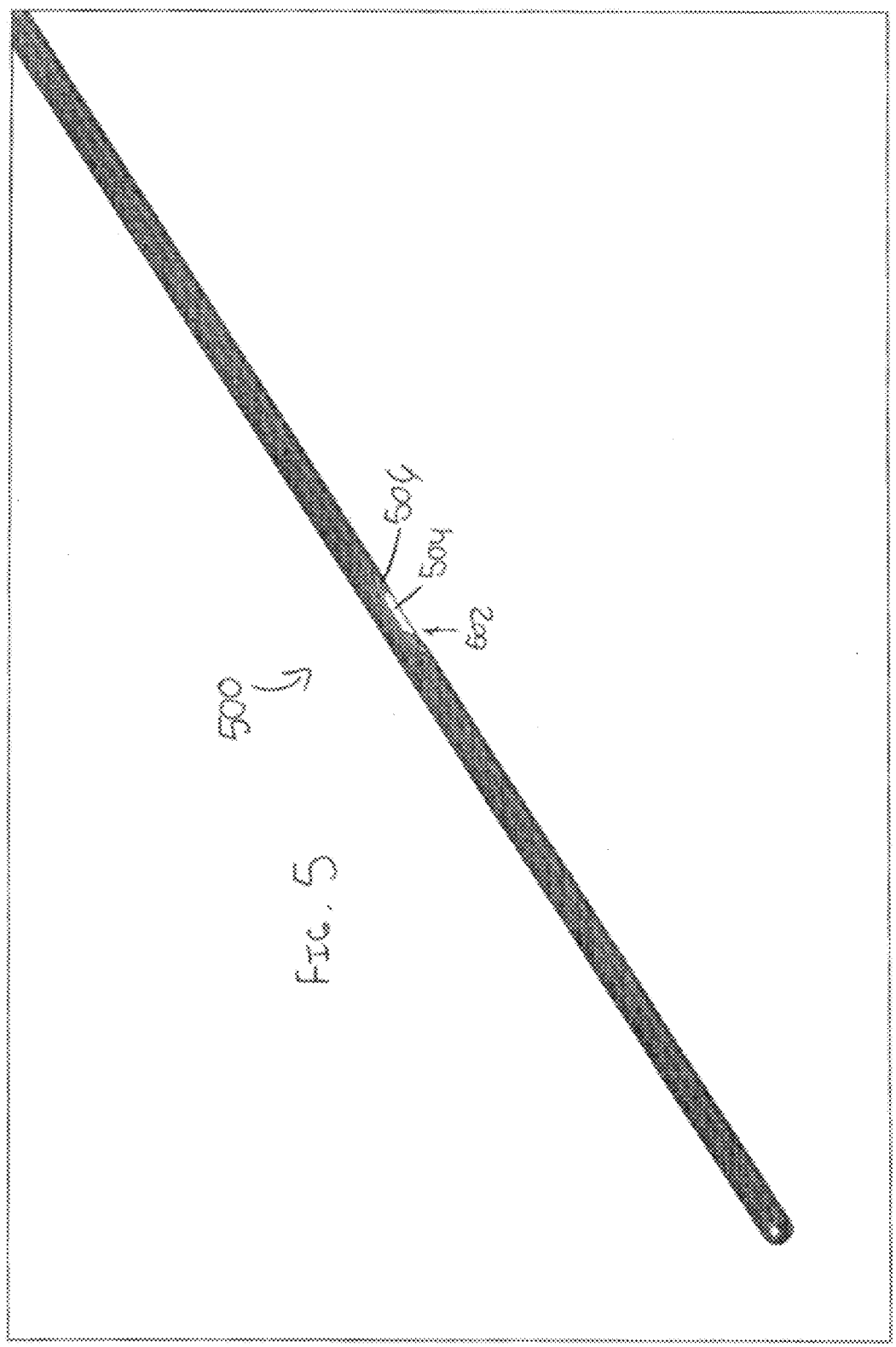

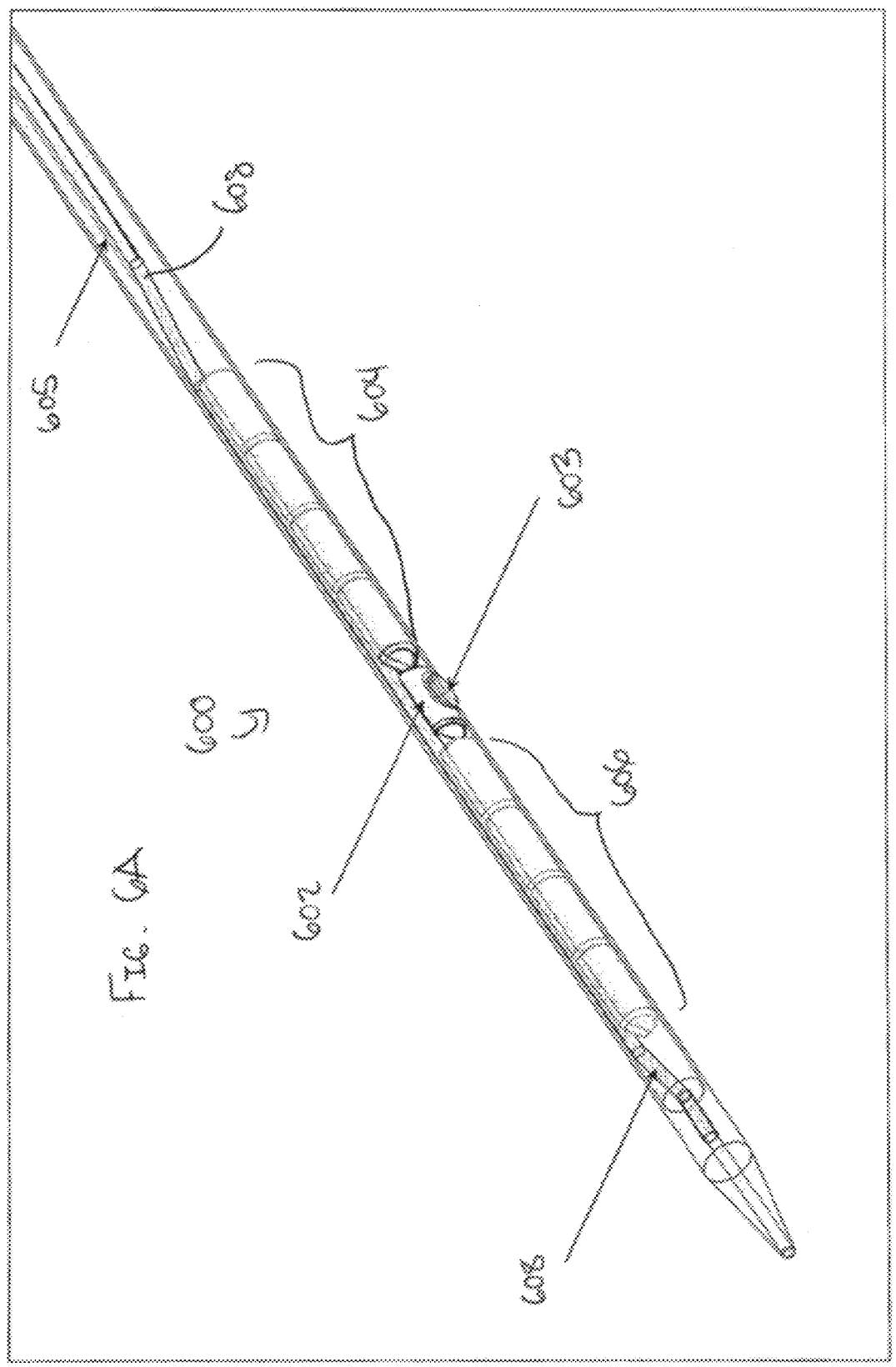

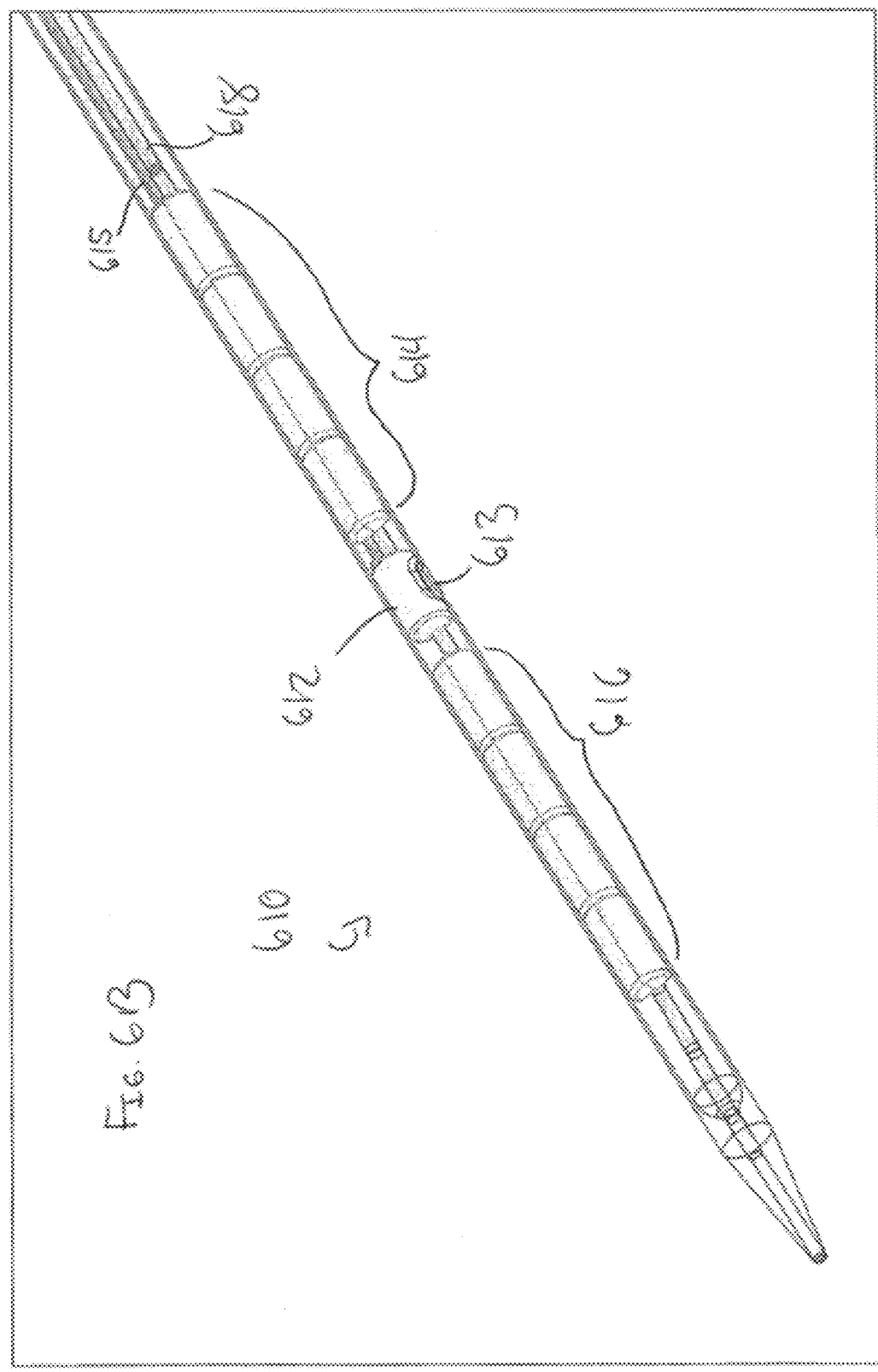

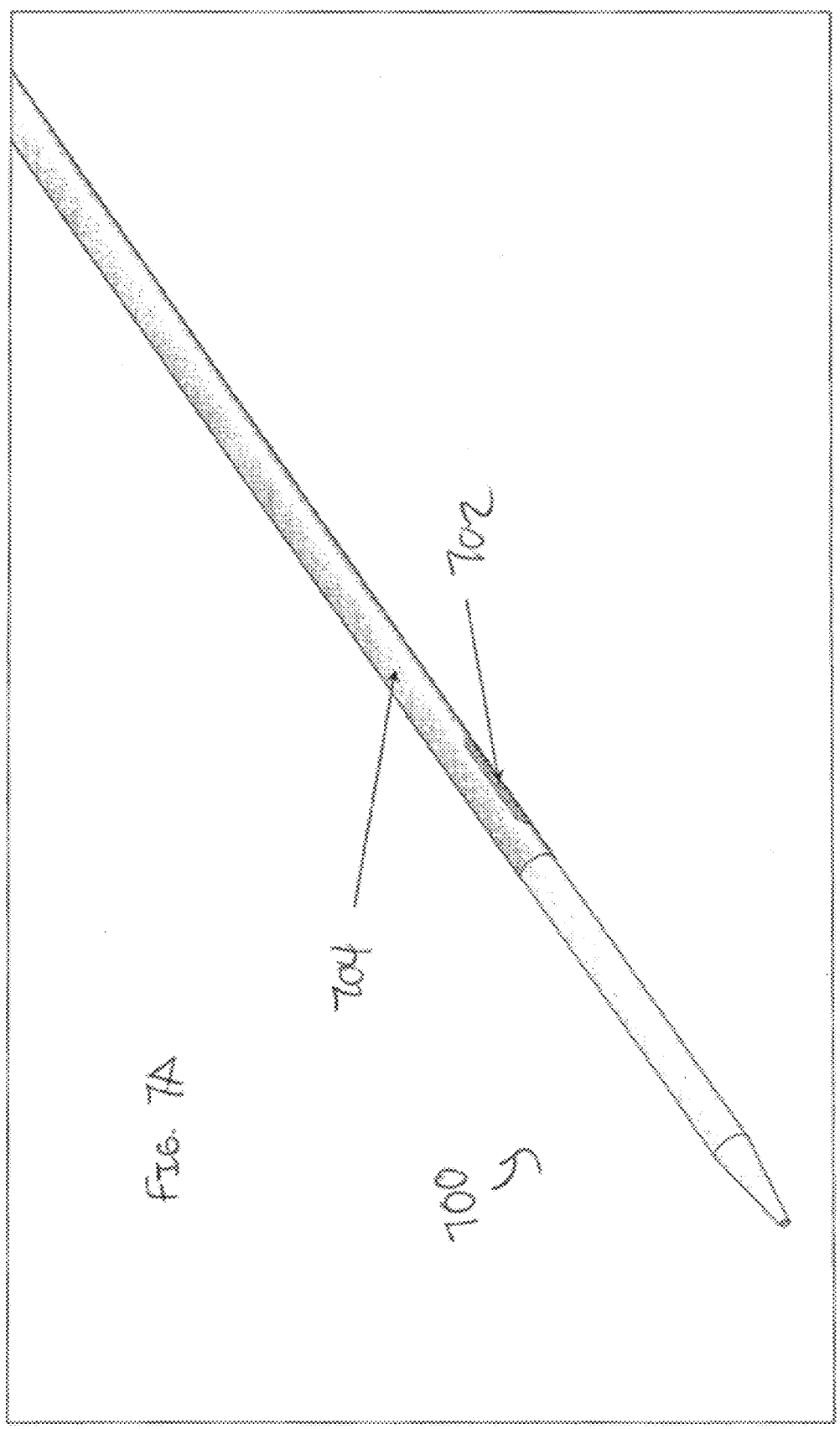

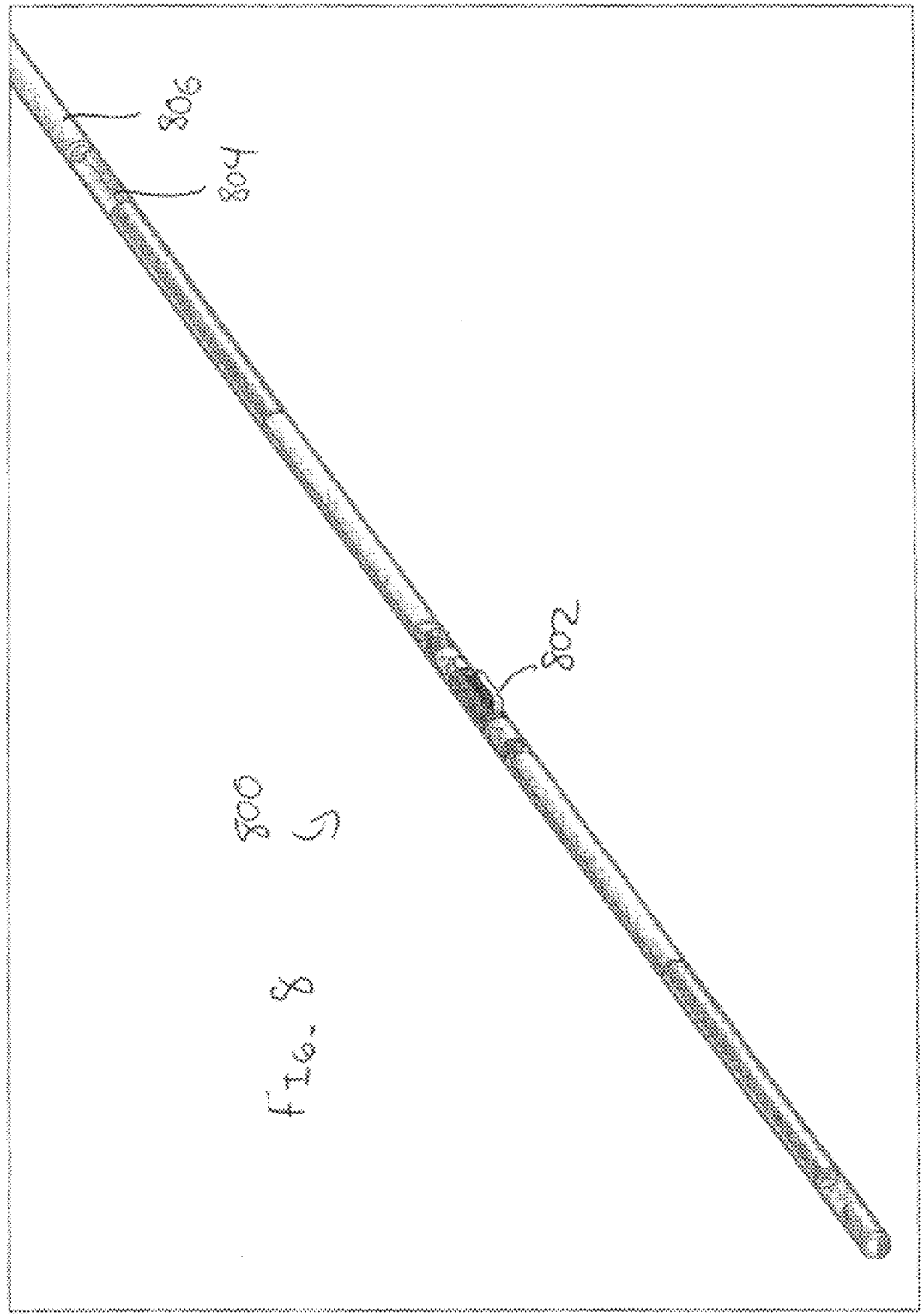

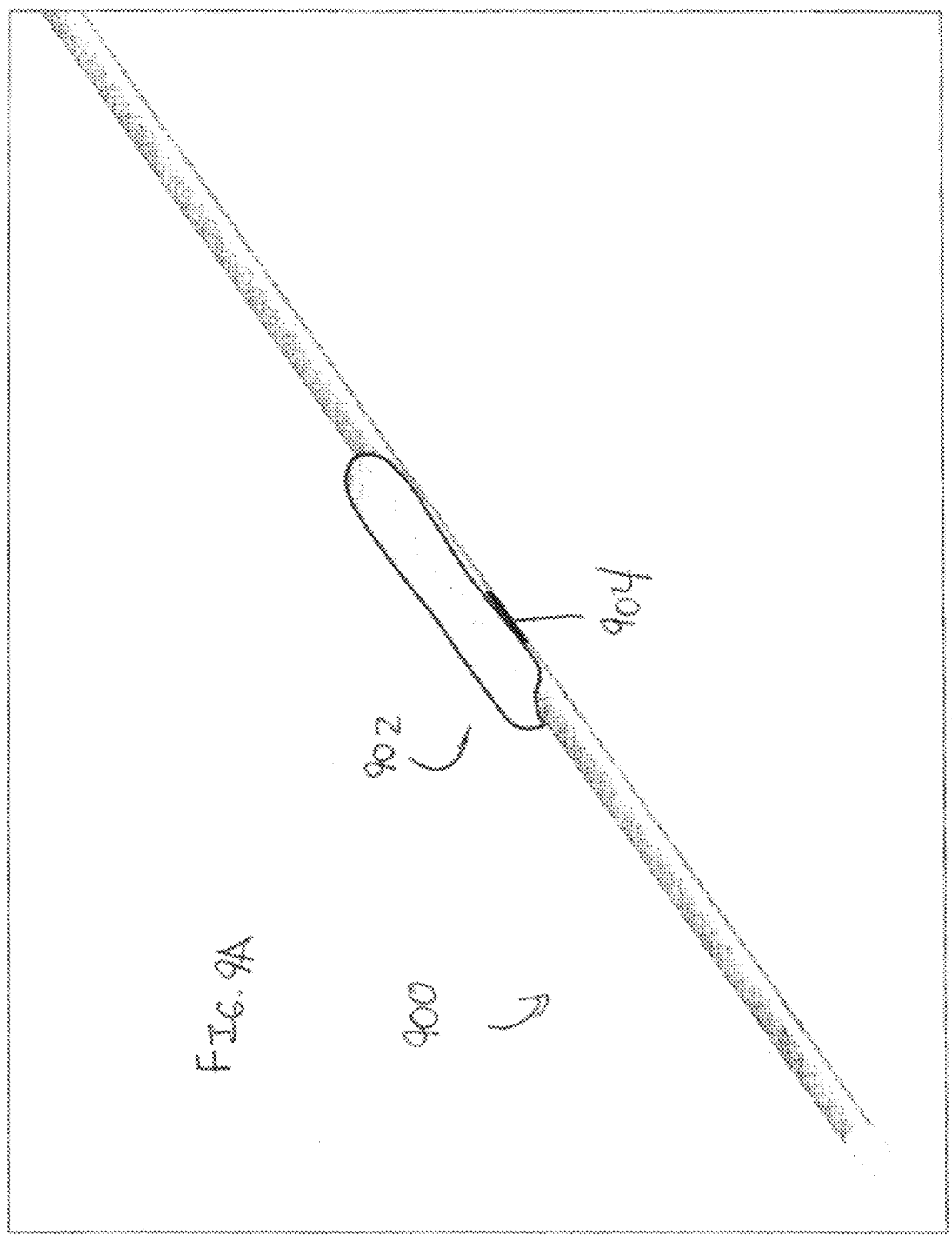

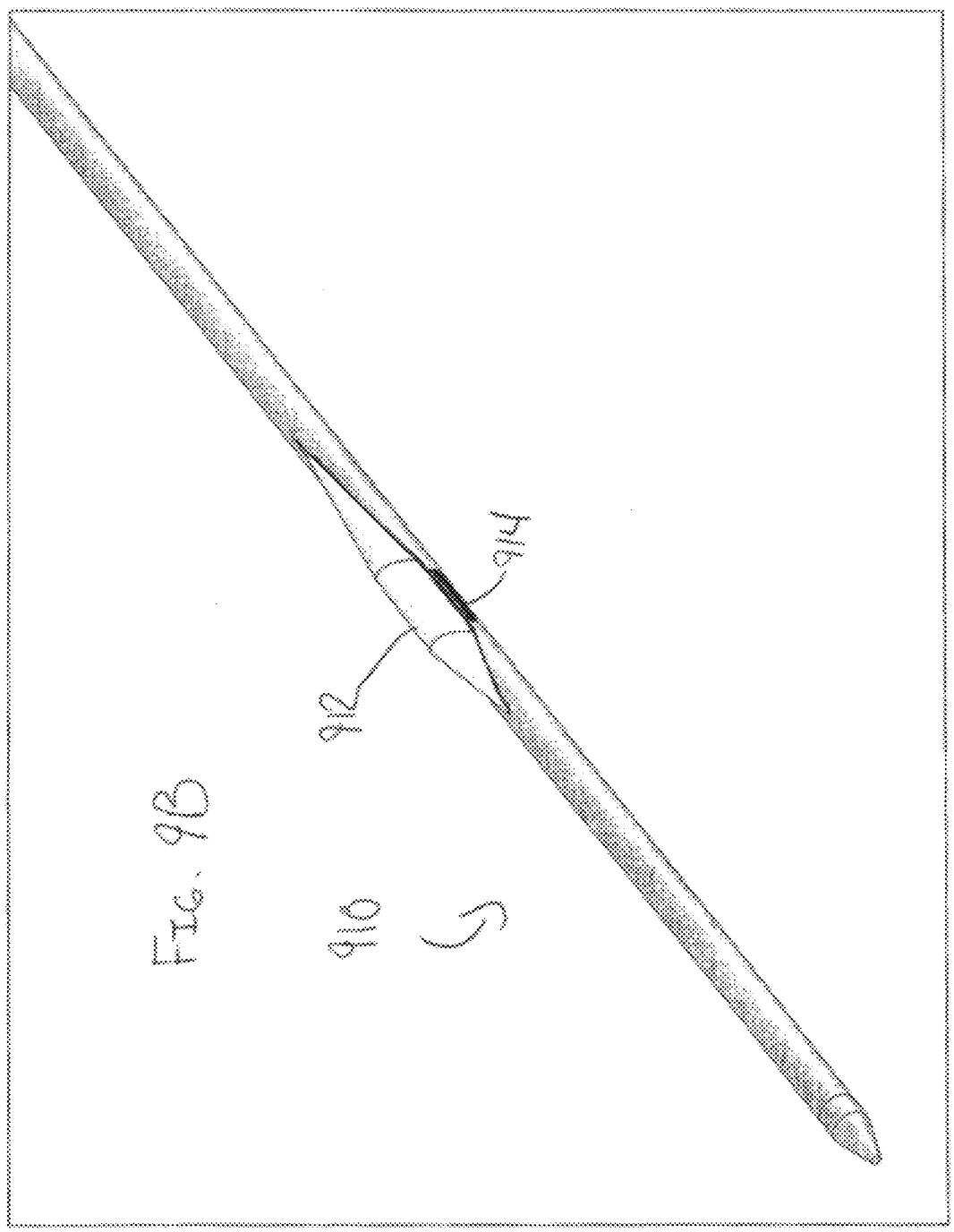

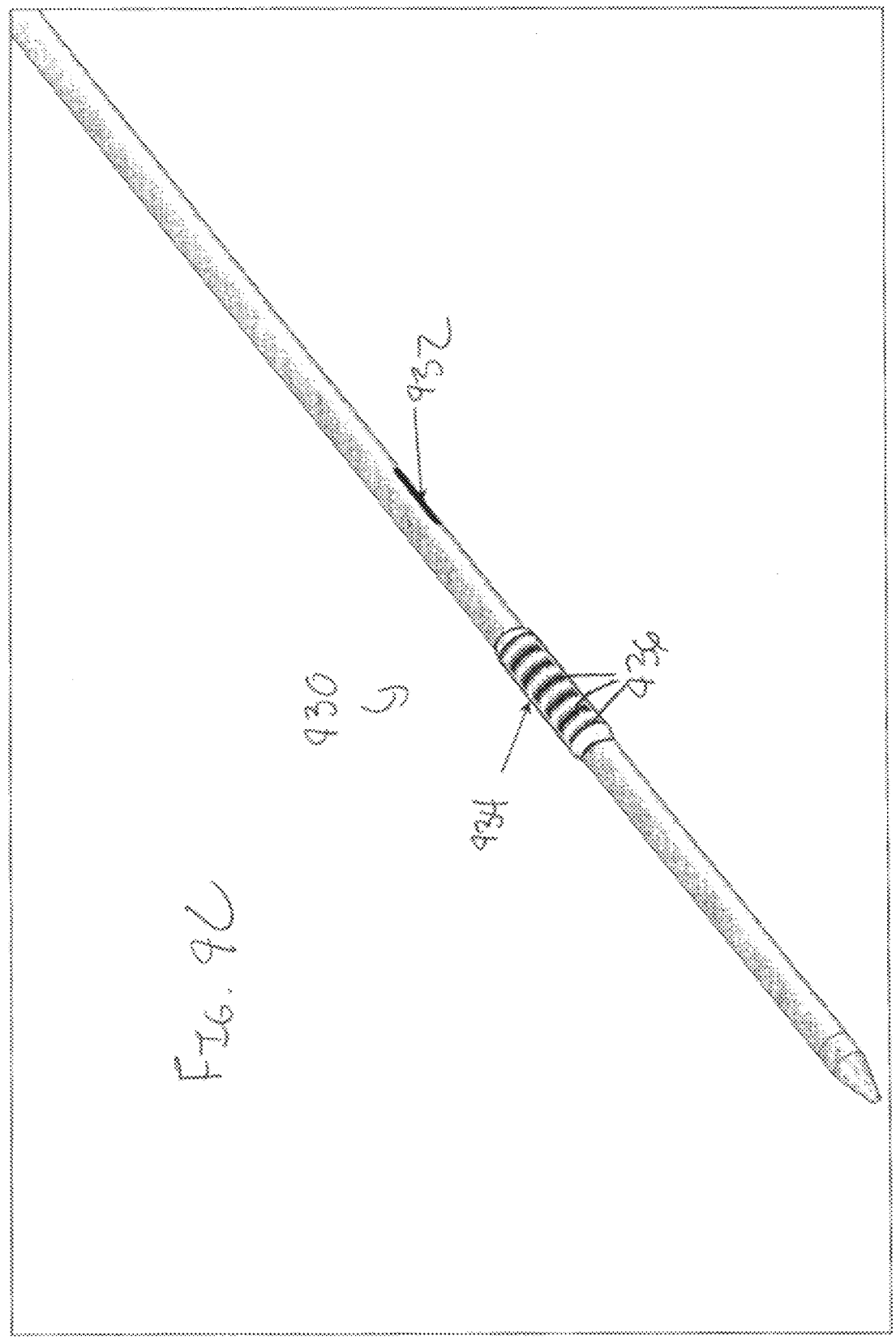

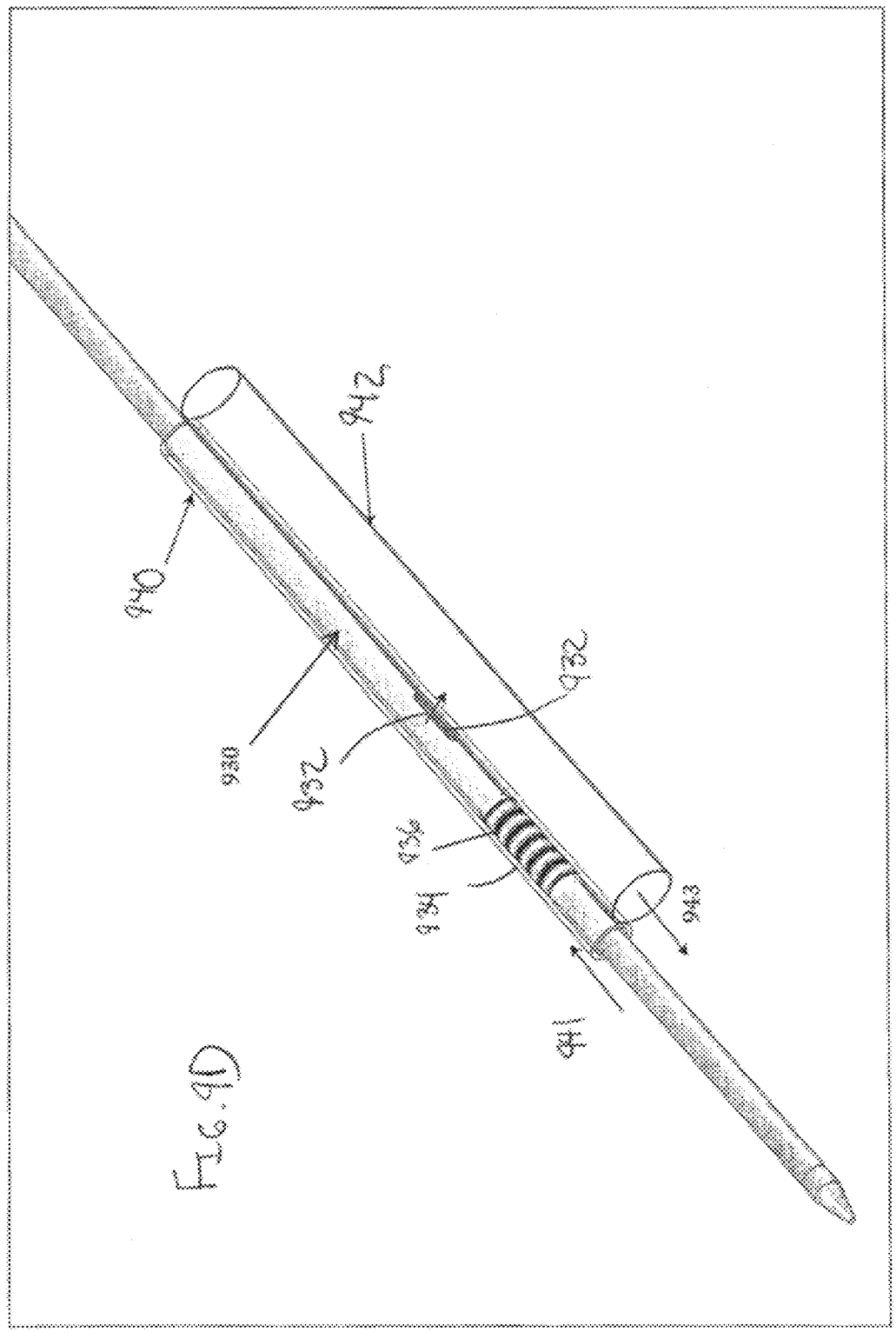

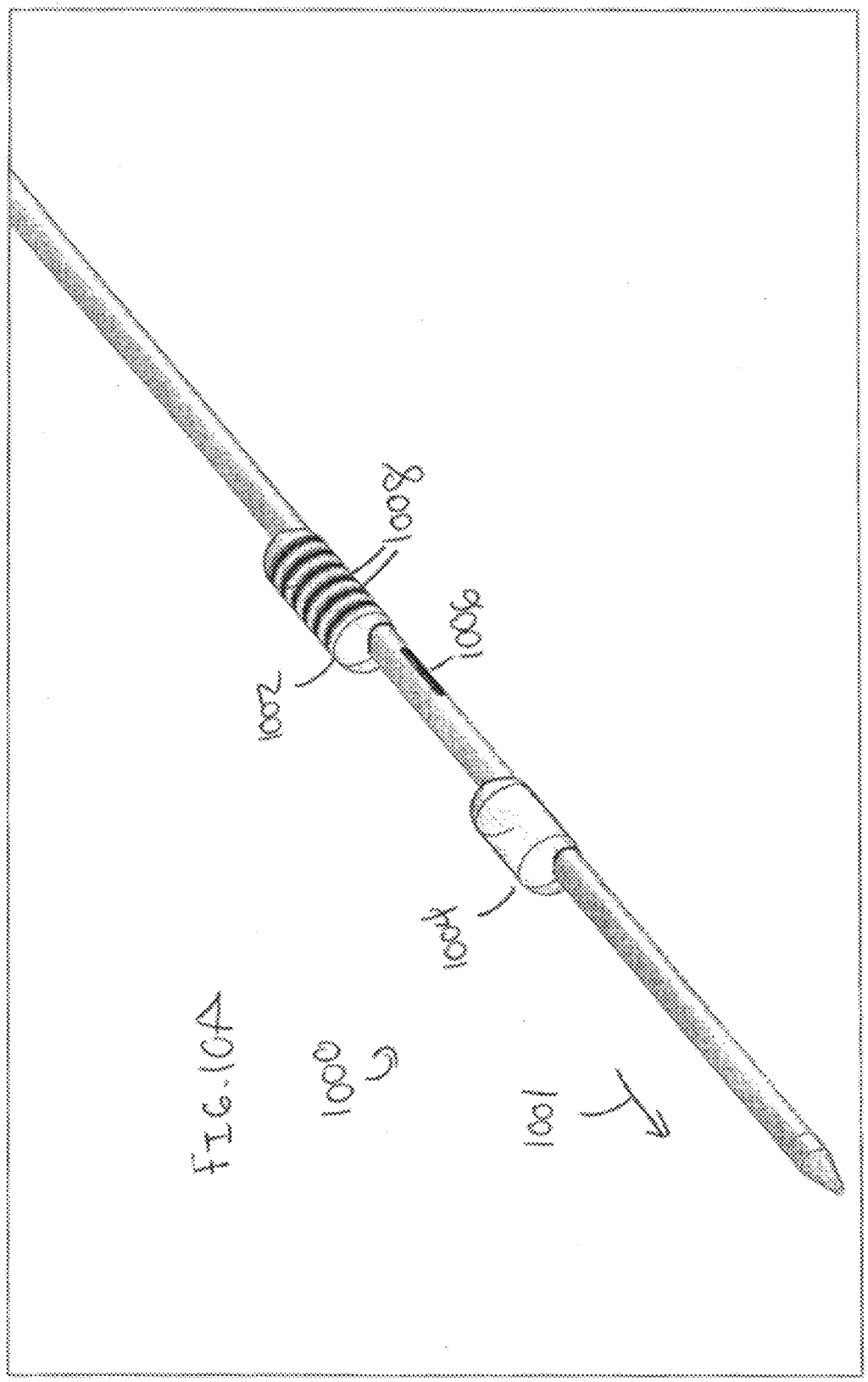

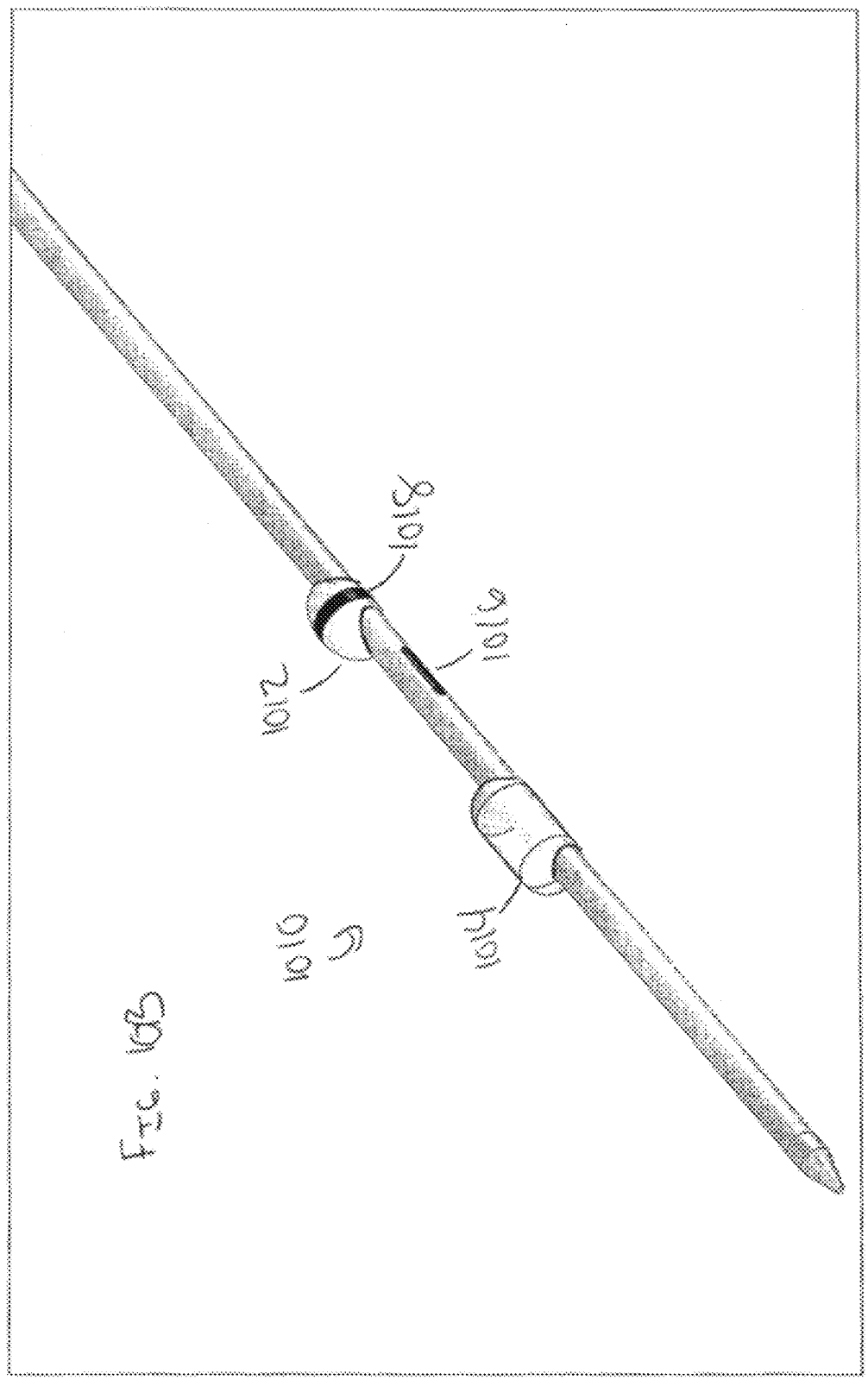

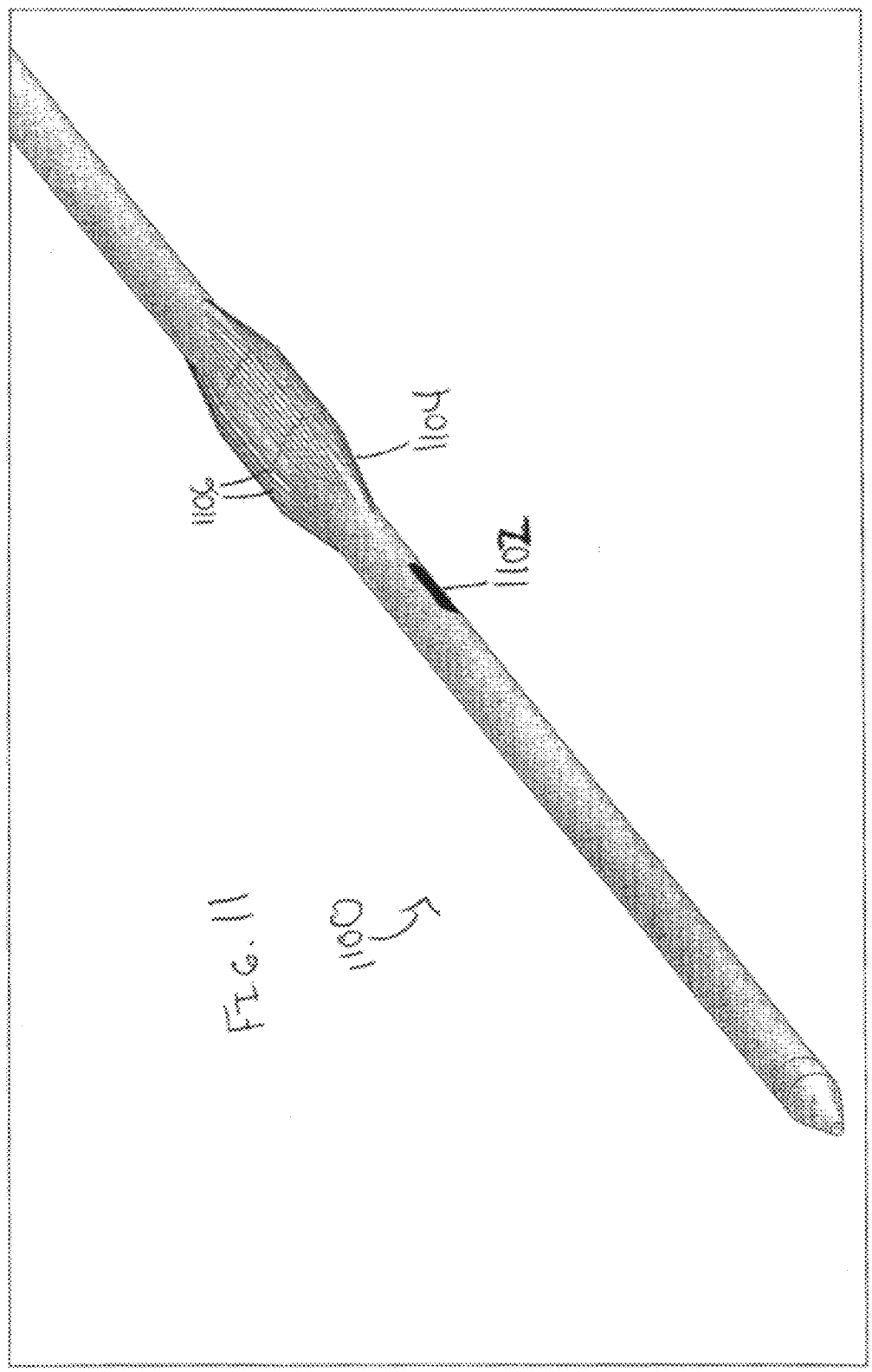

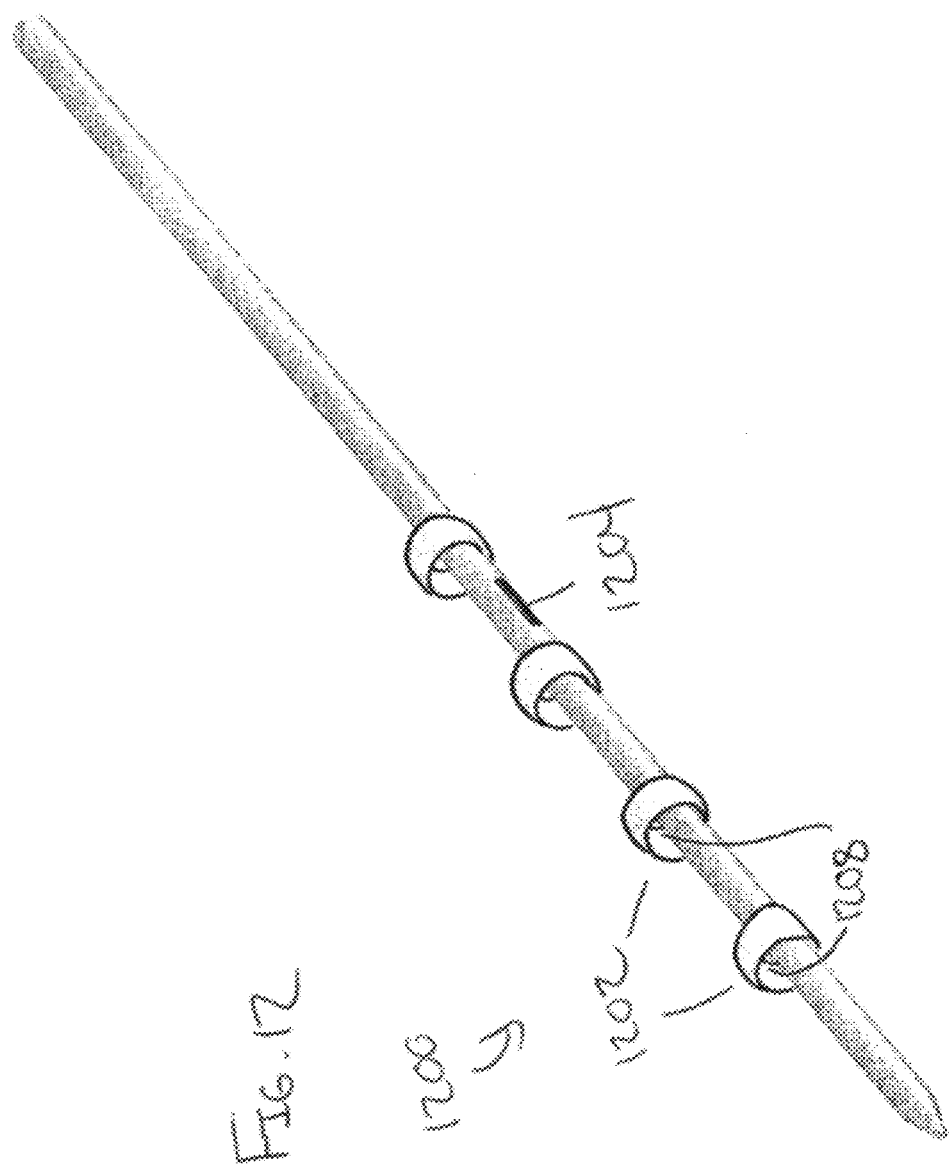

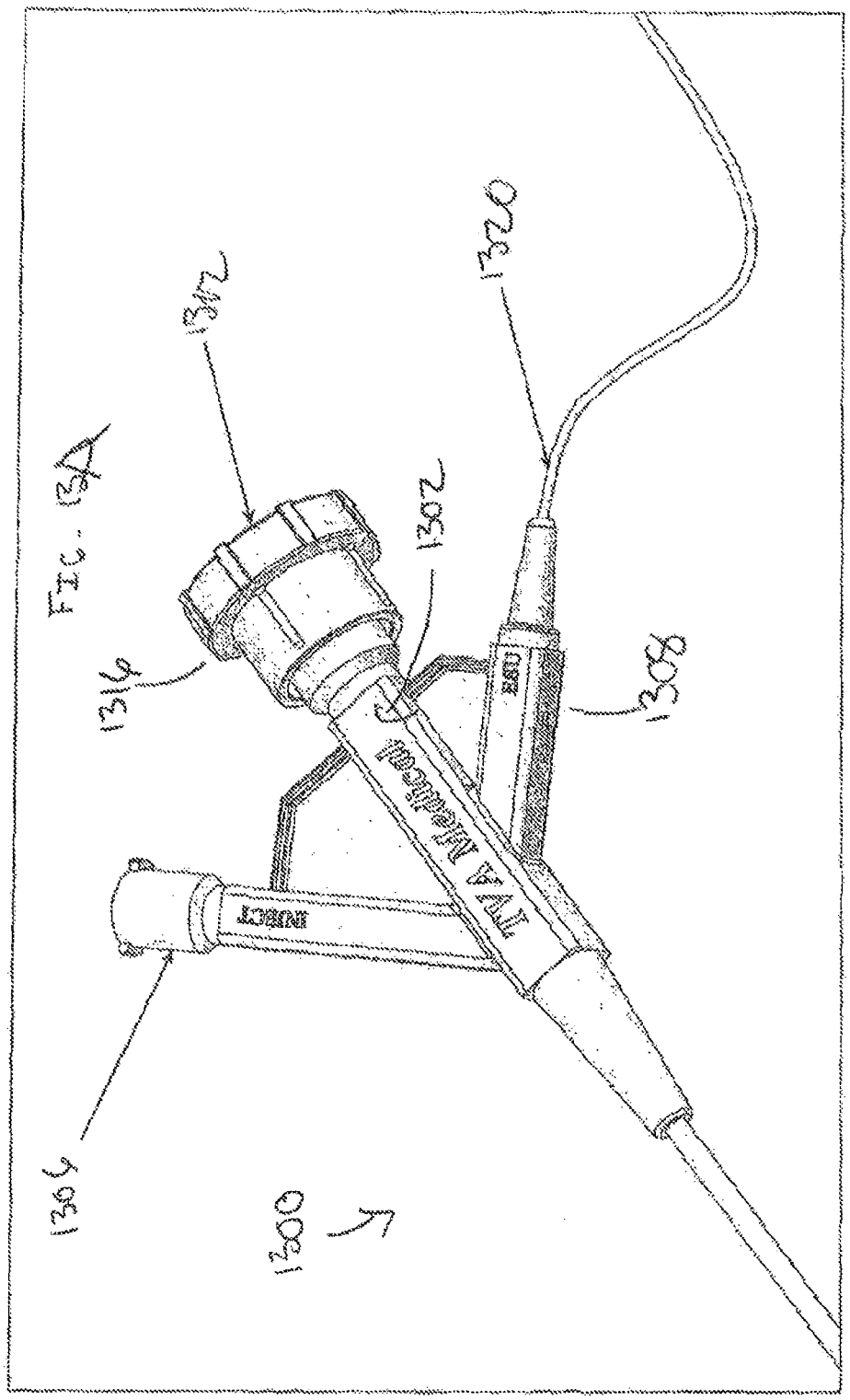

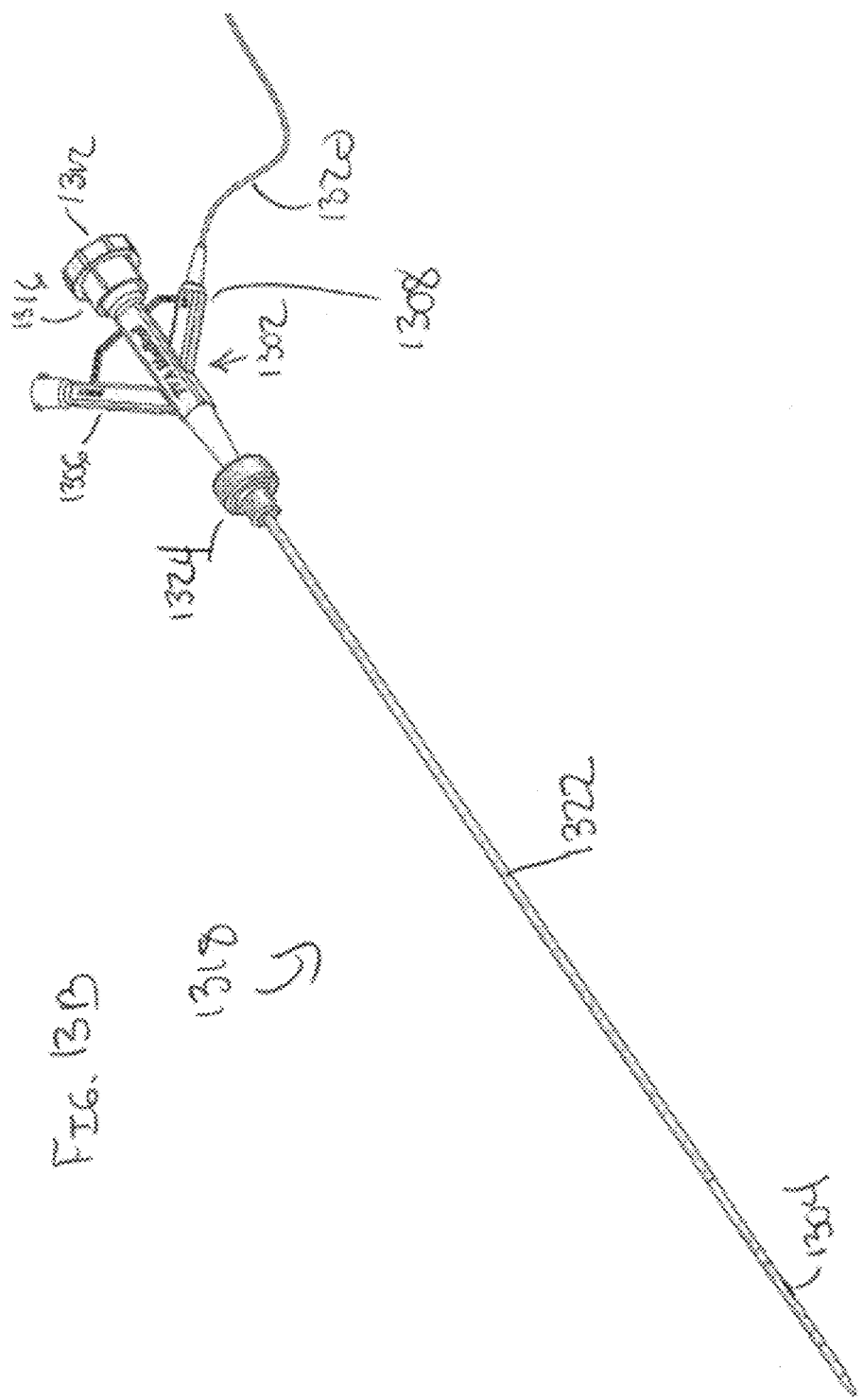

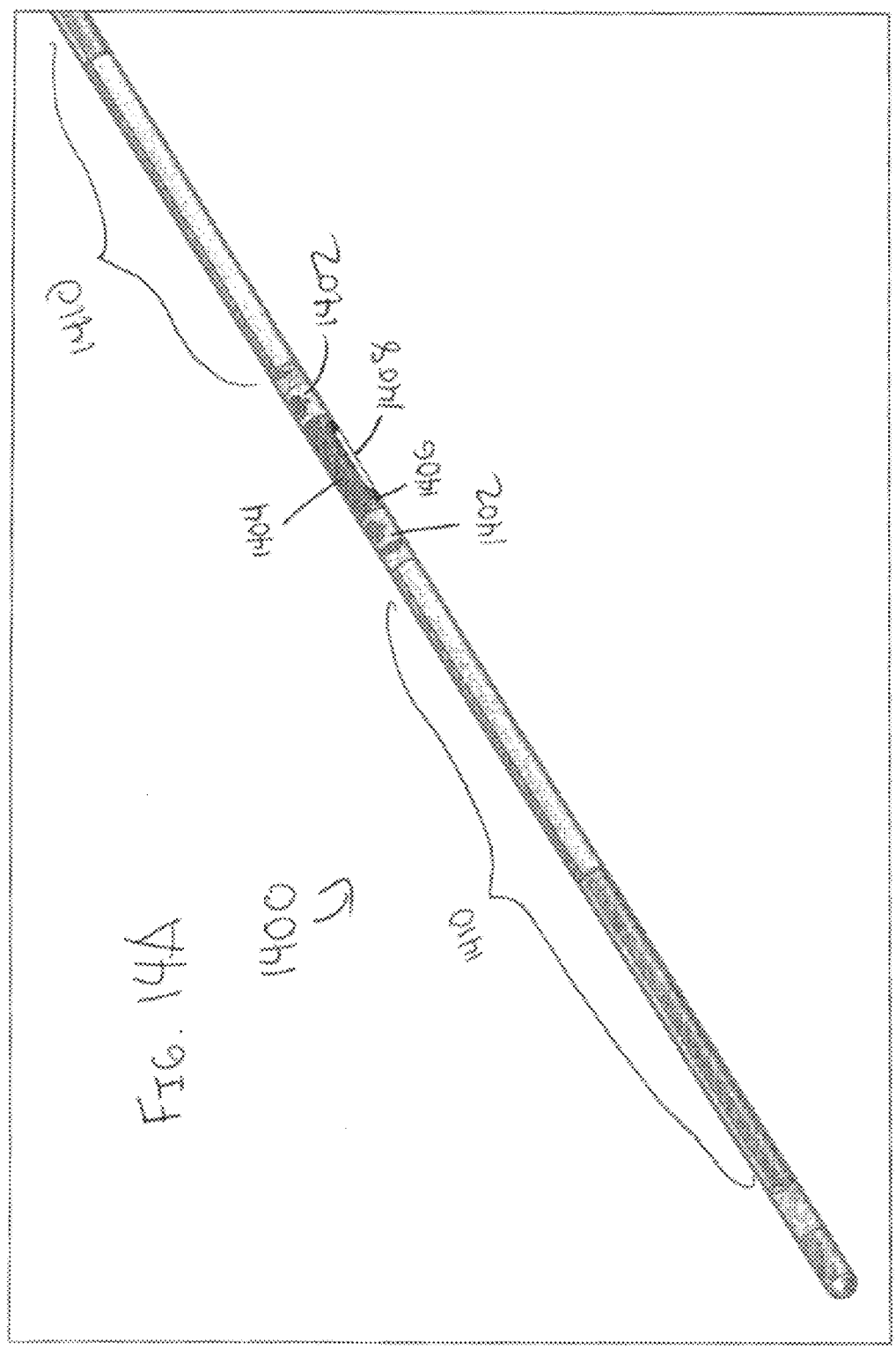

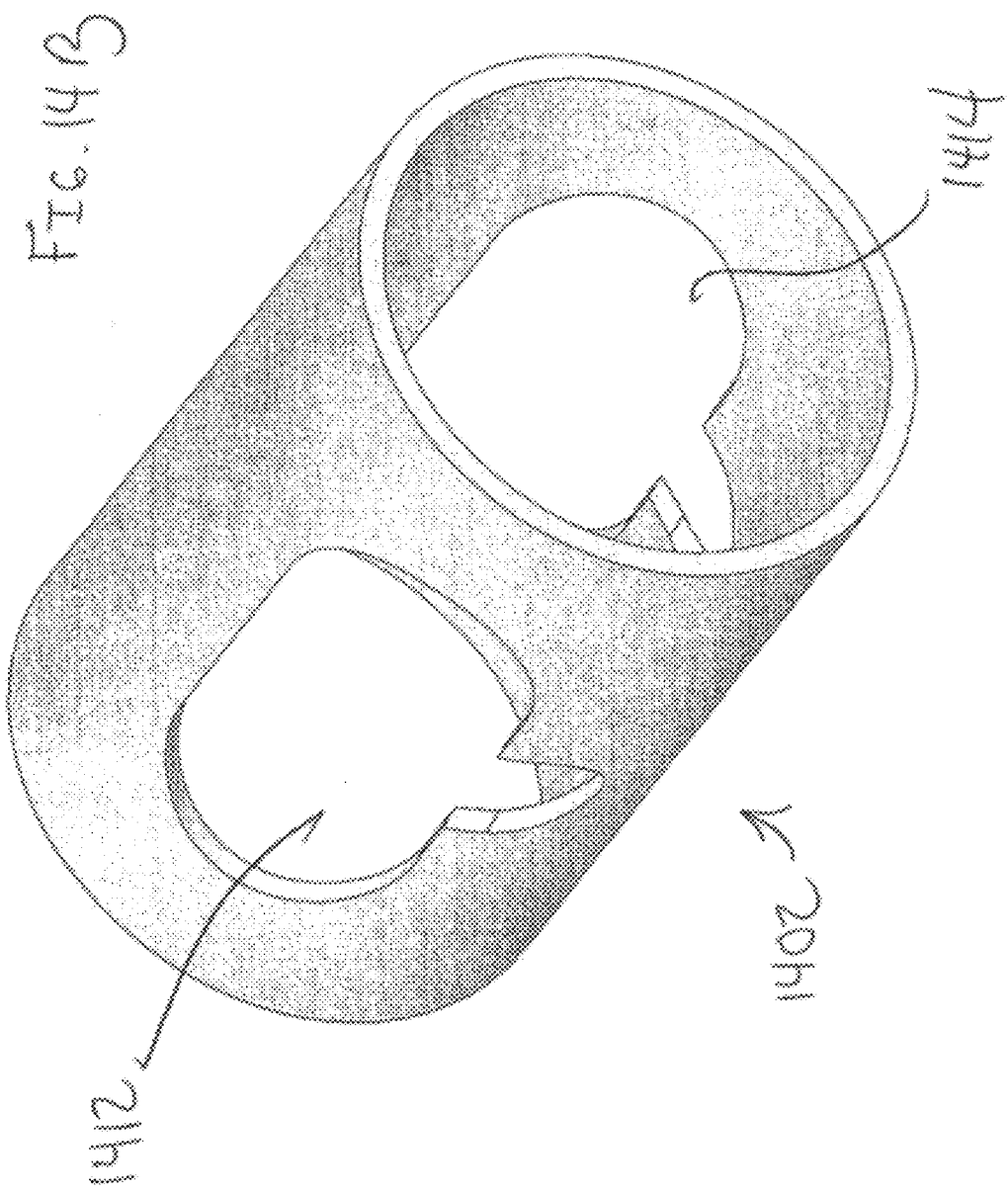

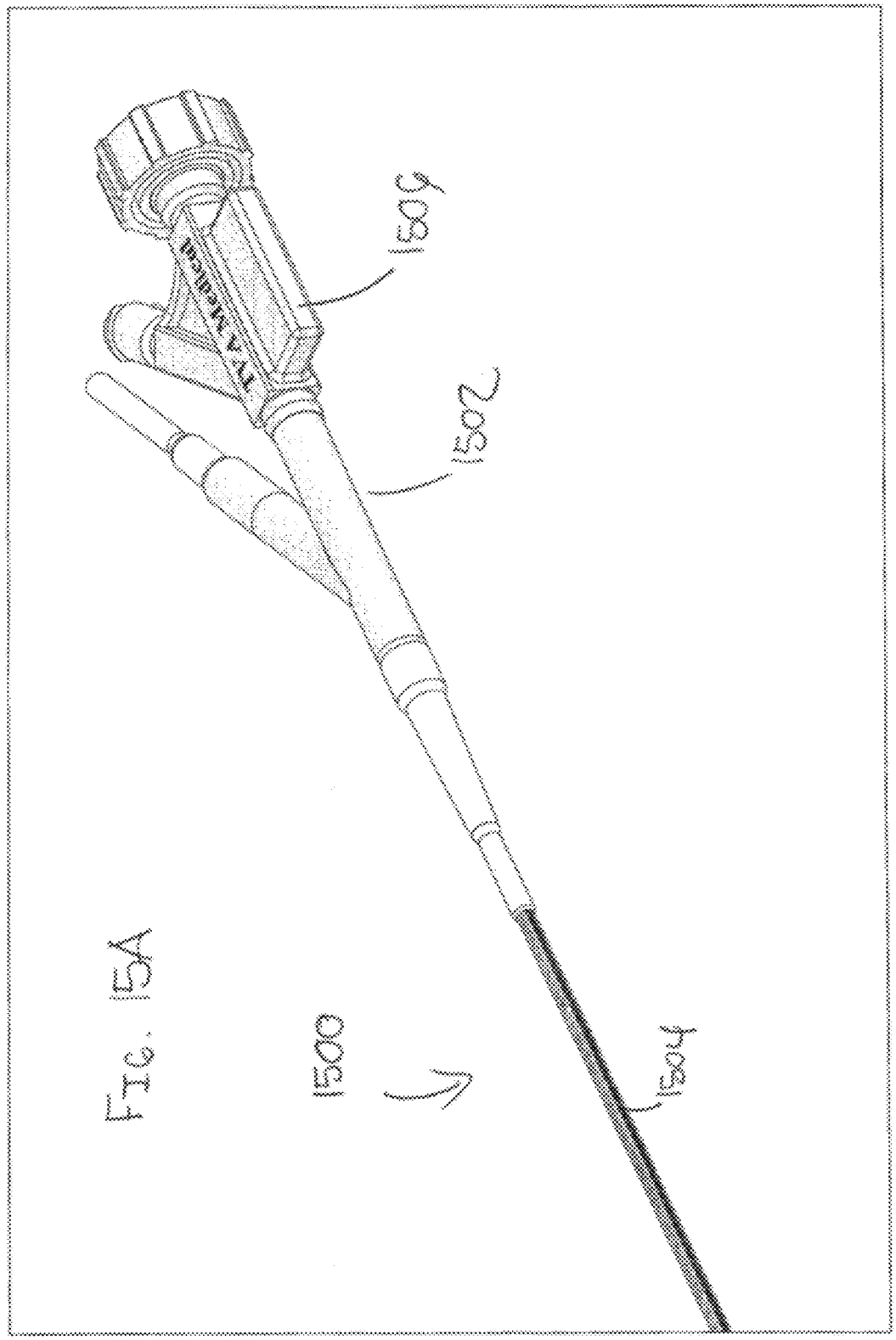

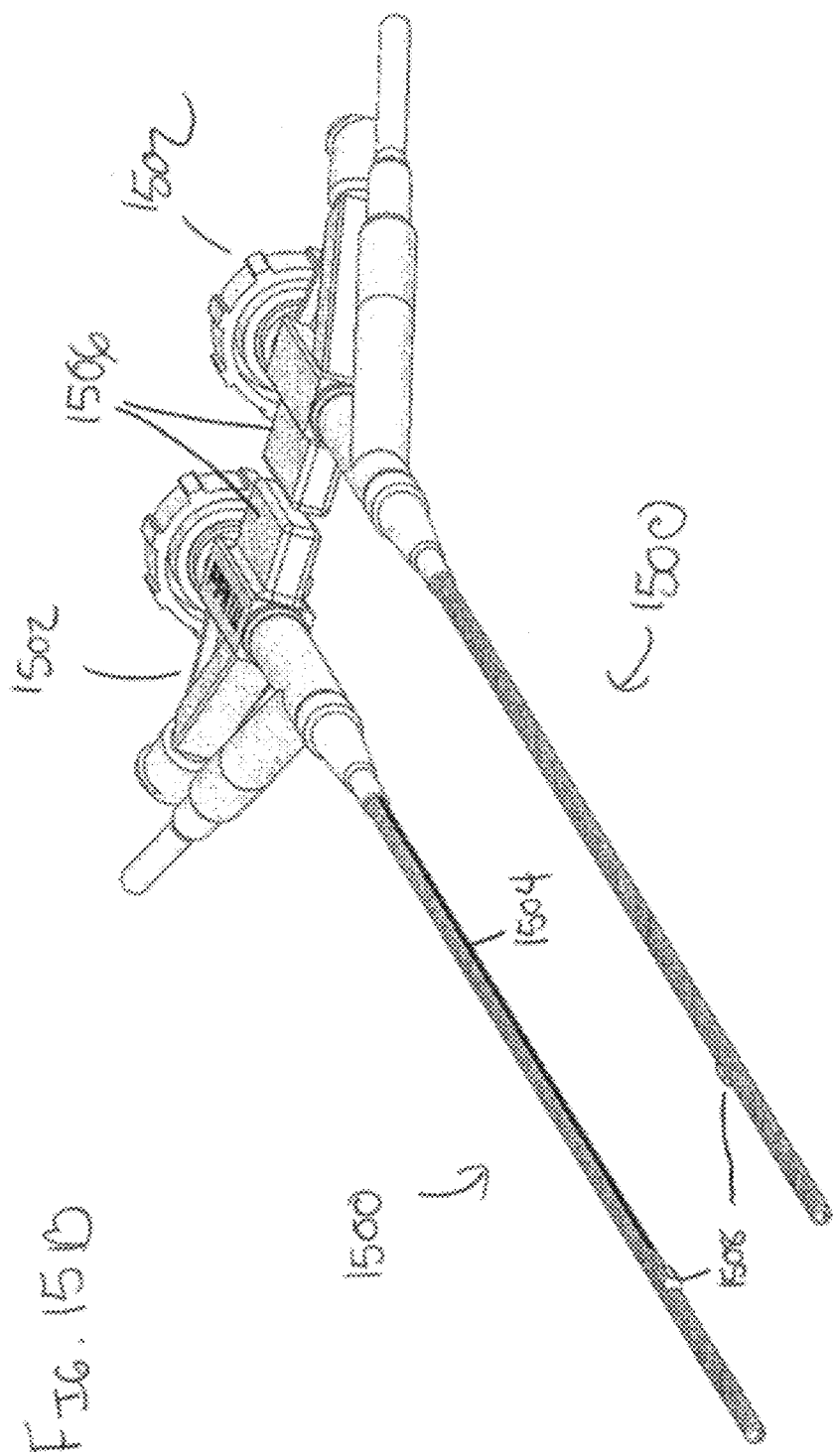

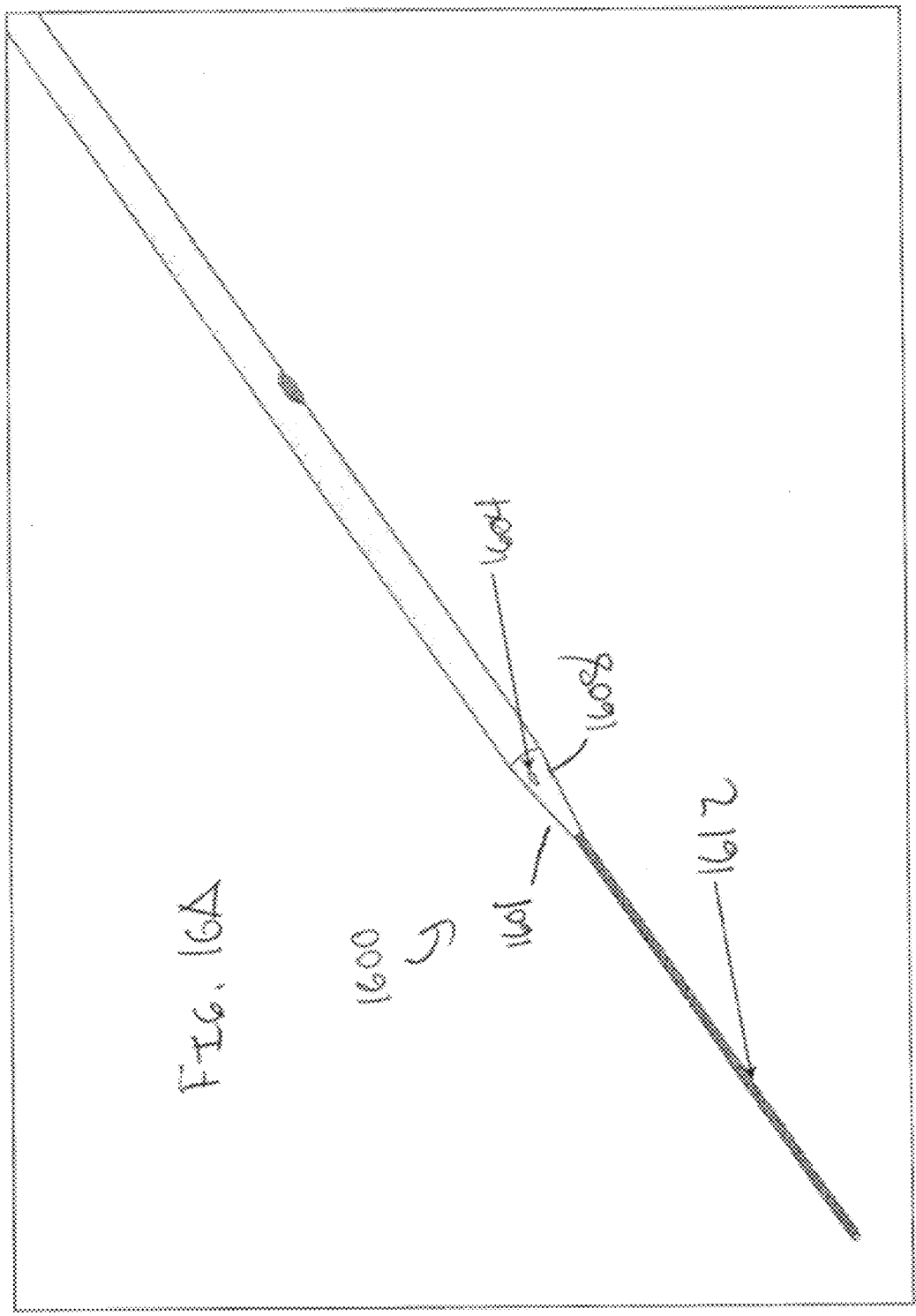

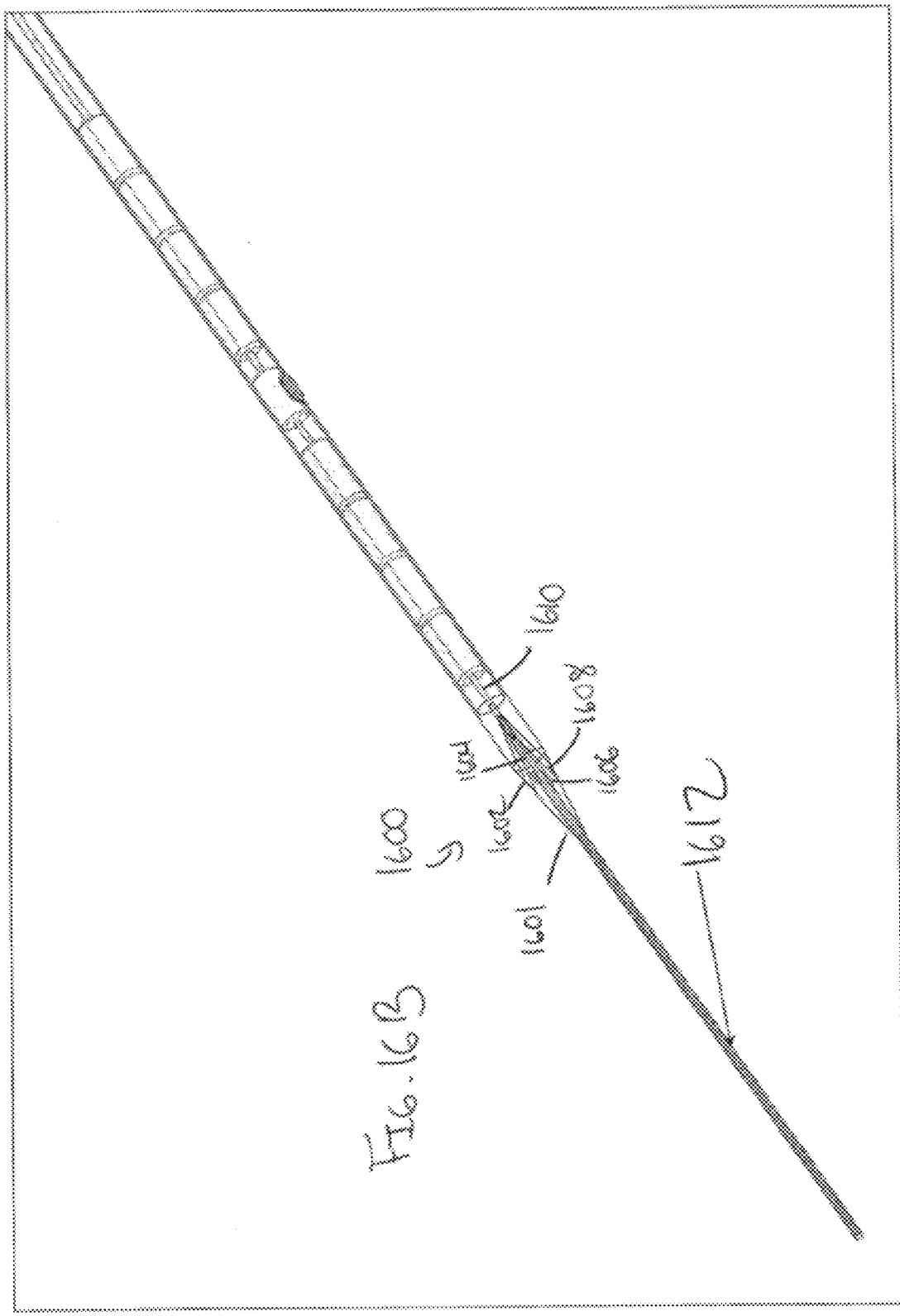

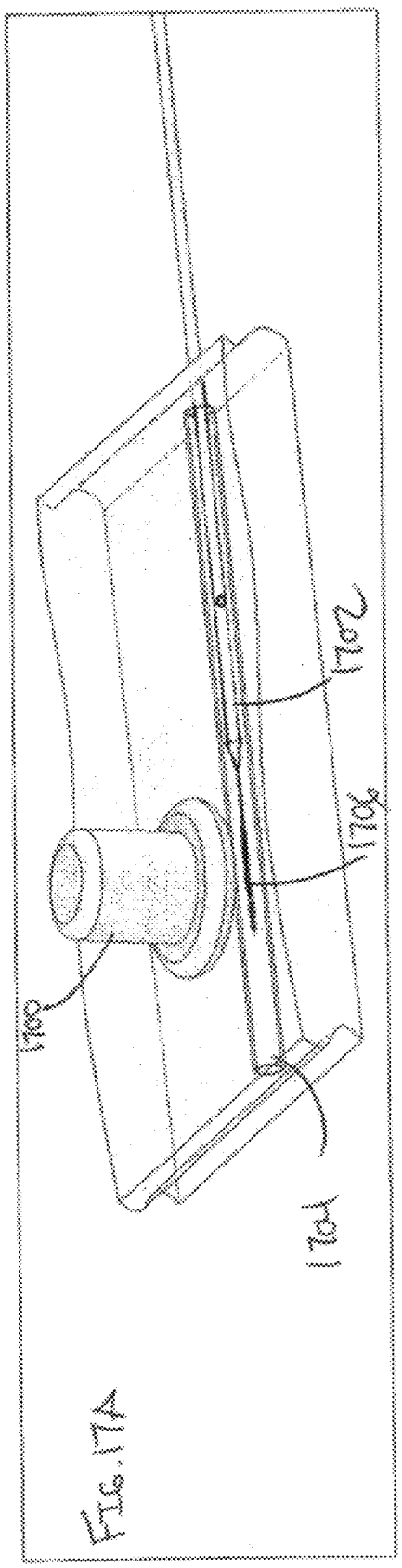
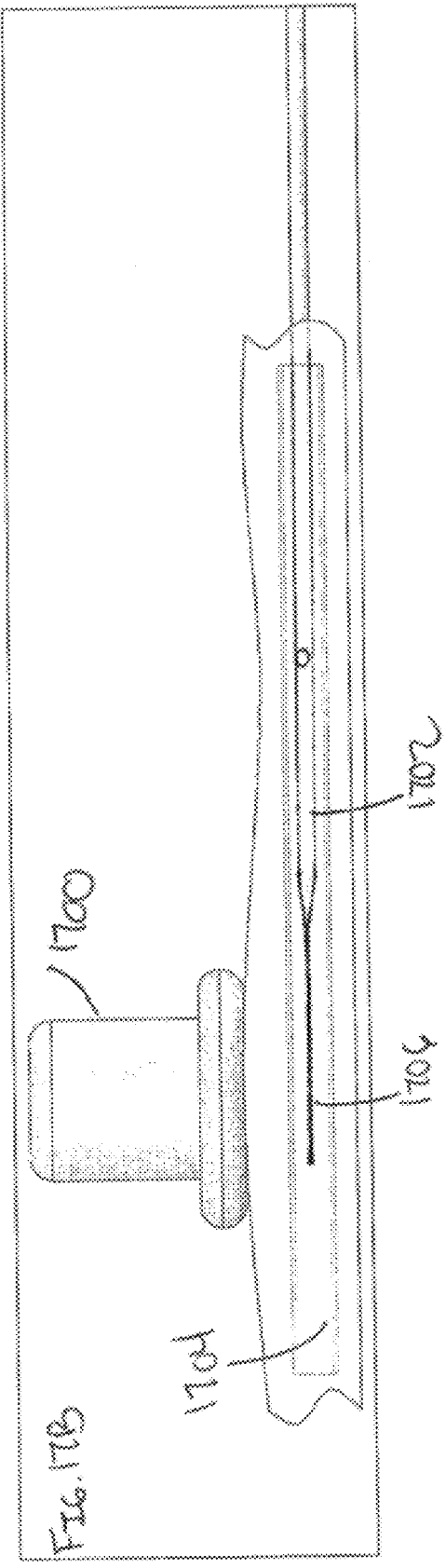

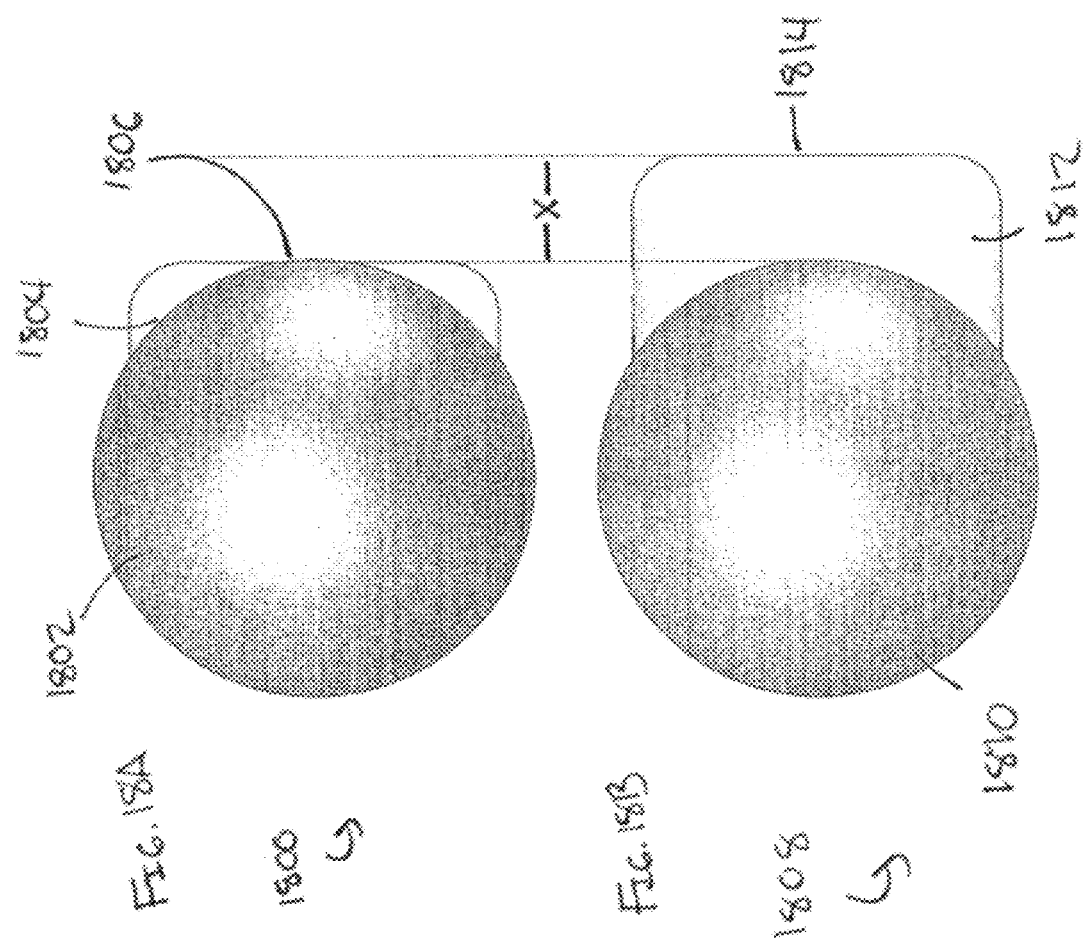

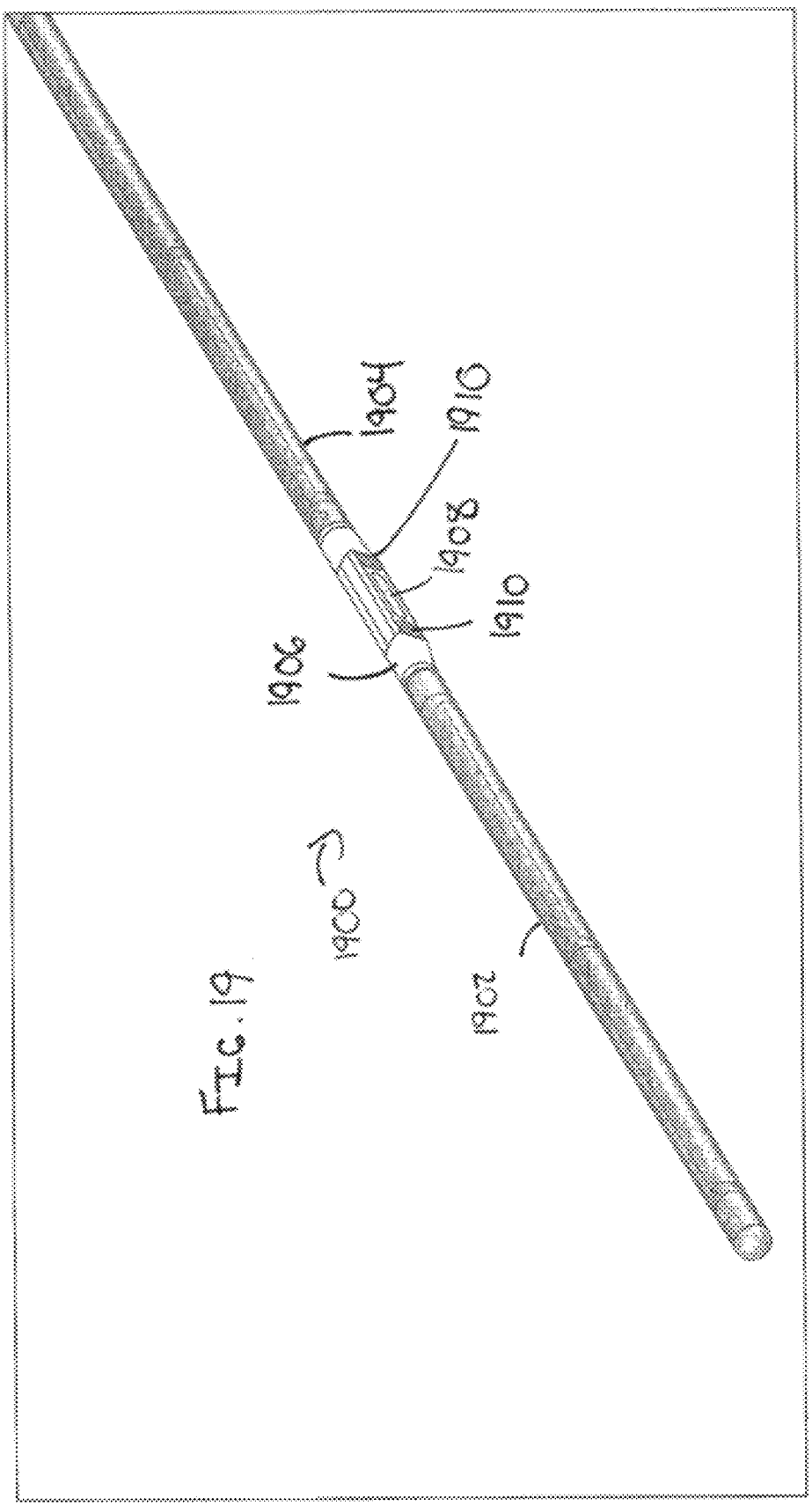

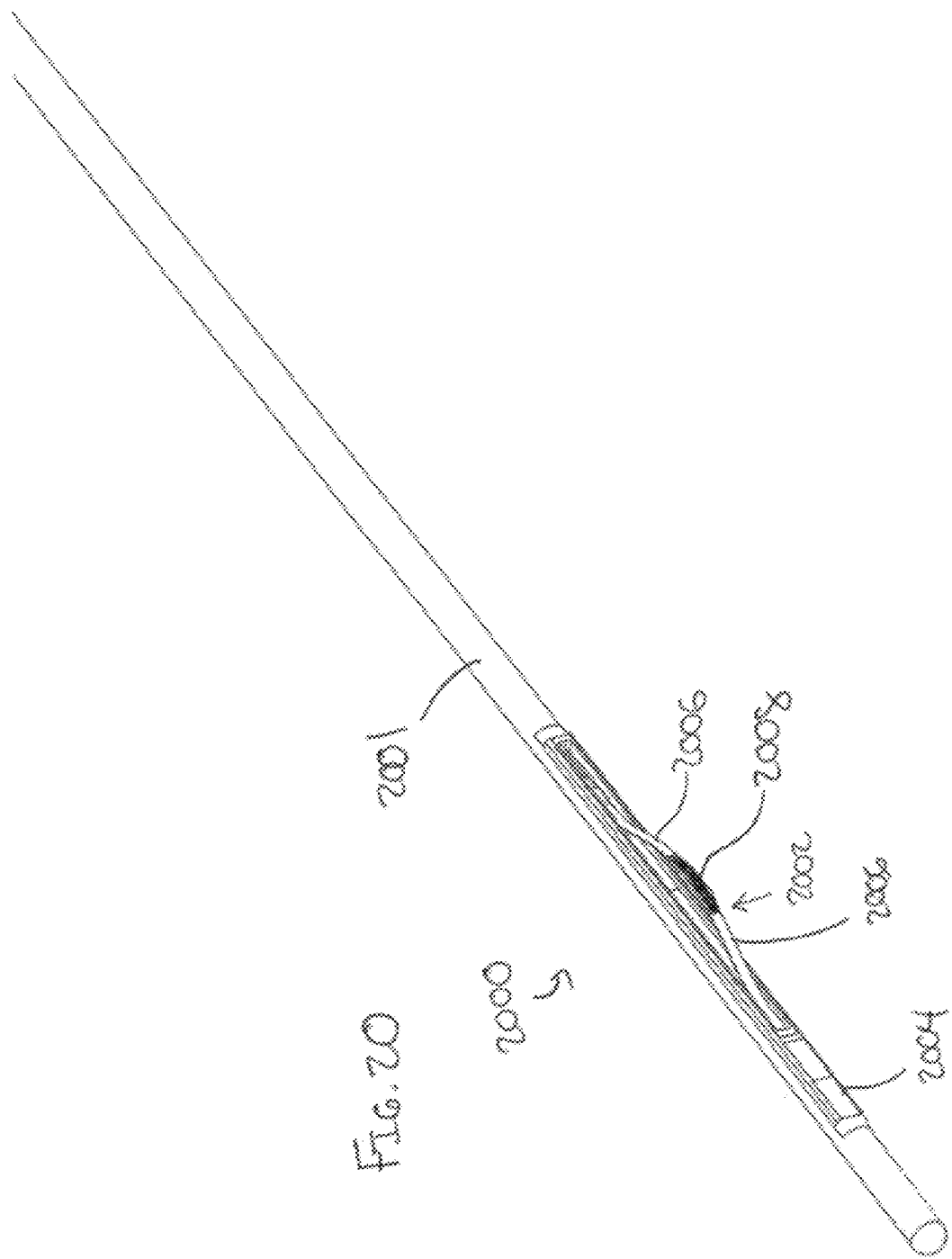

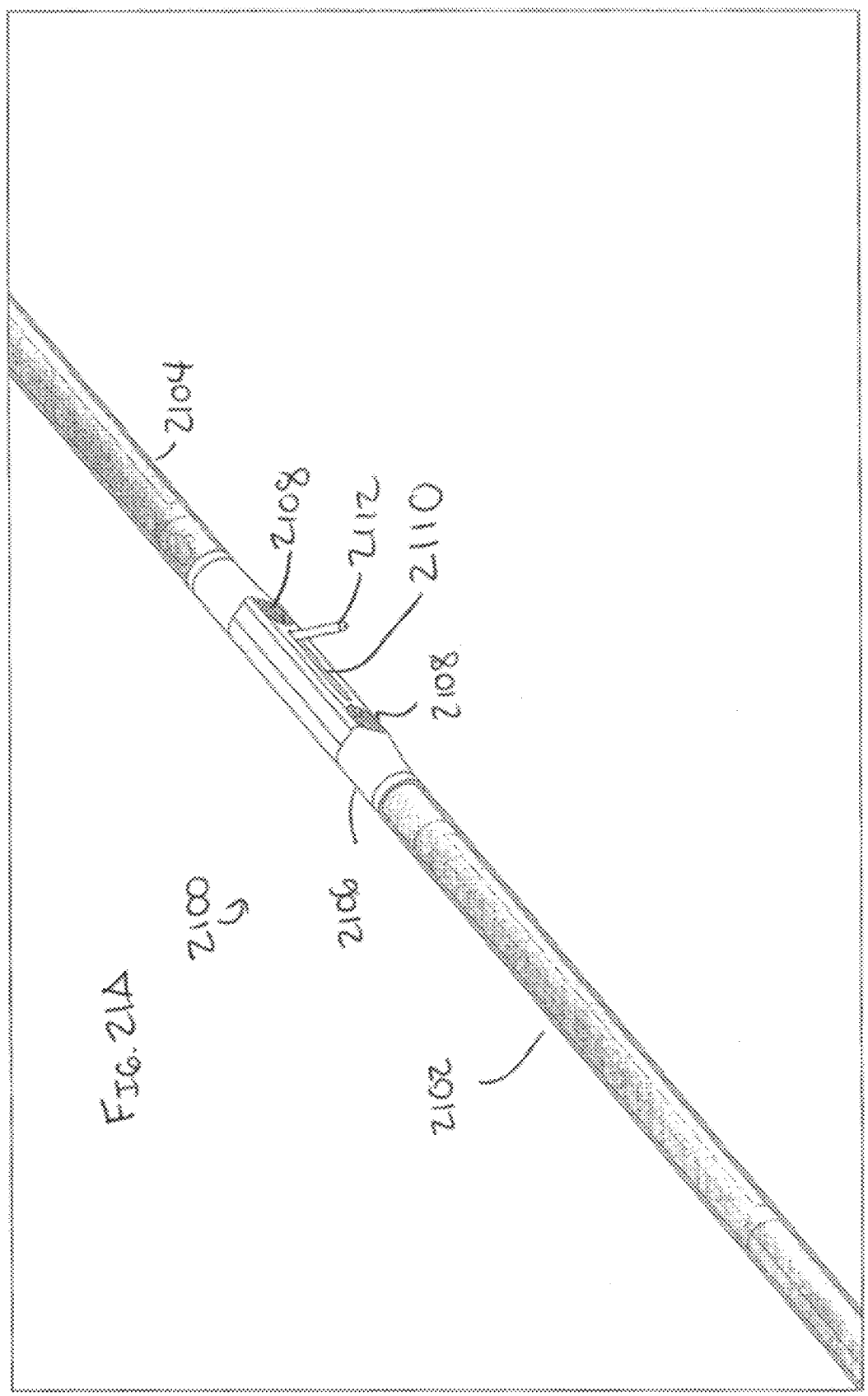

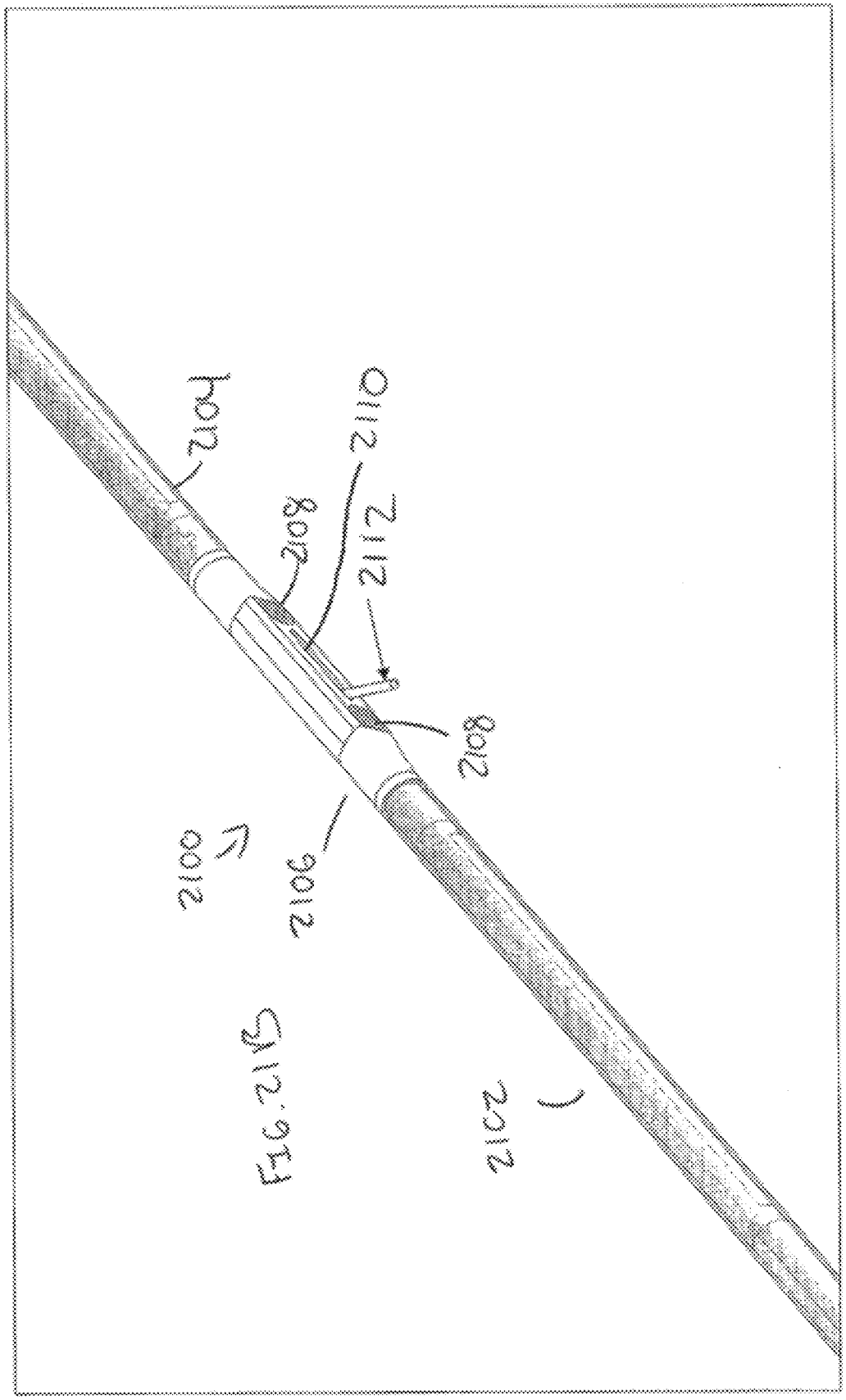

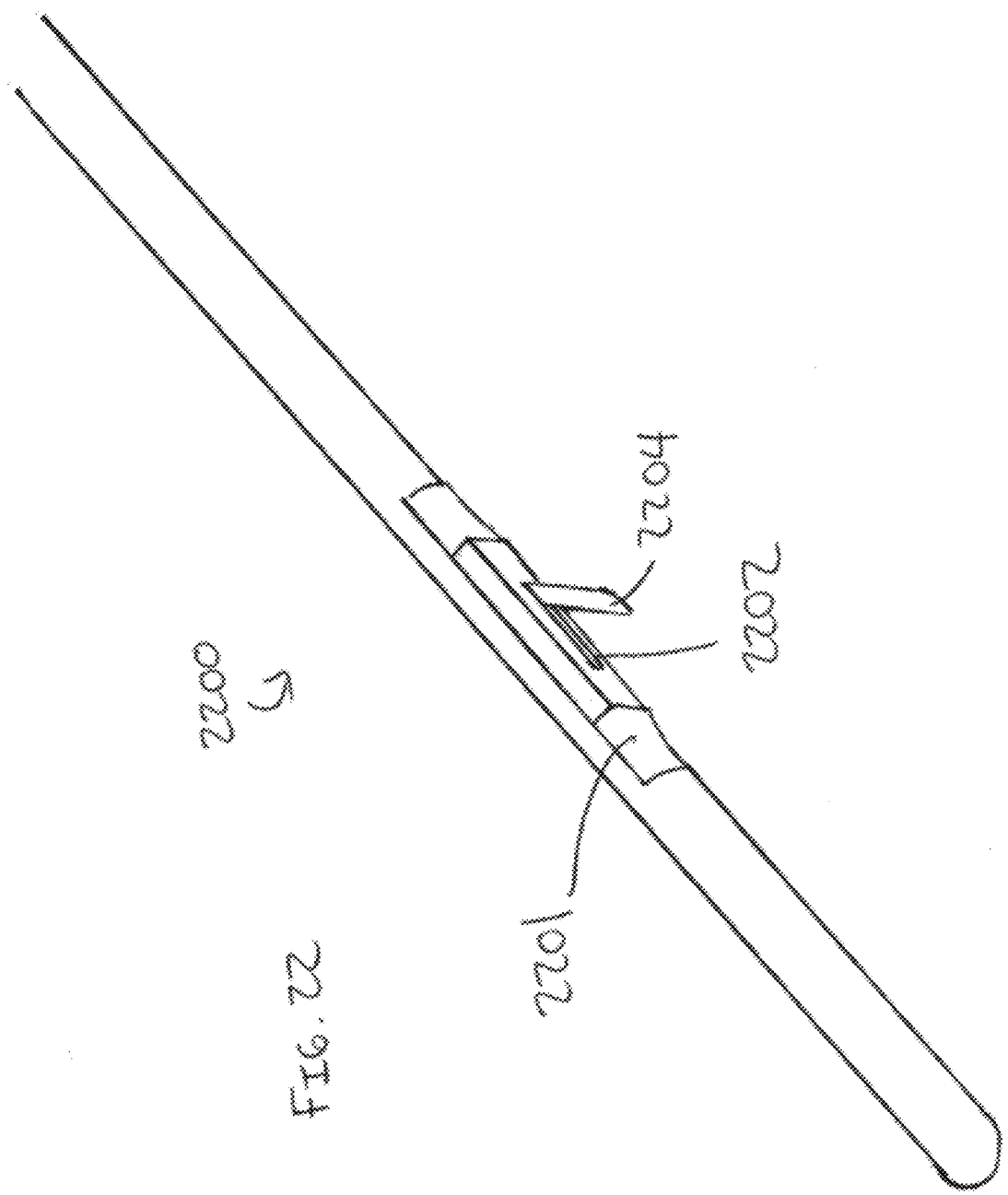

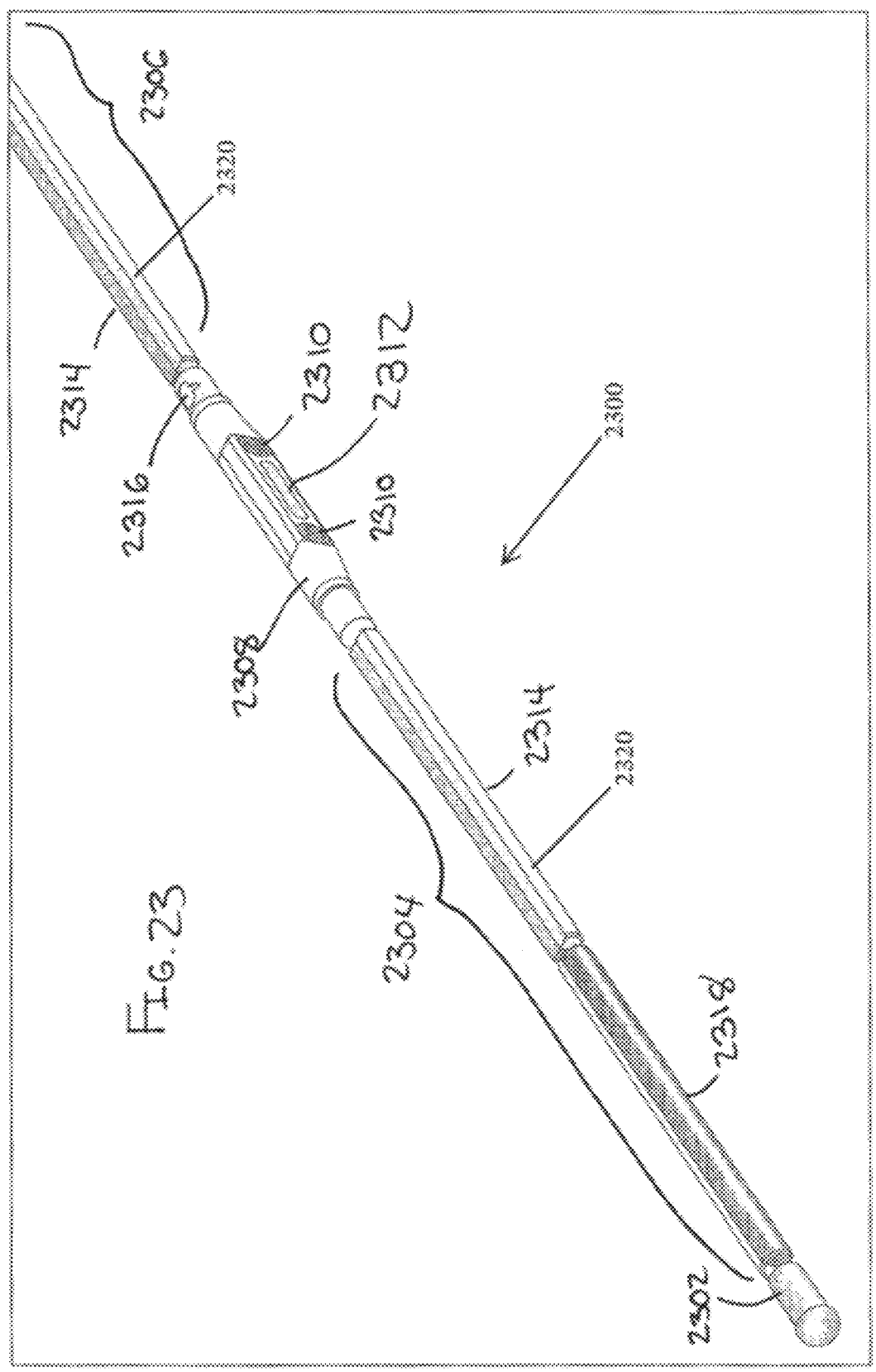

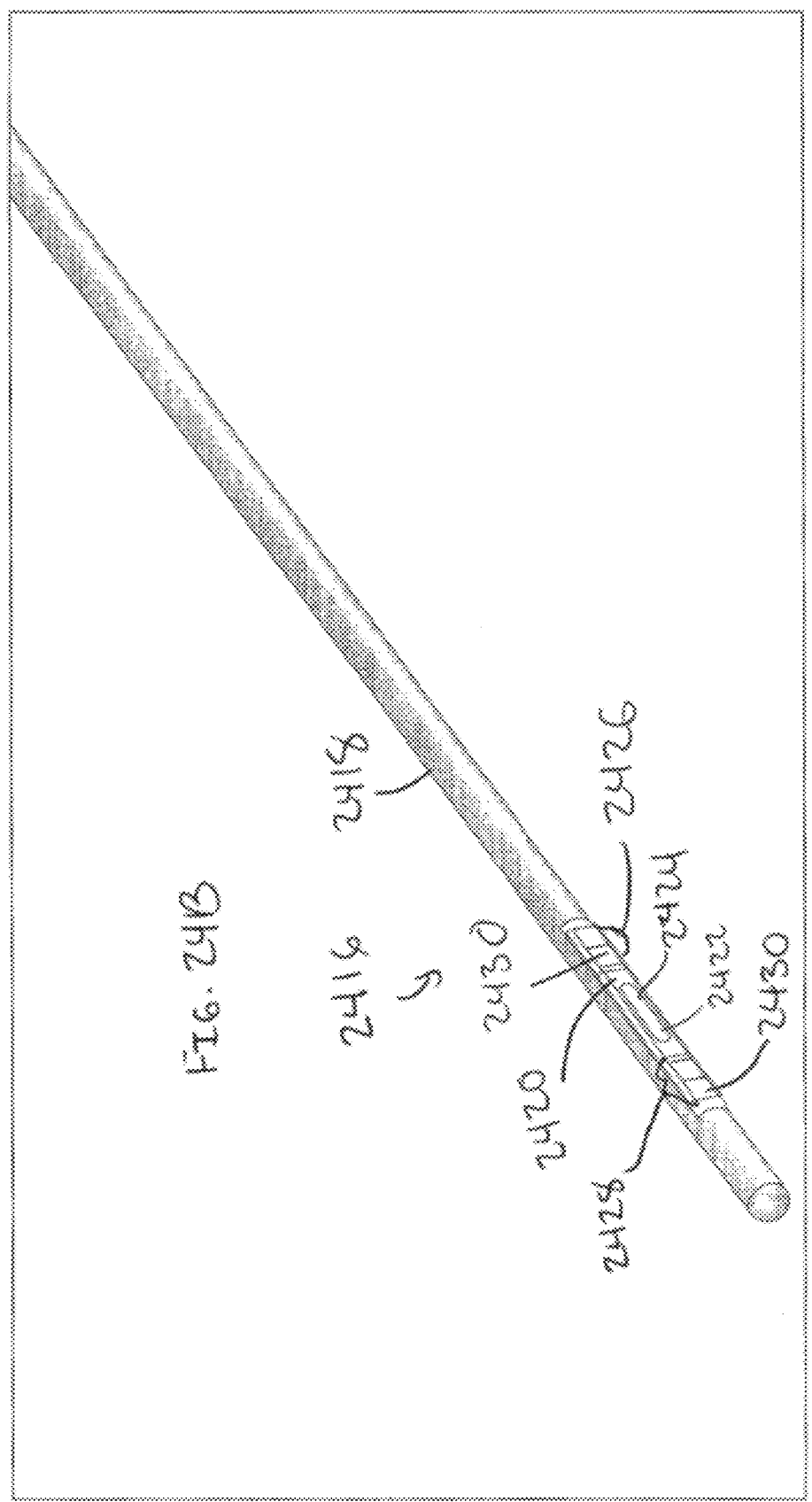

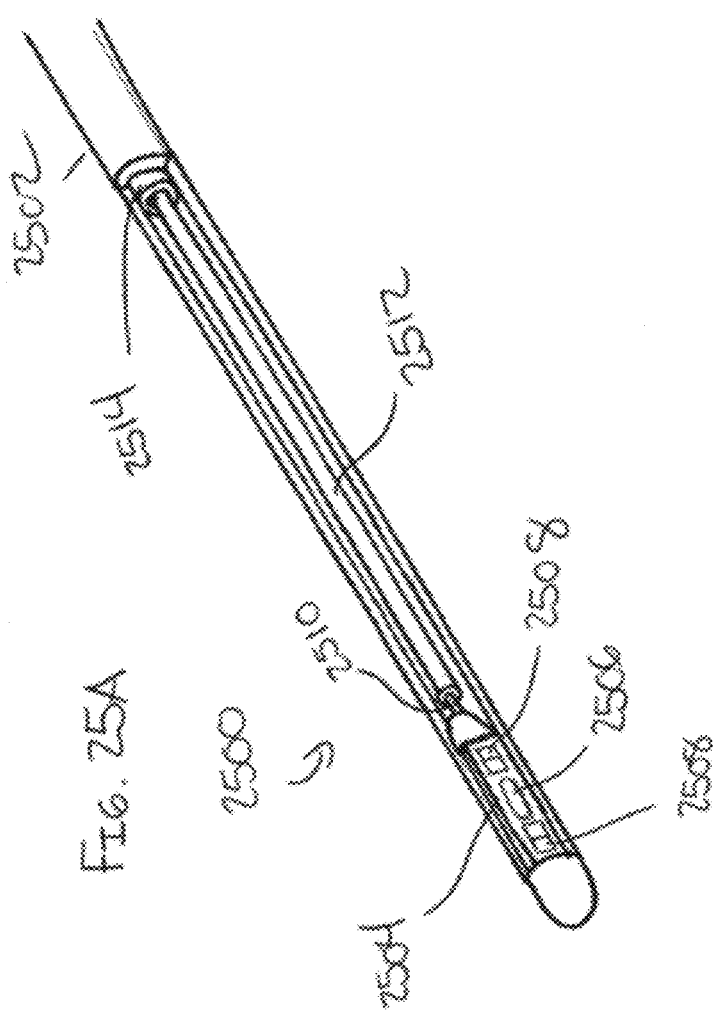

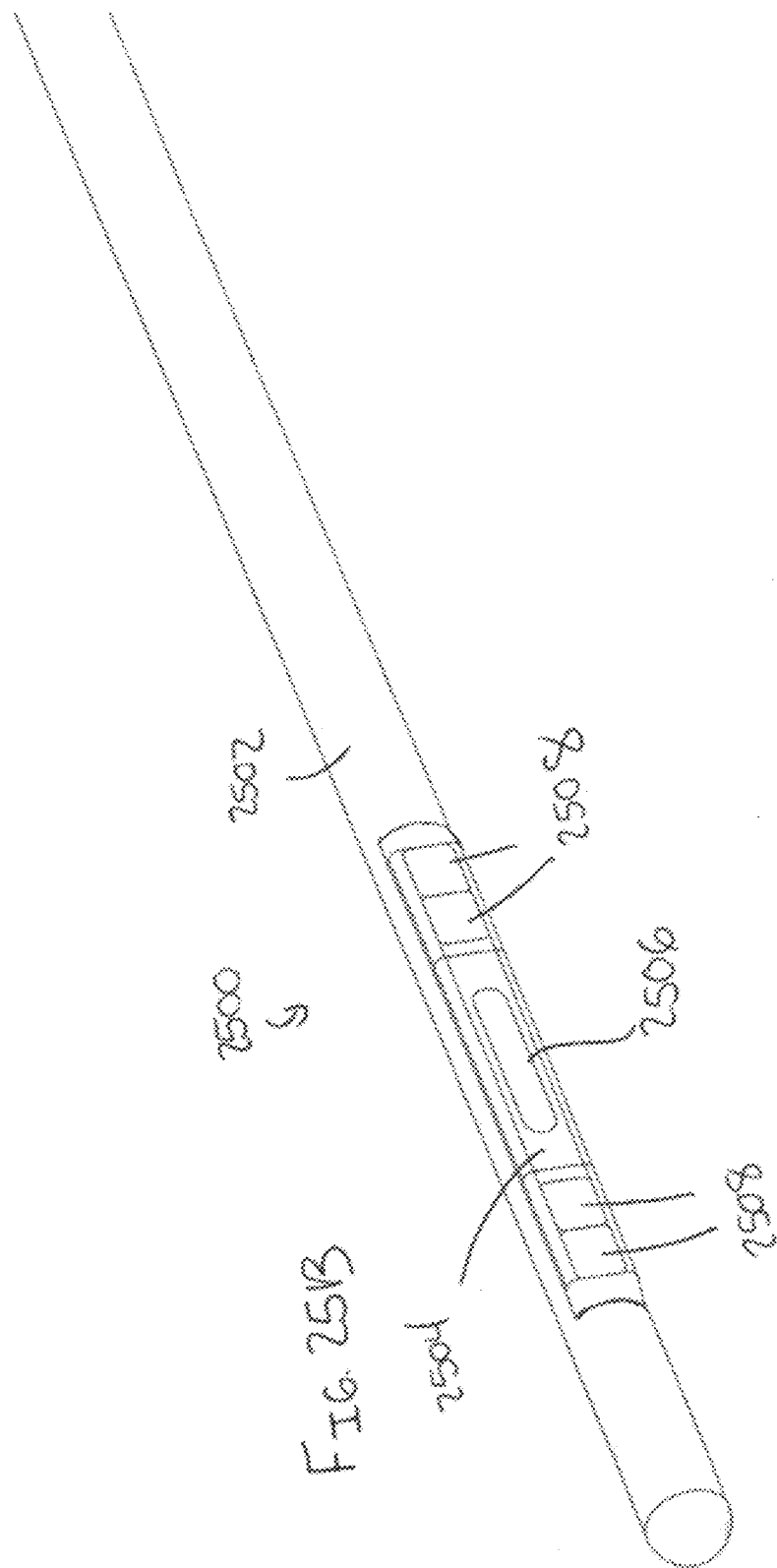

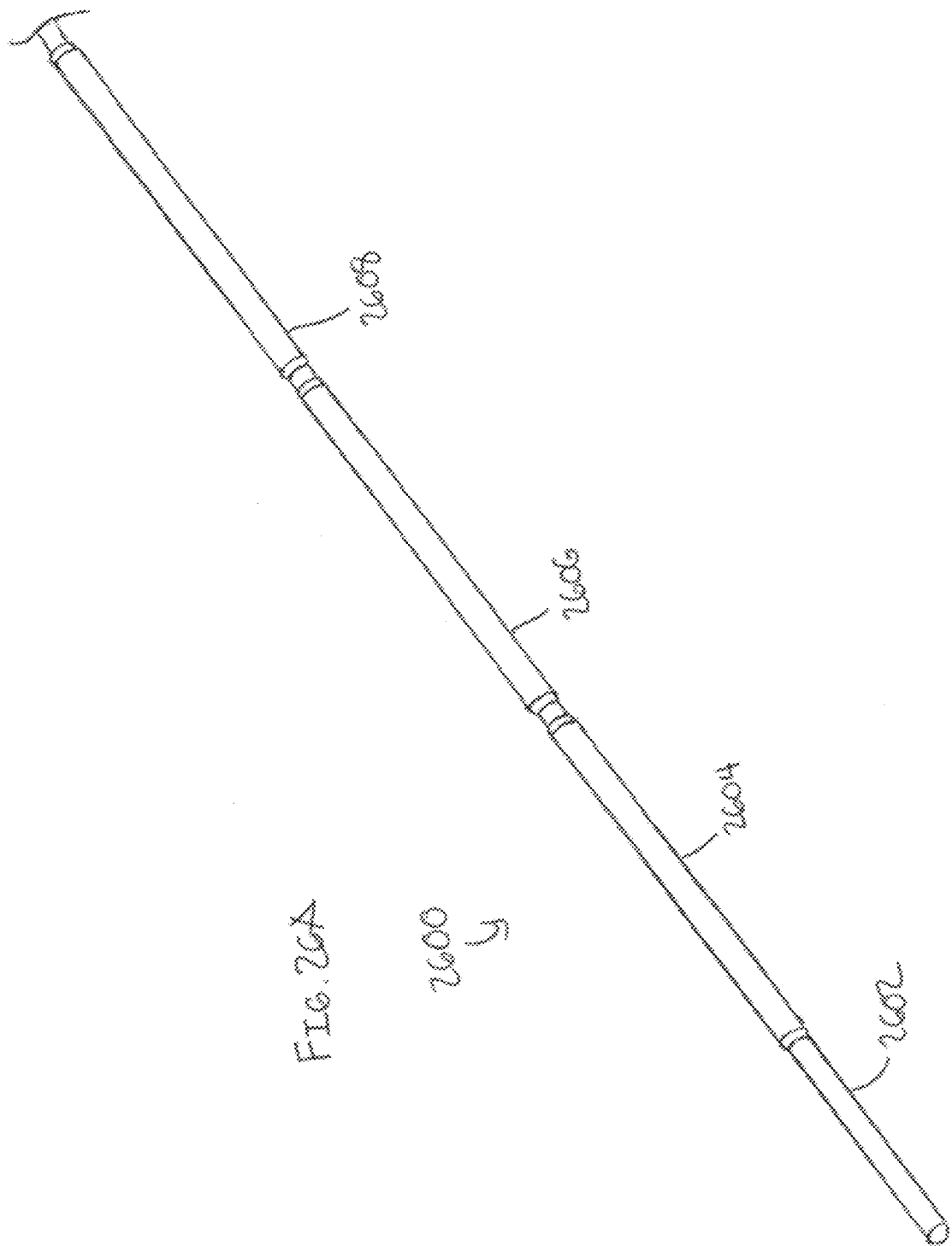

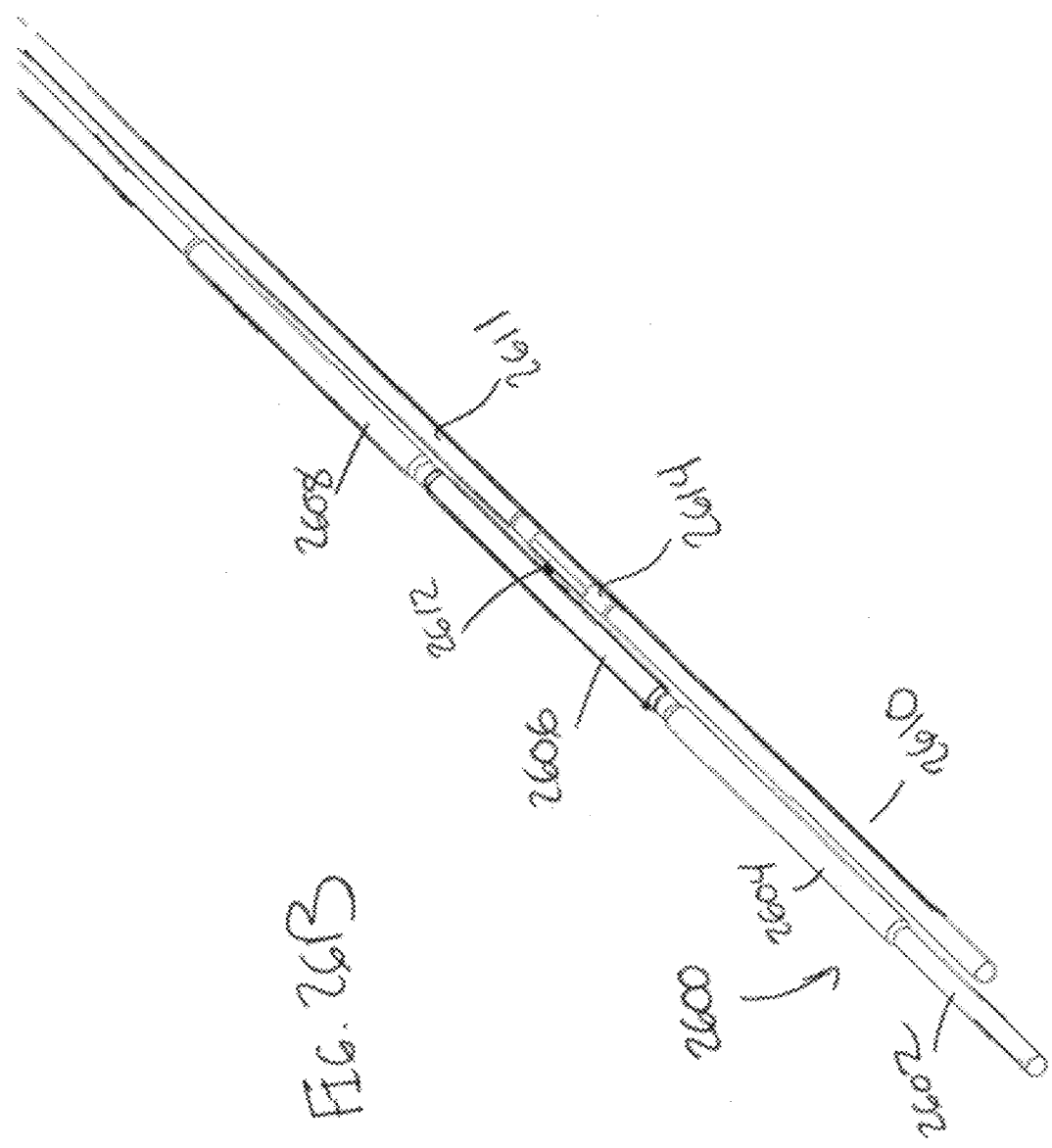

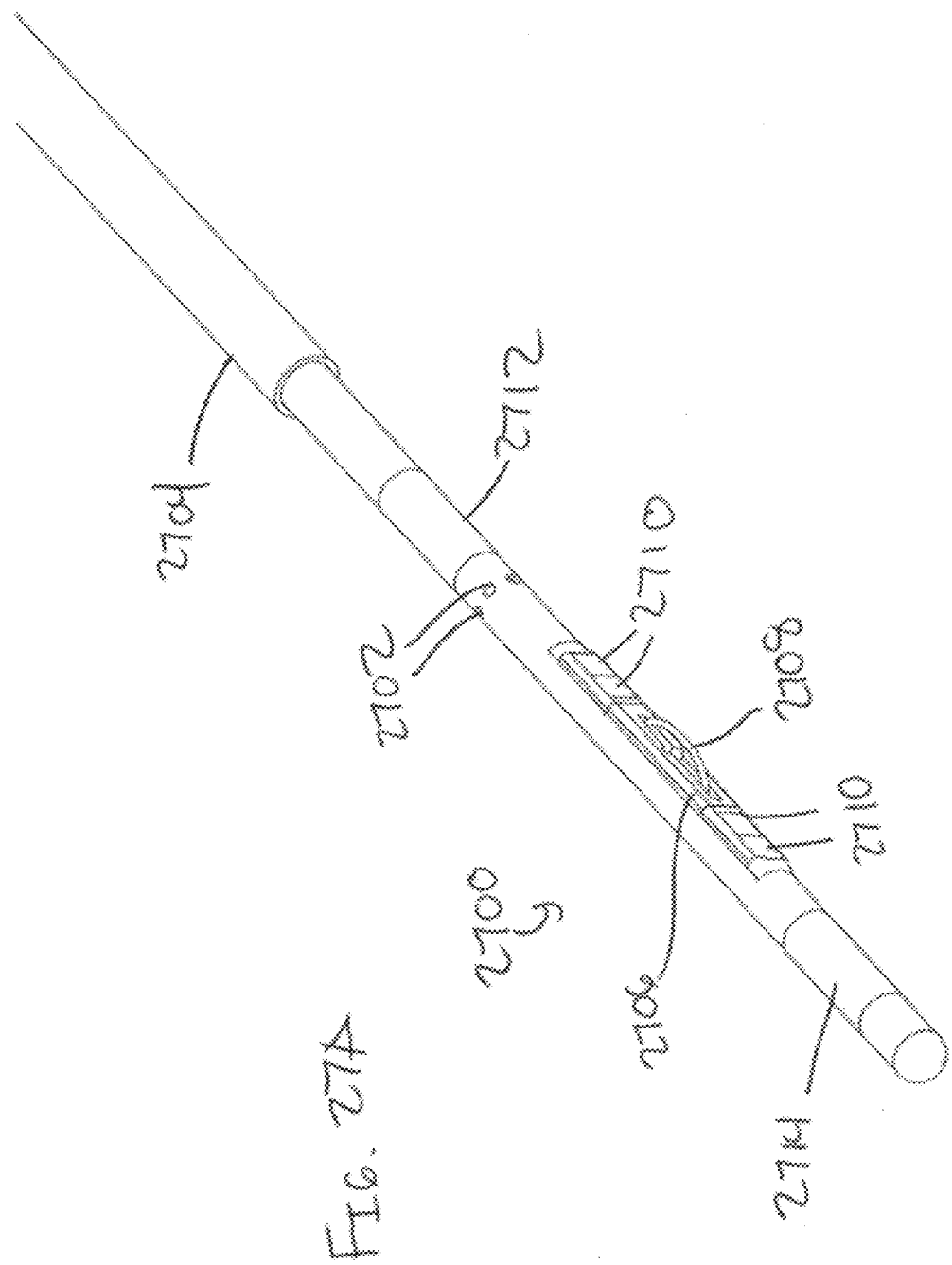

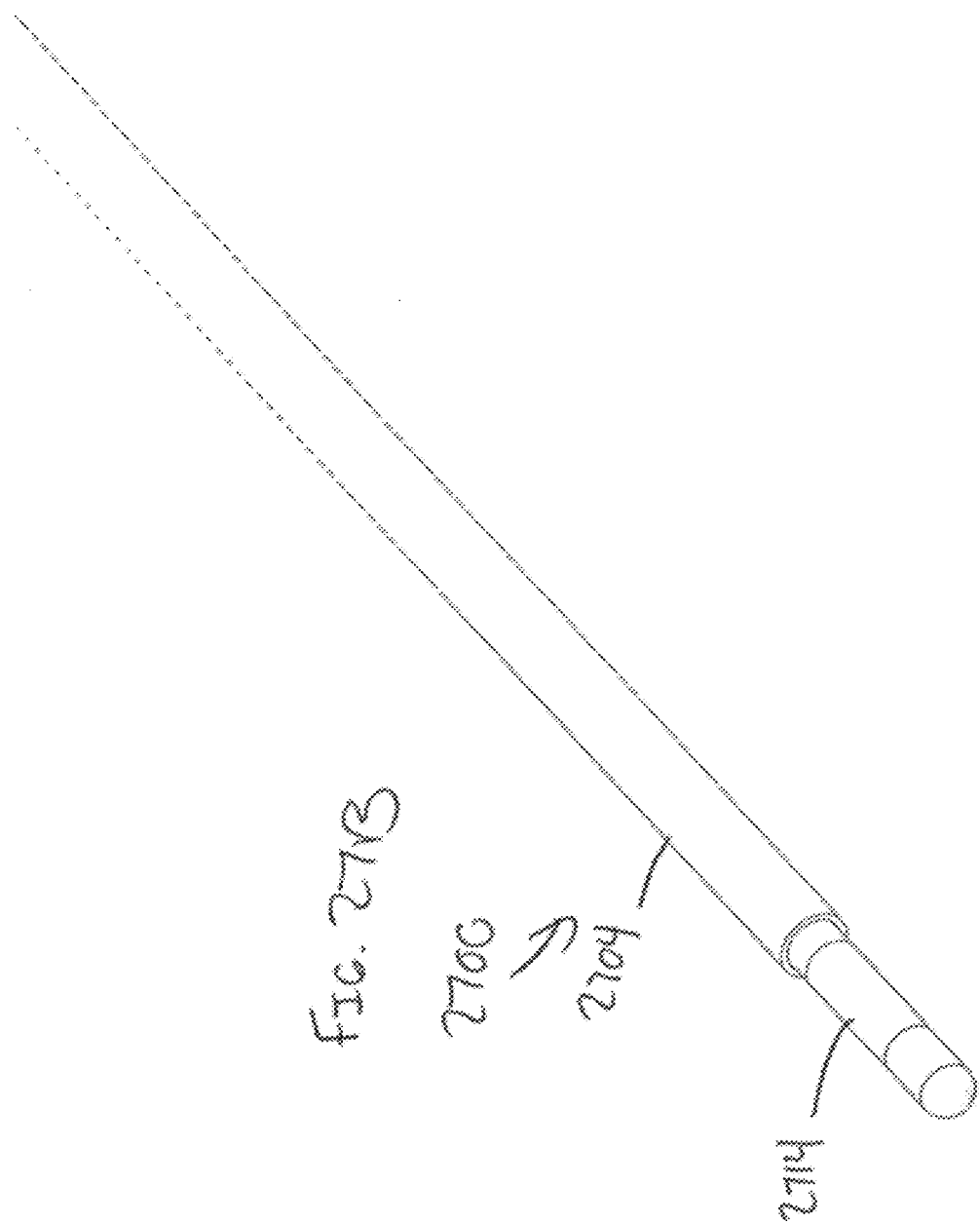

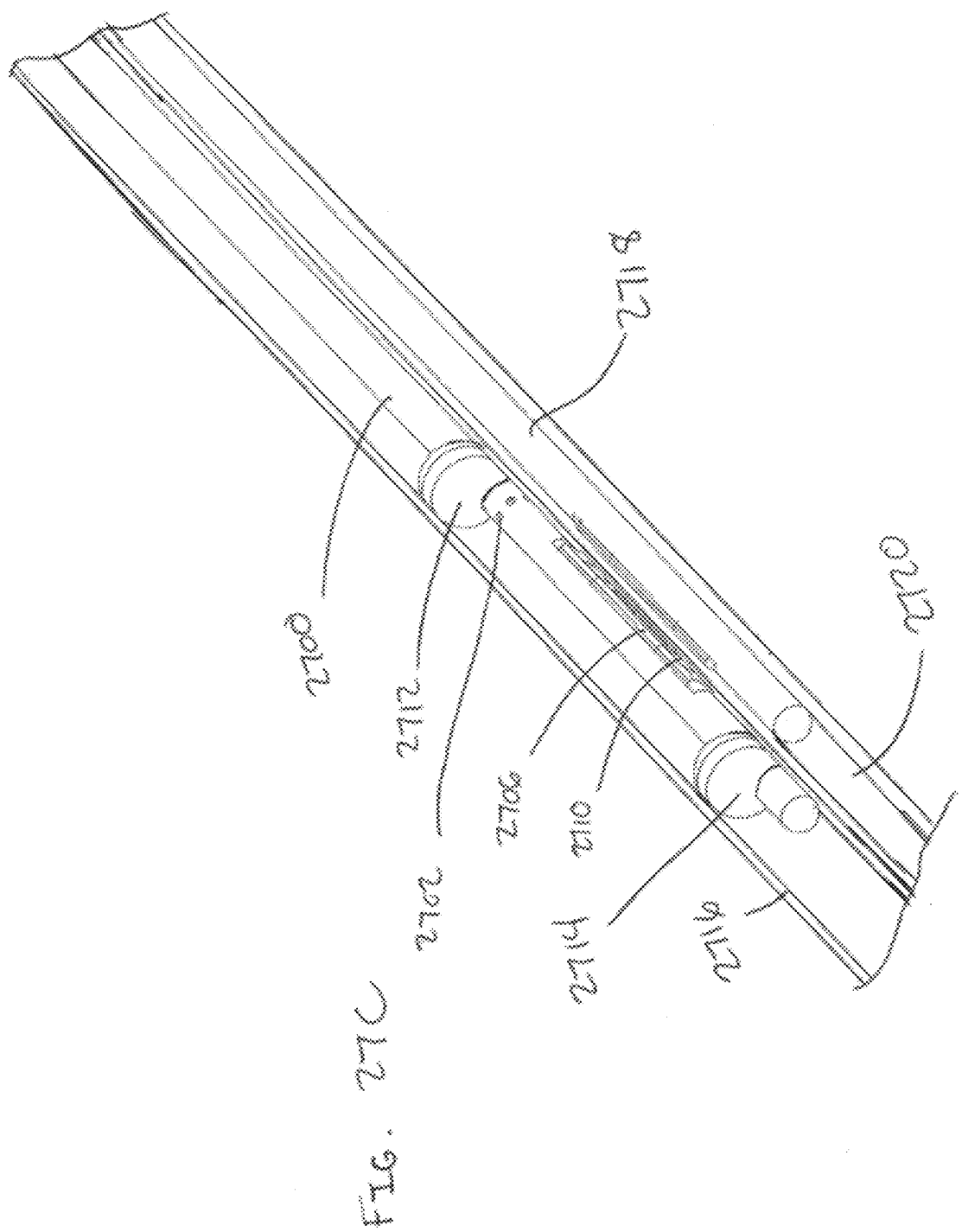

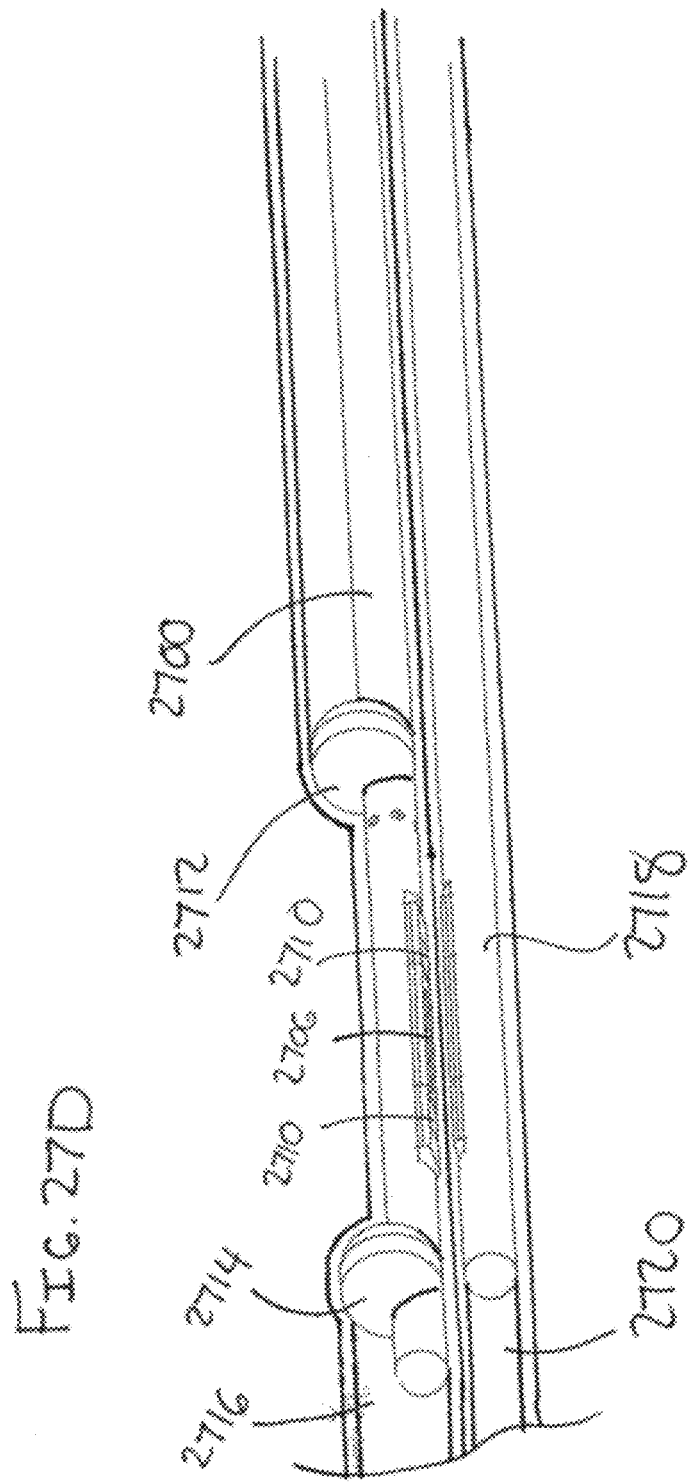

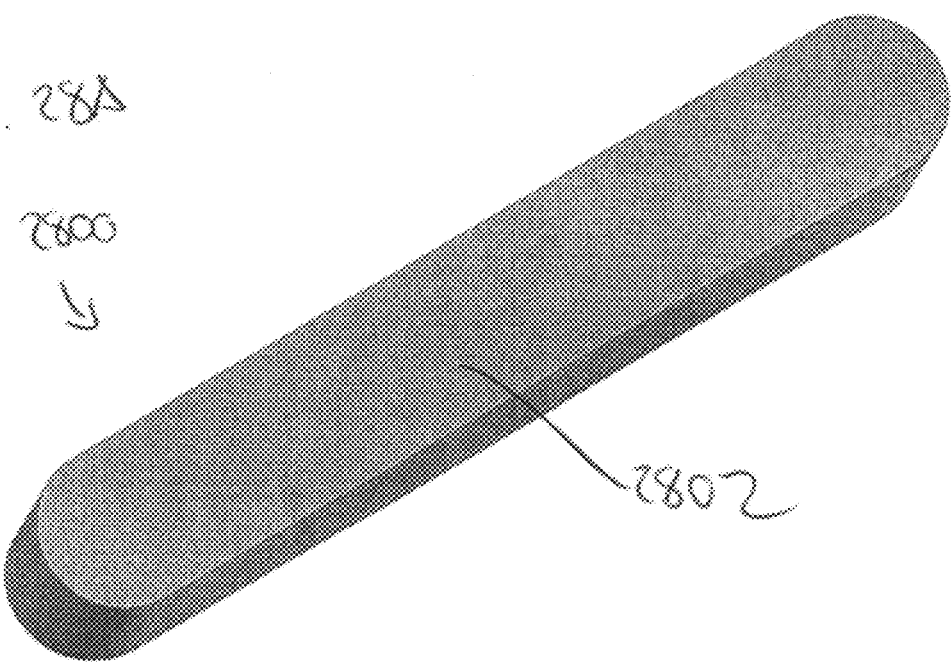
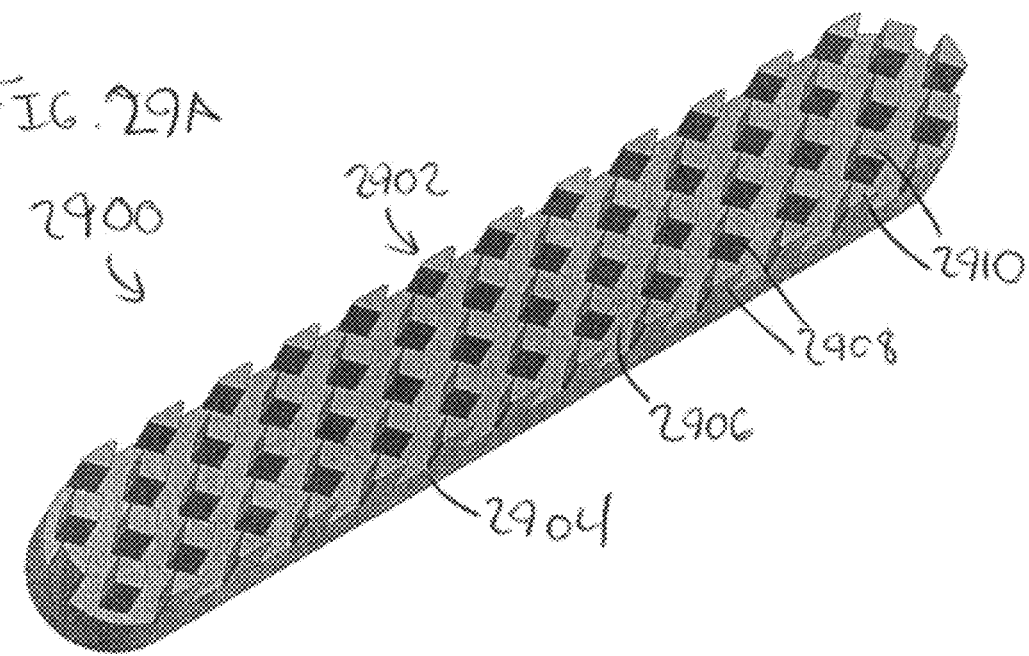

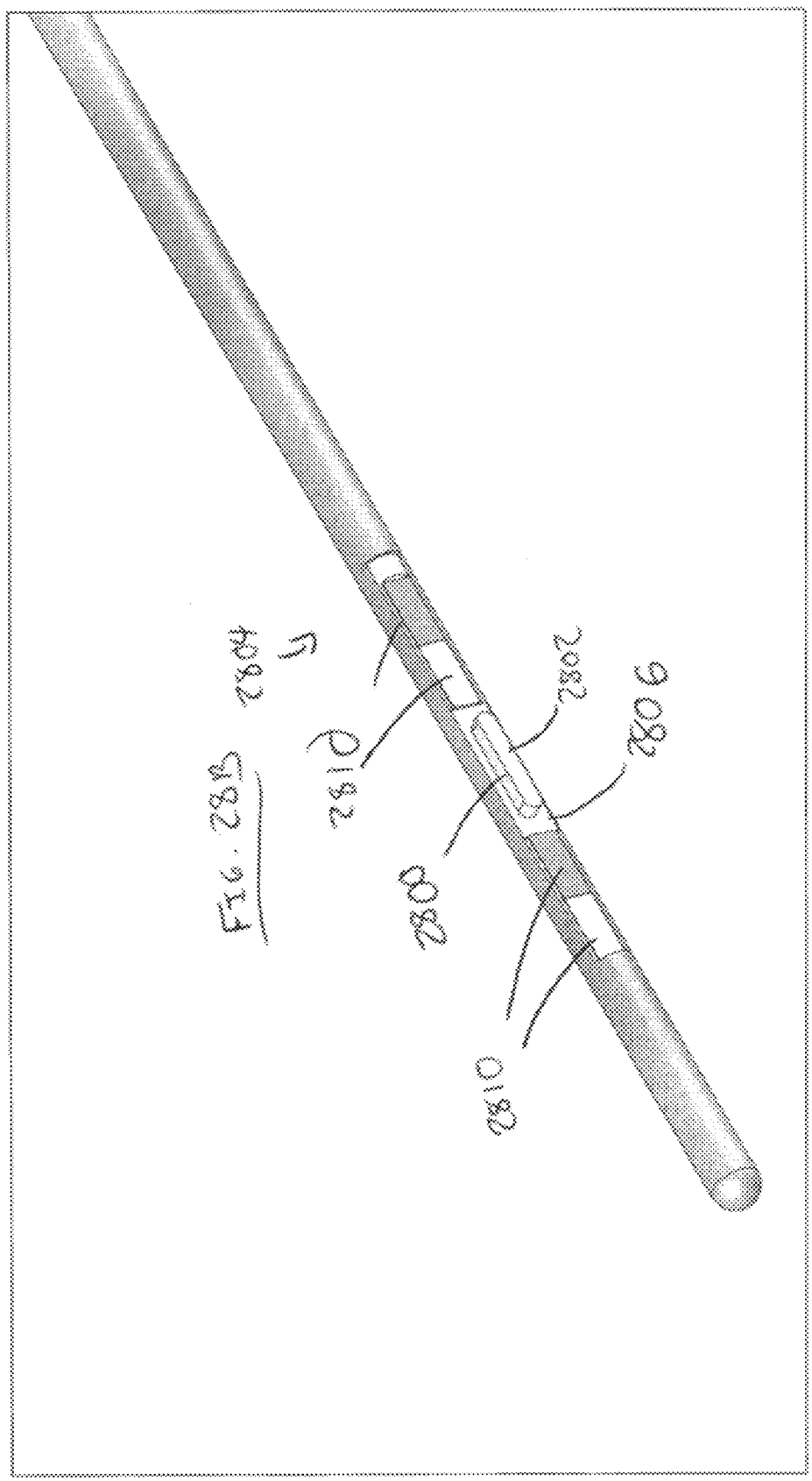

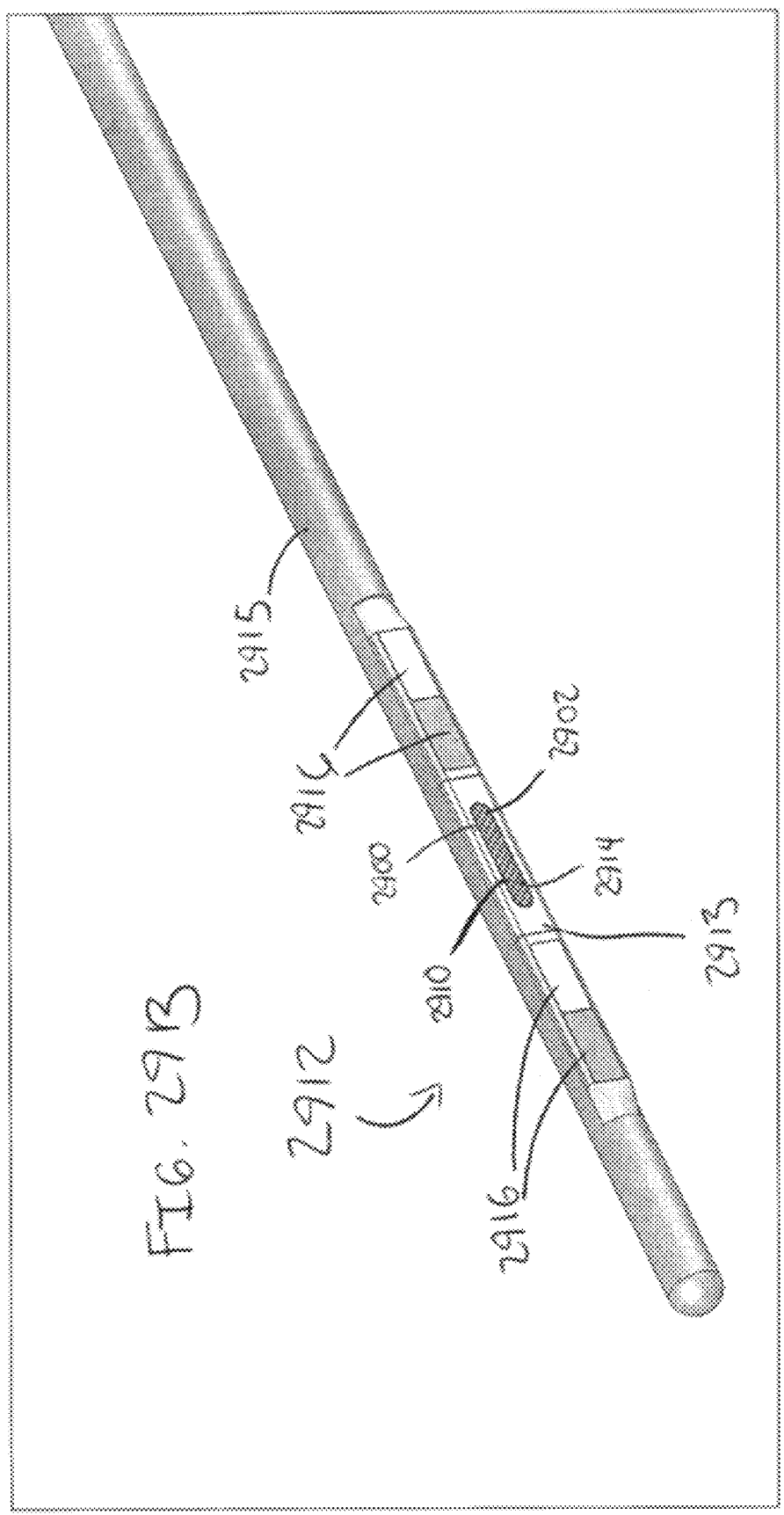

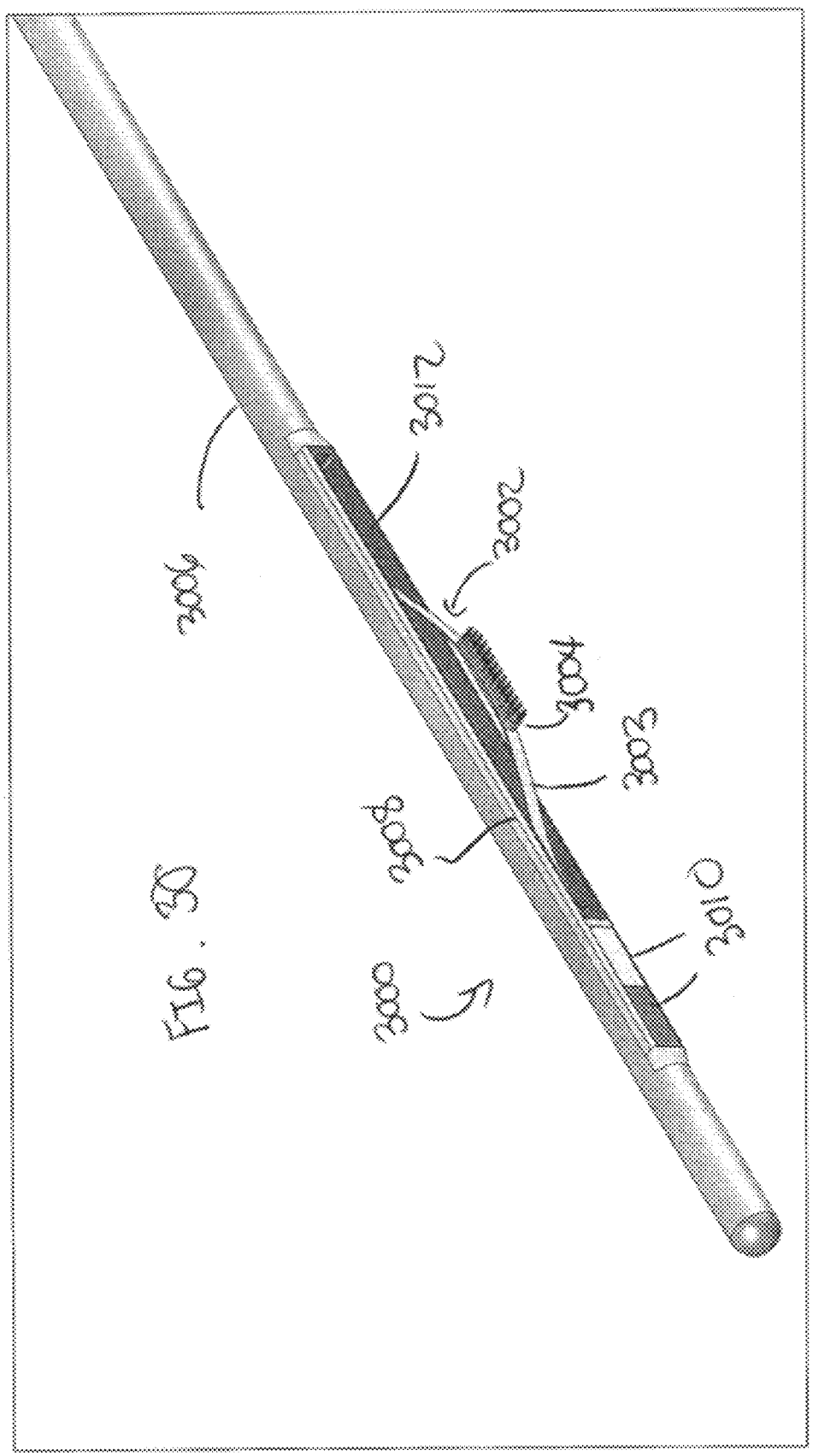

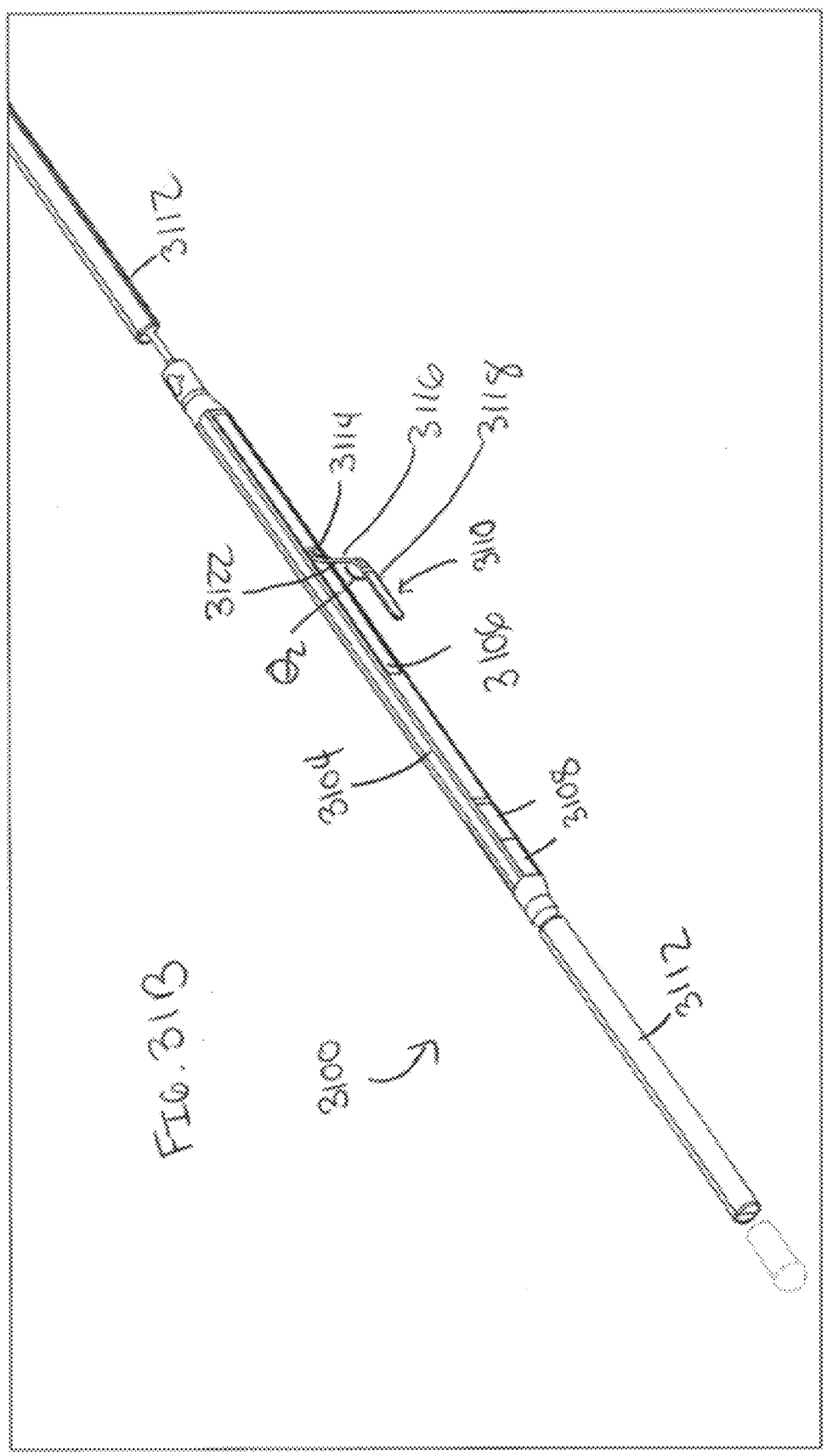

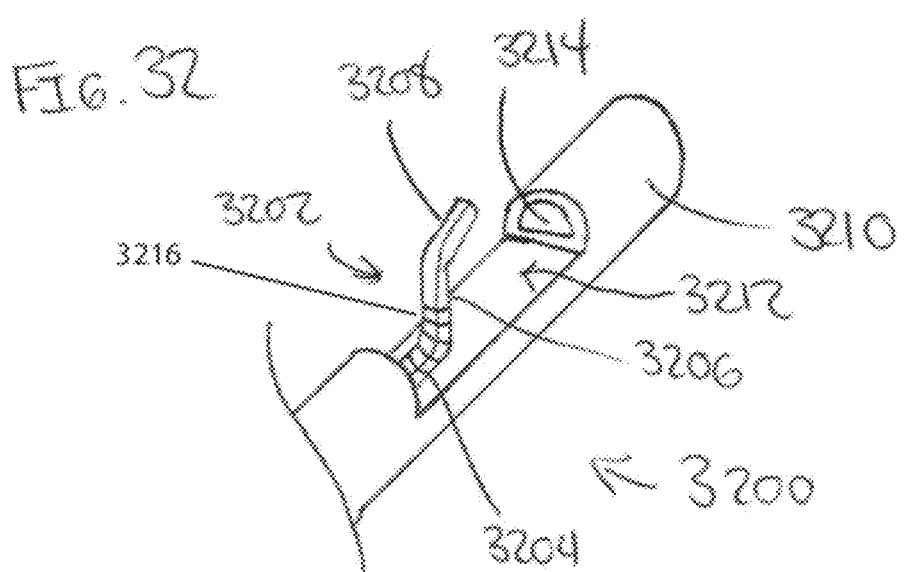

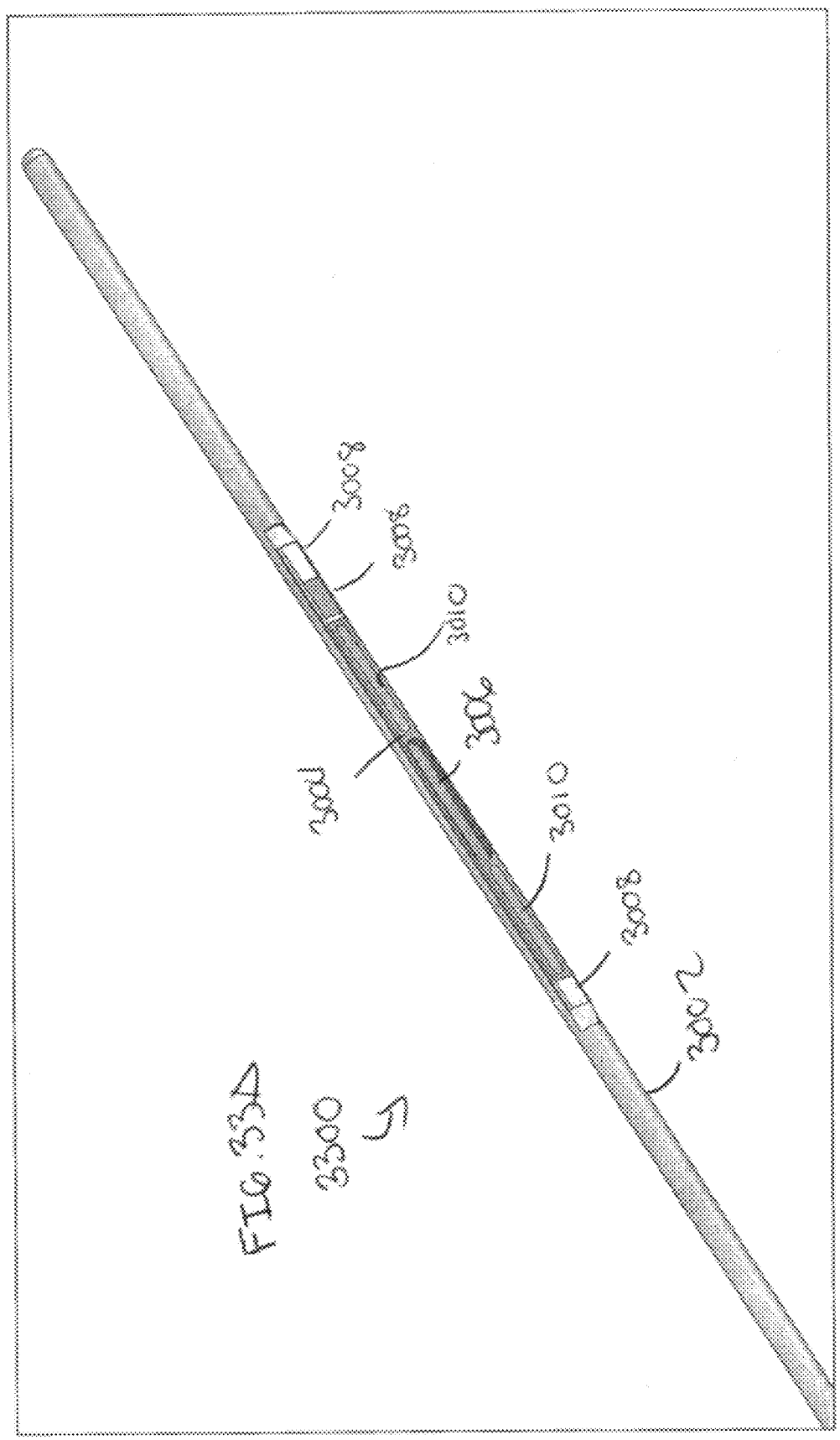

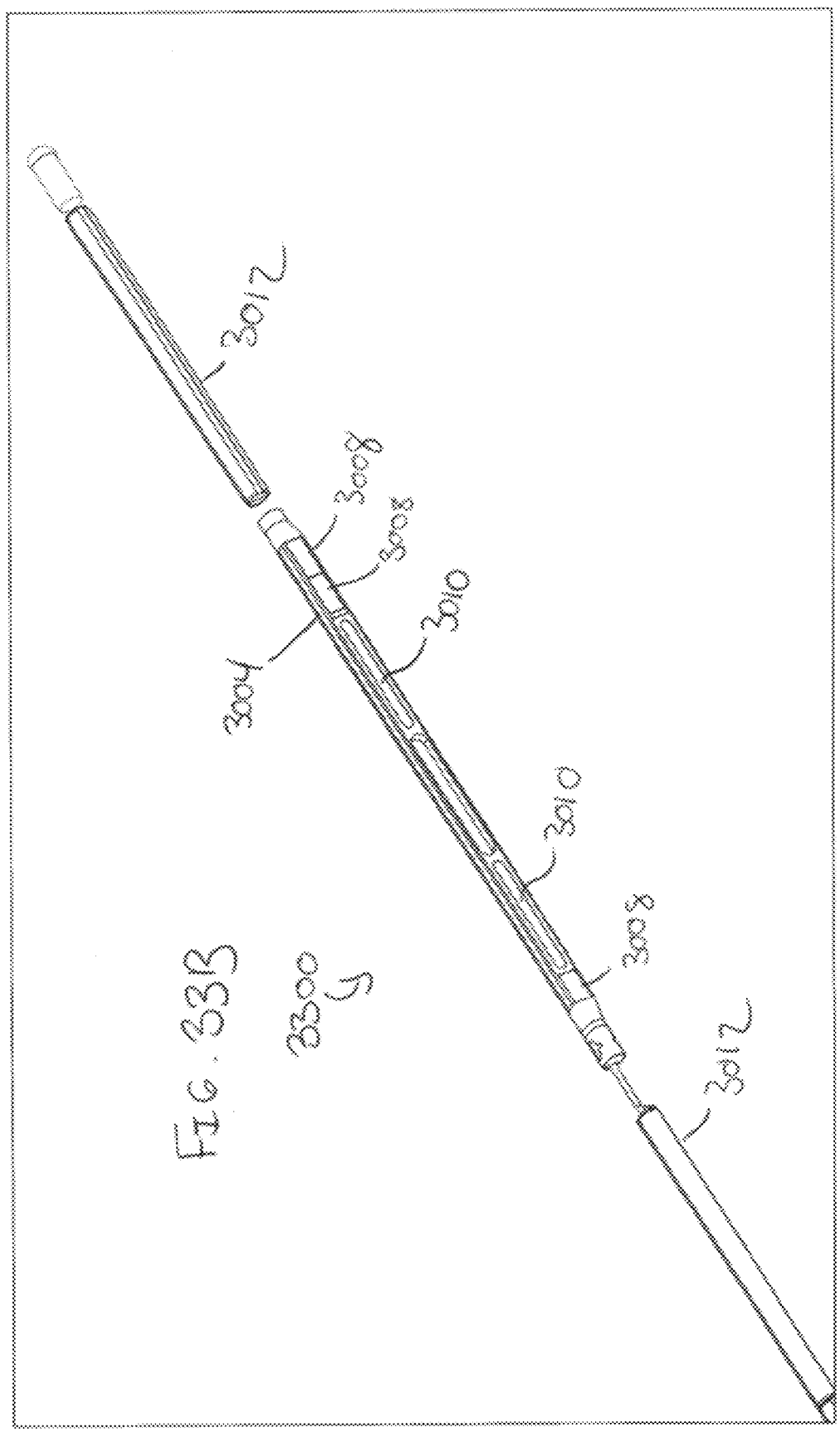

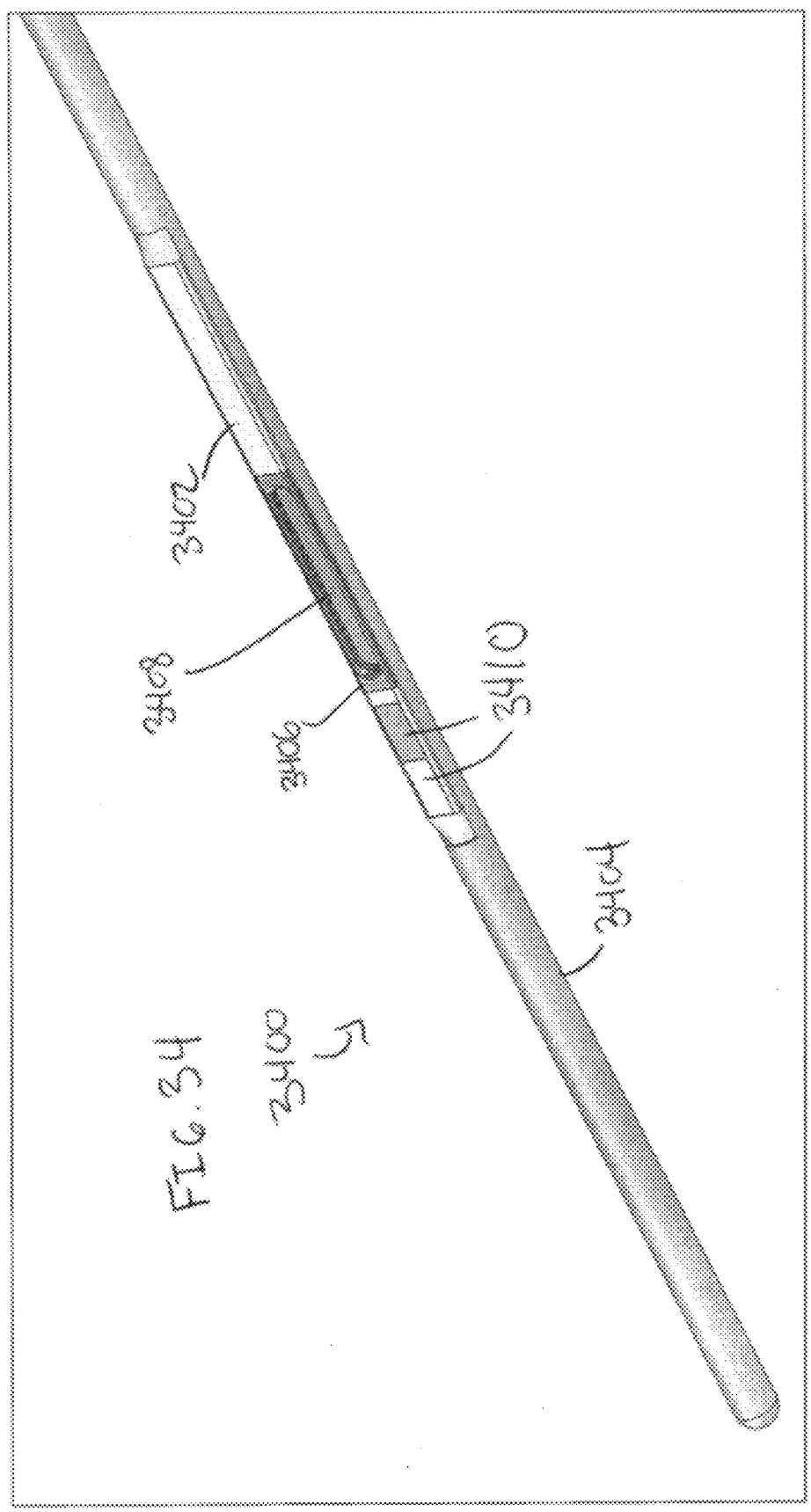

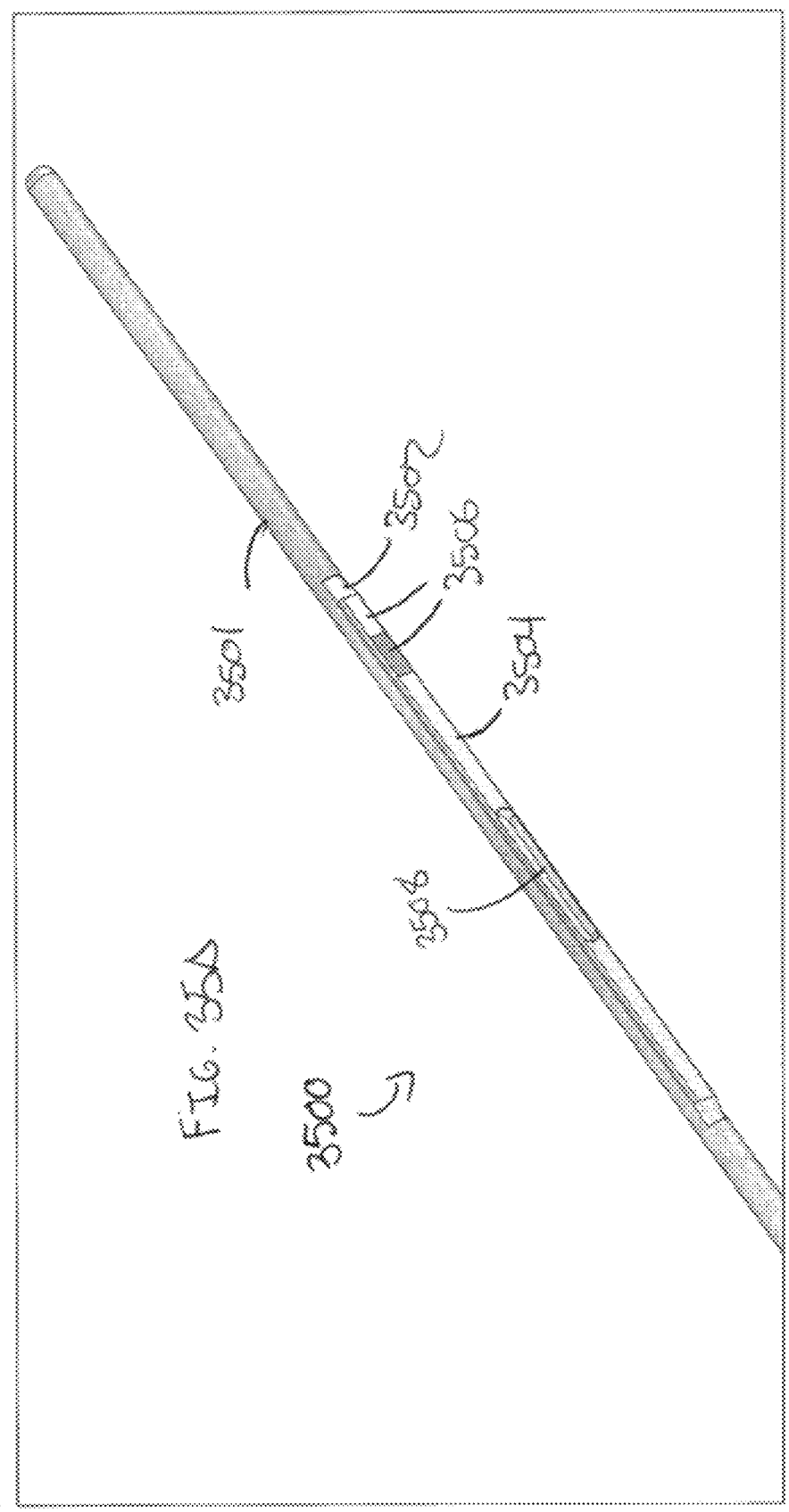

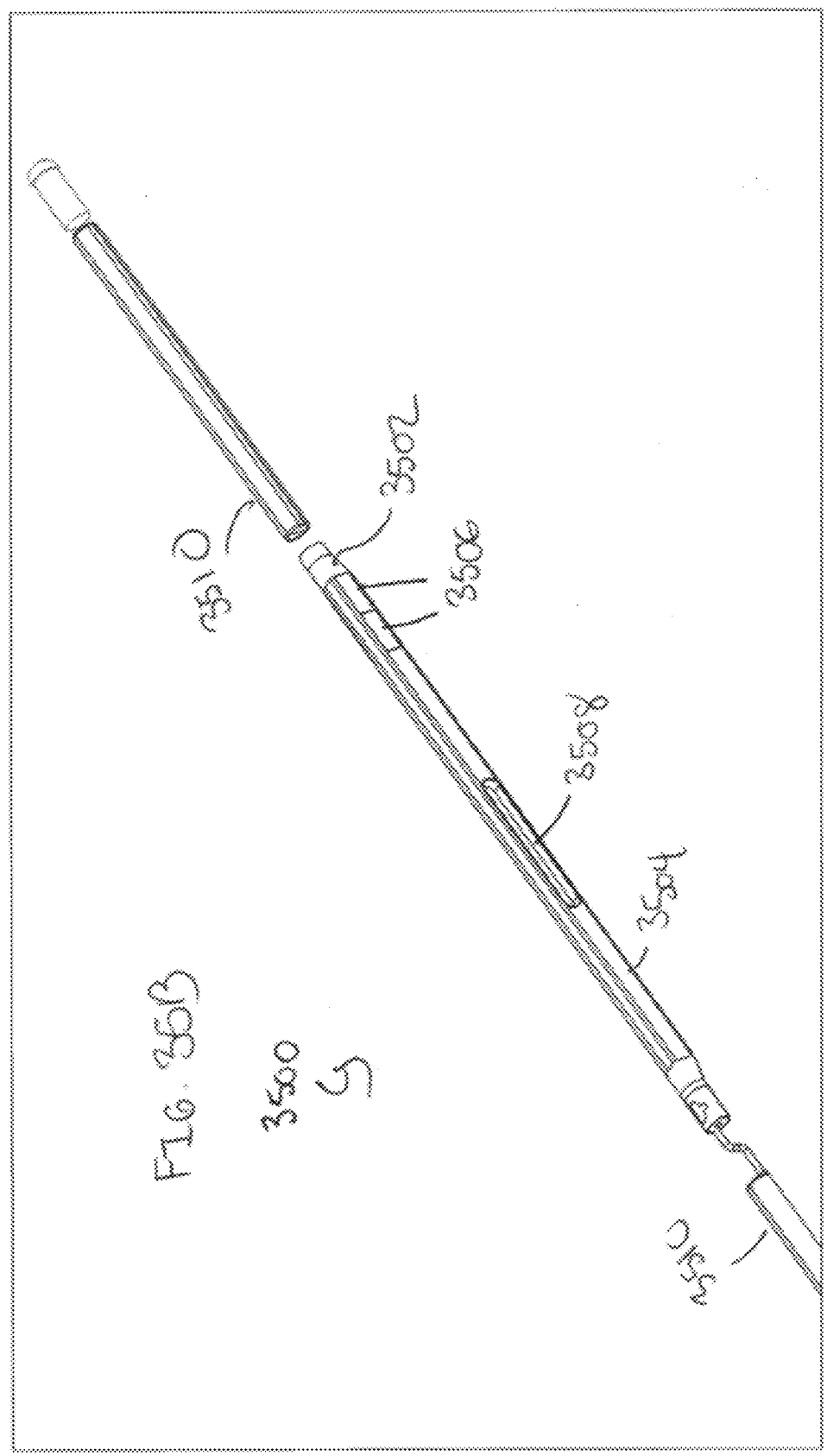

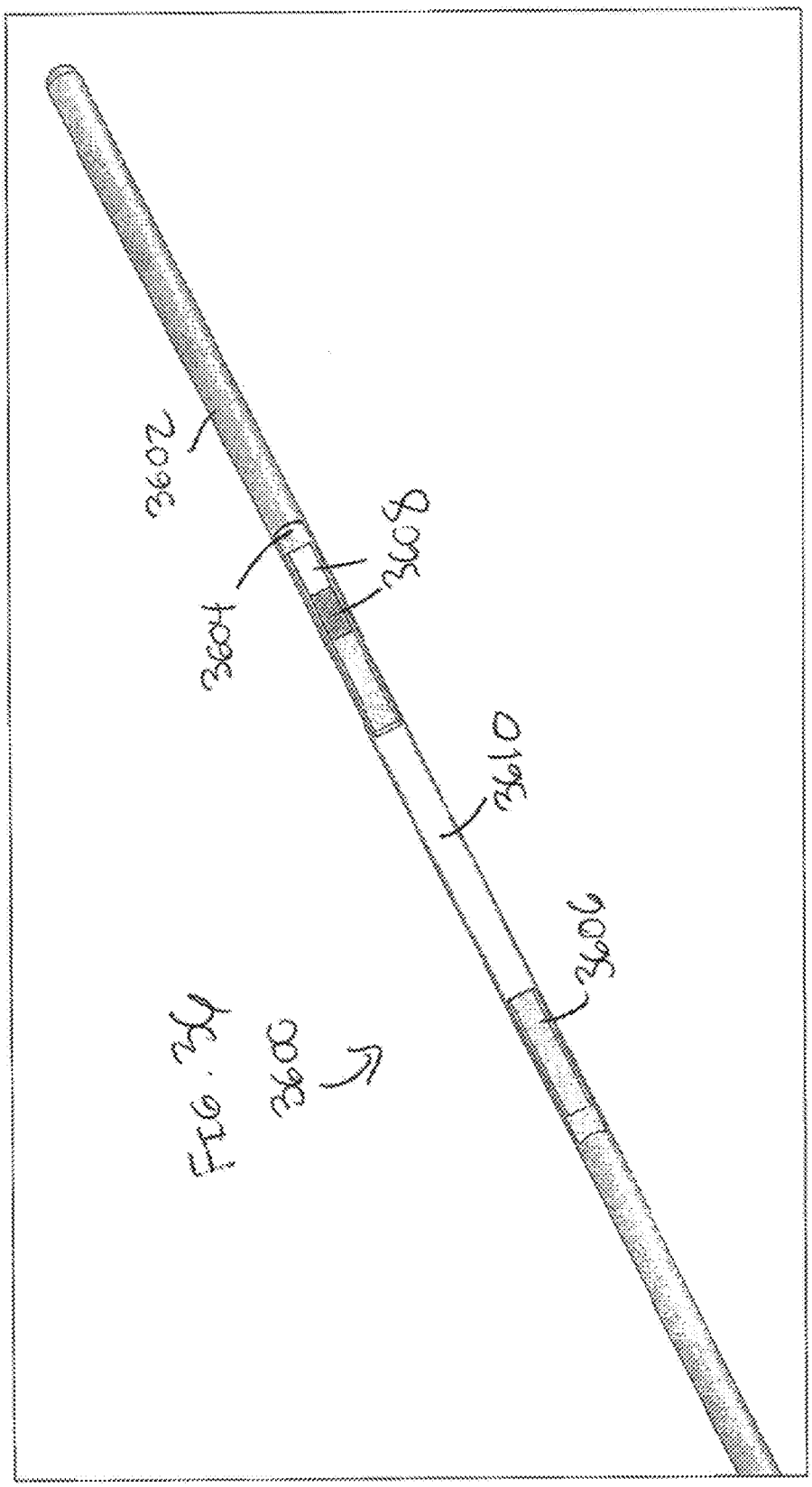

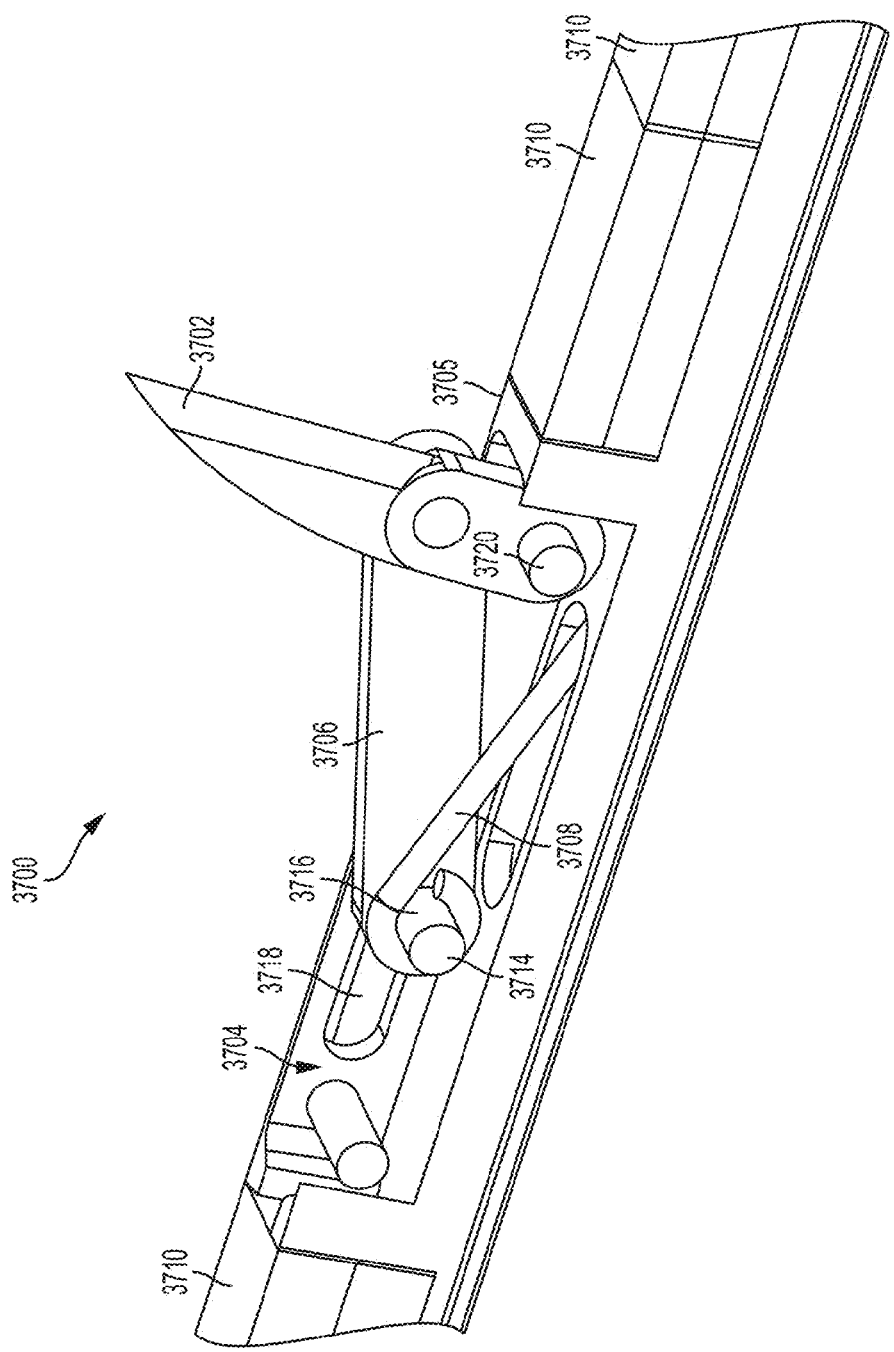

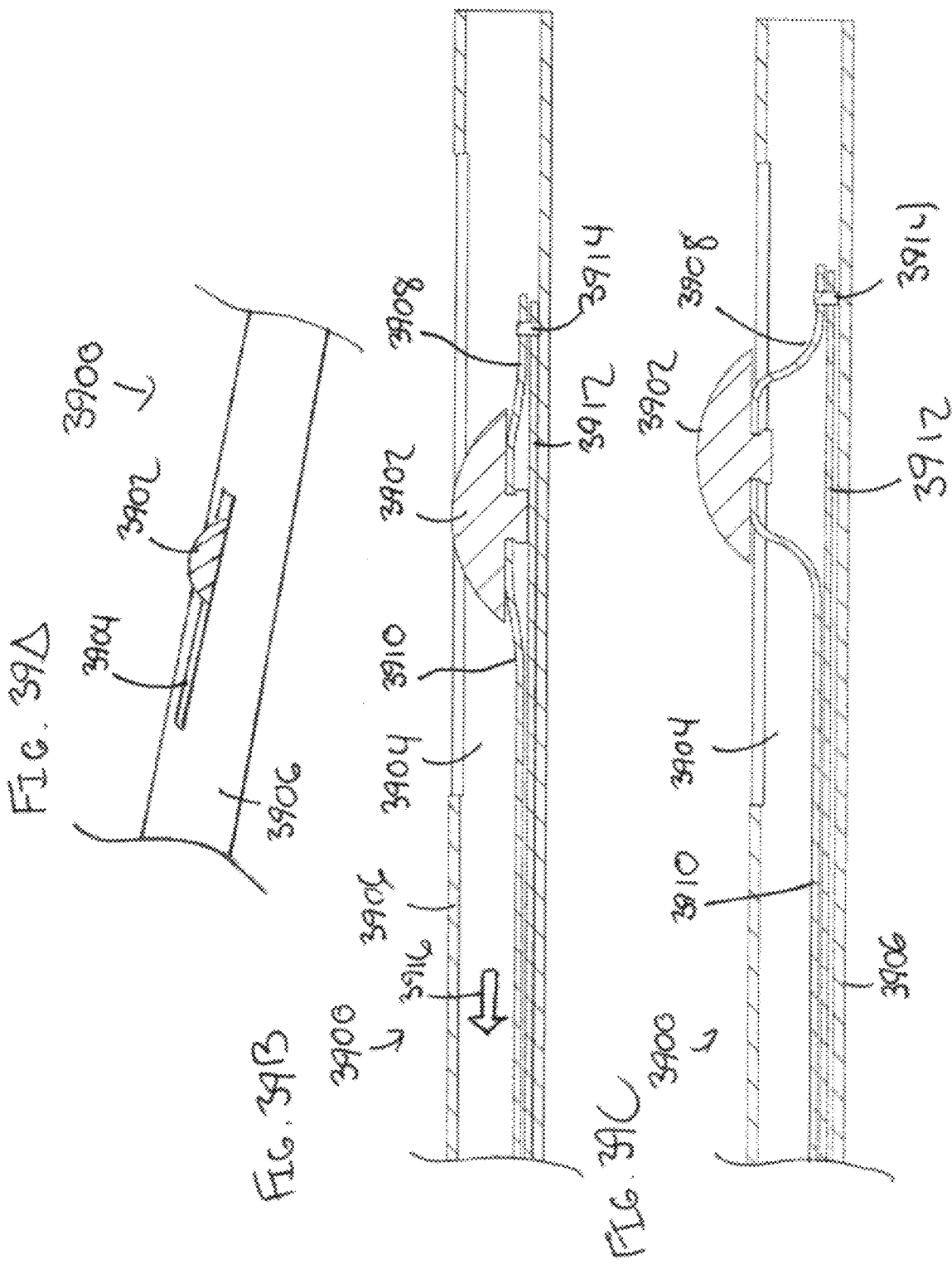

DEVICES AND METHODS FOR FORMING A FISTULA

CROSS-REFERENCE TO RELATED APPLICATIONS

This application claims priority to U.S. Provisional Application Ser. No. 61/414,357, filed on Nov. 16, 2010, which is hereby incorporated by reference in its entirety.

FIELD

The current invention relates to devices and methods for forming a fistula. The devices and methods may be used to form a fistula between two blood vessels.

BACKGROUND

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. Needles, catheters, or other cannulas may then be inserted into the blood vessels near the fistula to draw blood from the circulatory system, pass it through a dialysis machine, and return it to the body. The quickened flow provided by the fistula may provide for effective hemodialysis. In a mature fistula, the flow rate through the fistula may be on the order of 300-500 ml/min, or may be on the order of 300-1500 ml/min, or more.

In other instances, a fistula may be formed between two veins to form a veno-venous fistula. Such a veno-venous fistula may be used to help treat portal venous hypertension. Specifically, cirrhosis or other liver diseases may cause increased resistance to flow through the portal veins draining from the intestine to the liver. This increased resistance may cause massive dilation of blood vessels, which may rupture spontaneously. To help prevent this undesirable outcome, a fistula may be formed between a portal vein and one of the major branches, thereby lowering venous pressure in the portal vein. As such, it may be useful to find improved ways to form a fistula between two blood vessels.

BRIEF SUMMARY

Described here are devices and methods for forming a fistula between two or more blood vessels. Generally, the devices described here comprise one or more catheters. Each catheter generally comprises a distal end, an intermediate portion, and a proximal end. The proximal end of the catheter may comprise one or more handles or adaptors, which may be used to control or manipulate the catheter. The handle or adaptor may comprise one or more ports for introducing devices (e.g., electrical leads, guidewires) or substances (e.g., contrast fluid, perfusion fluid, or the like) into the catheter. The handle or adaptor may additionally comprise one or more alignment projections that may be used to help align one catheter relative to another catheter.

In some variations of the catheters described here, the catheters may comprise one or more alignment elements to help align one catheter relative to another or relative to an anatomical structure. The alignment elements may be any suitable element or structure that may help align one or more catheters in one or more blood vessels. In some variations, one or more of the alignment elements may comprise one or more magnetic alignment elements. The magnetic alignment elements may be used to help advance a catheter through the vasculature, may be used to draw two or more catheters closer together within the vasculature, or may be used to axially and/or rotationally align two or more catheters. Magnetic alignment elements may or may not be organized into one or more arrays, and each magnetic alignment element may have any suitable size or shape. In some variations, one or more magnetic alignment elements may be semi-cylindrical, cylindrical, or annular-shaped. In other variations, one or more alignment elements may be bar-, billet-, or box-shaped.

In other variations, the catheters may comprise one or more markers. In some of these variations, the marker may be directly visualized. In some of these variations, the catheters may comprise one or more marker bands along a portion thereof. In other variations, the marker may be indirectly visualized (e.g., via fluoroscopy, x-ray, or ultrasound visualization). In some of these variations, the device may comprise one or more marker bands that may allow for rotational alignment of one or more catheters.

In some variations of the devices and methods described here, a catheter may comprise one or more elements for forming a fistula between vessels. The fistula-forming element may be any mechanism suitable for forming a perforation between two blood vessels. For example, in some variations the catheter may comprise one or more mechanical cutting elements, such as, for example, a blade, a needle, a lancet, or the like. In other variations, the catheter may comprise one or more electrodes for ablating or otherwise vaporizing tissue between two blood vessels. In some variations, the electrodes comprise one or more ablation surfaces for ablating tissues. In some variations the ablation surface is flush with the surface of the catheter. In other variations, the ablation surface may project from the surface of the catheter. In still other variations, the ablation surface may be recessed relative to the surface of the catheter. In still other variations, the ablation surface may be adjustable relative to the surface of the catheter.

In some variations of the device and methods described here, a catheter may comprise one or more expandable structures. The catheter may comprise any number of expandable structures (e.g., zero, one, two, or three or more), and each expandable structure may be any suitable expandable structure (e.g., a balloon, an expandable cage, mesh, or the like). The expandable structure or expandable structures may be used to help place the catheter in apposition with a tissue wall. In other variations, one or more expandable structures may be used to dilate one or more portions of a blood vessel. In still other variations, one or more expandable structures may be used to expand or otherwise modify the size of a fistula. In yet other variations, an expandable structure may comprise one or more electrodes that may be activated to deliver RF energy to one or more blood vessels, which may restrict blood flow therethrough. Additionally or alternatively, an expandable structure may help to anchor a catheter at least temporarily at certain position within the vasculature.

In some variations a catheter may comprise one or more components for joining or otherwise fixing a portion of a first blood vessel to a second blood vessel. In some variations, a catheter may comprise one or more components (e.g., an electrode) configured to supply electrical, ultrasound, or laser energy to tissue. In other variations, a catheter may comprise one or more needles configured to deliver an adhesive between a first blood vessel and a second blood vessel. In still other variations, a catheter may be configured to deploy one or more barbs, staples, or other implants into tissue of the first and second blood vessels.

BRIEF DESCRIPTION OF THE DRAWINGS

FIGS. 1A-1C depict different perspective views of the distal portion of one variation of the catheters described here.

FIGS. 2, 3, 4, 5, 6A, 6B, 7A, 7B, 8 depict distal portions of variations of the catheters described here.

FIGS. 9A-9D, 10A-10C, 11, and 12 depict variations of catheters described here comprising one or more expandable members.

FIGS. 13A and 13B depict the proximal portions of two variations of the catheters described here.

FIG. 14A shows a perspective view of one variation of a catheter comprising a marker band. FIG. 14B depicts a perspective view of a marker band, while

FIGS. 15A and 15B depict two variations of proximal portions of the catheters described here.

FIGS. 16A and 16B depict another variation of the catheters described here.

FIGS. 17A and 17B illustrate a method by which an external magnet may be used to help advance a catheter through the vasculature.

FIGS. 18A and 18B depict two variations of catheters comprising electrodes with flat ablation surfaces.

FIGS. 19, 20, 21A, 21B, 22, 23, 24A, and 24B depict distal portions of variations of the catheters described here.

FIG. 25A shows a partial cross-sectional view of a distal portion of a variation of the catheters described here. FIGS. 25B-25D depict perspective views of the catheter of FIG. 25A.

FIG. 26A depicts a distal portion of a variation of the catheters described here. FIG. 26B depicts the catheter of FIG. 26A with another variation of the catheters described here.

FIGS. 27A and 27B depict two perspective views of a variation of the catheters described here. FIGS. 27C and 27D depict two variations of the catheters described here placed in blood vessels.

FIGS. 28A and 29A depict two variations of electrodes suitable for use with the catheters described here. FIGS. 28B and 29B depict two variations of catheters that include the electrodes of FIGS. 28A and 29A.

FIGS. 30, 31A-31B, 32, 33A-33B, 34, 35A-35B, and 36 depict several variations of the catheters described here.

FIGS. 37A and 37B show cross-sectional views of a variation of a catheter comprising a blade.

FIG. 39A depicts a perspective view of a variation of a catheter comprising a blade. FIGS. 39B and 39C depict cross-sectional side views of the catheter shown in FIG. 39A.

DETAILED DESCRIPTION

Figure 7B:
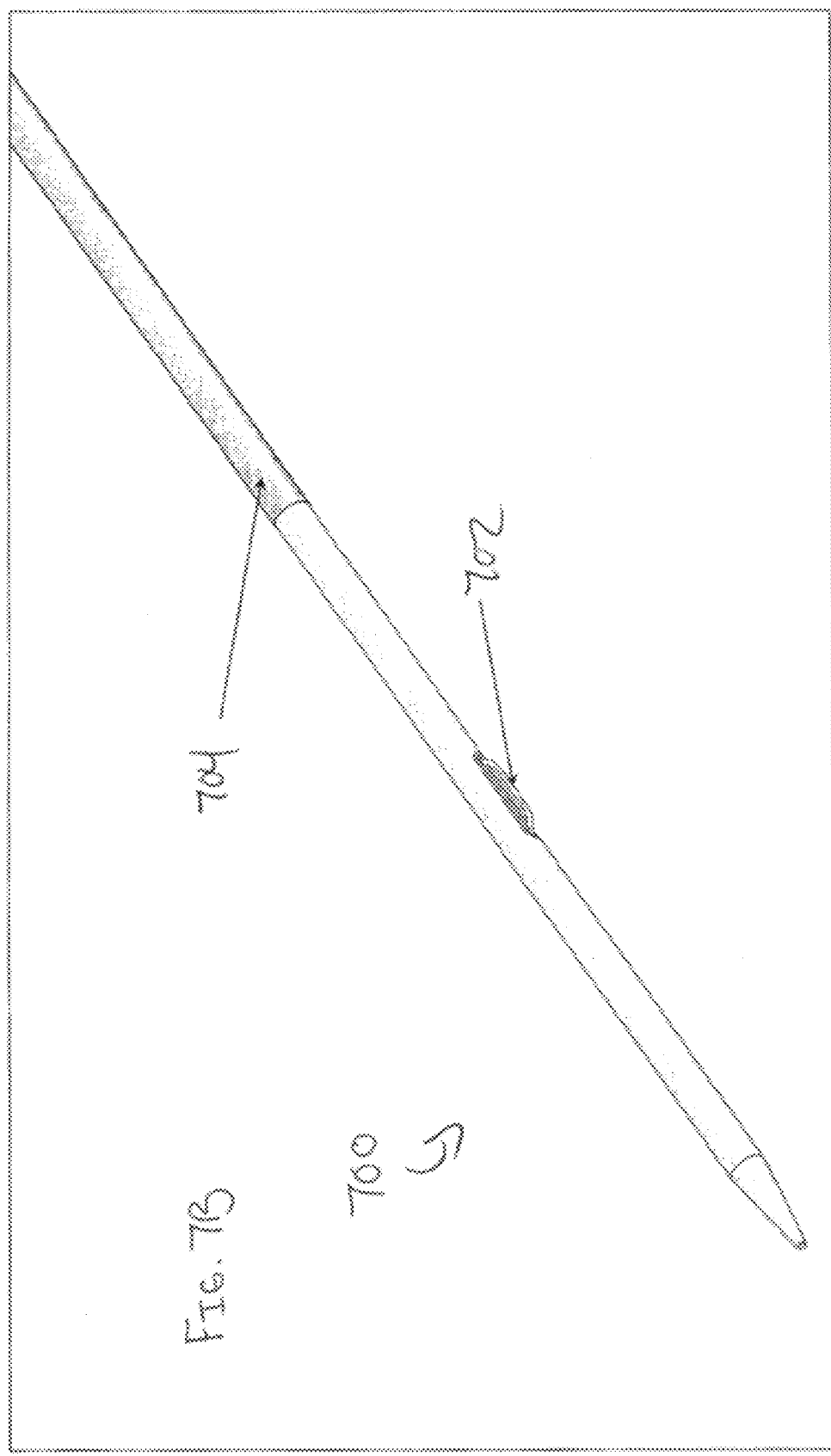

Described here are devices and methods for forming a fistula. In some variations, the devices and methods may be used to form a fistula between two blood vessels (e.g., an arteriovenous fistula between an artery and a vein or a venovenous fistula between two veins). Generally, to form such a fistula between two blood vessels, one or more catheters are advanced in a minimally invasive fashion through the vasculature to a target location. In some instances, a single catheter may be placed in a blood vessel to form a fistula with an adjoining blood vessel. In other instances, a system comprising multiple catheters may be used to form a fistula. For example, in some instances a catheter may be placed in each of the two blood vessels. In these instances, it should be appreciated that each catheter may or may not have the same configuration of elements, and that some catheters may be different from and/or complementary to other catheters, as will be described in more detail below.

One or a combination of the catheters described here may be used to form a fistula, as will be described in more detail below. Generally, each catheter will have a proximal end, a distal end, and an intermediate portion connecting the proximal and distal ends. The proximal end may comprise one or more adaptors or handles, which may be utilized to help aid in advancement, positioning and control of the catheter within the vasculature, and may further be used to actuate one or more components of the catheter and/or introduce one or more fluids or substances into and/or through the catheter. The catheter may comprise one or more elements that may aid in fistula formation. In some variations, one or more portions (e.g., the distal end and/or the intermediate portion) of the catheter may comprise one or more alignment elements (e.g., one or more magnets) that may help align the catheter with another catheter positioned in a related blood vessel and/or bring the catheters (and blood vessels) in closer approximation. Additionally or alternatively, one or more portions (e.g., the distal end and/or an intermediate portion) of the catheter may comprise one or more mechanisms for forming a fistula.

The catheters may additionally comprise one or more lumens or passageways extending at least partially along or through the catheter, and may be used to pass one or more guidewires, one or more drugs or fluids (e.g., contrast agents, perfusion fluids), combinations thereof, or the like at least partially along or through the catheter. The distal tip of the catheter may be configured to aid in advancement of the catheter and/or to be atraumatic. In some variations, the tip may comprise one or more rapid exchange portions or other lumens for advancement of the catheter over a guidewire. In still other variations, the tip portion may have a guidewire attached to or otherwise integrally formed with the catheter.

Additionally, in some variations the catheters may further comprise one or more external expandable elements (e.g., a balloon, expandable cage, mesh, or the like) that may help position a catheter within a blood vessel. Additionally or alternatively, the one or more expandable elements may affect the flow of blood through one or more blood vessels (e.g., by temporarily occluding blood flow through the blood vessel, dilating one or more portions of a blood vessel, constricting one or more portions of a blood vessel, or the like). In some instances, one or more expandable elements may act to temporarily anchor a portion of the catheter relative to a blood vessel. In variations where the catheter comprises one or more shape-changeling elements, as will be described in more detail below, the use of an expandable element to temporarily anchor a portion of the catheter relative to a blood vessel may aid in altering the shape of the catheter. It should be appreciated that the catheters described here may have any combination of the aforementioned elements, each of which will be described in more detail below.

FIGS. 1A-1C depict an illustrative variation of a catheter (100) suitable for use in forming a fistula. Specifically, FIG.

1A depicts a perspective view of distal portion (108) of catheter (100) with sleeve (106) covering at least a portion of the catheter (100). FIG. 1B depicts a partially-transparent view of catheter (100) with sleeve (106) illustrated as partially transparent. FIG. 1C depicts a partially-perspective view of catheter (100) with sleeve (106) and the catheter body illustrated as partially transparent. As shown in these figures, catheter (100) may comprise electrode (102) having an exposed ablation surface (105) and a lead wire (104) attached thereto. Also shown there are proximal anchoring magnet (116), distal anchoring magnet (118), and rapid exchange portion (110) including first and second apertures ((112) and (114) respectively), each of which will be described in more detail below. To form a fistula using catheter (100), ablation surface (105) of electrode (102) may be placed in electrical contact with a target tissue, and a current may be supplied to the electrode (102) to ablate or vaporize tissue. Individual catheter components and methods will be described in more detail below.

Fistula Formation

As mentioned above, the catheters described here may comprise one or more elements for forming a fistula. These fistula-forming elements may utilize any structure or mechanism capable of cutting, ablating, vaporizing, dissolving, or otherwise removing tissue between adjoining vessels, such as, for example, one or more electrical mechanisms (e.g., one or more electrodes or electrocautery devices), one or more mechanical mechanisms (e.g., one or more cutting blades, lancets, needles, or the like), one or more chemical mechanisms (e.g., one or more enzyme-releasing devices), cryogenic-cautery devices, laser ablation devices (e.g., one or more fiber-optic laser light sources), combinations thereof or the like. A catheter may have any suitable number (e.g., zero, one, two, three, or four or more) and combination of these fistula-forming elements, and these fistula-forming elements may be located in or on any suitable portion of the catheter (e.g., the distal end, an intermediate portion, combinations thereof). In variations where a catheter comprises two or more fistula-forming elements, multiple fistula-forming elements may form multiple fistulas, simultaneously or sequentially. In other variations, multiple fistula-forming elements may interact to form a single fistula.

In variations where a system comprising multiple catheters is used to create a fistula between two blood vessels, each catheter may comprise a fistula-forming element, but need not. Indeed, in some of these variations, only one catheter may comprise a fistula-forming element. In some of these instances, the other catheter may still help align the catheters and/or approximate the blood vessels, but may not directly contribute to tissue removal. In variations where multiple catheters each comprises a fistula-forming element, the catheters may have complimentary fistula-forming elements. For example, in variations where two or more catheters comprise electrodes, as explained in more detail below, one catheter may comprise an electrode that acts as an active electrode, while another catheter may comprise an electrode that acts as a passive or ground electrode.

Electrodes

As mentioned above, in some variations of the catheters described here, a catheter may comprise one or more electrodes for use in forming a fistula. Generally, in these variations, a catheter may comprise an electrode body and at least one lead wire or other conductor attached thereto for connecting the electrode to an electrosurgical generator. In some variations, one or more portions of a lead wire may act as an electrode to ablate tissue. A catheter may have any suitable number of electrodes (e.g., zero, one, two, or three or more), and each electrode may be positioned at any suitable point along the catheter's length (i.e., the distal end, an intermediate portion, etc.), and may have any suitable size and shape, as discussed in more detail below. It should be appreciated that when used with a direct current generator, an electrode may either act as an active electrode (e.g., in which current is supplied to the electrode to ablate tissue) or a passive ground electrode (e.g., in which current is carried away from the electrode to a grounded location), depending on the manner in which it is used. When a catheter having an active electrode is used in conjunction with a catheter having one or more passive ground electrodes, electrical energy may have a tendency to flow from the active electrode through intervening tissue and to the passive electrode. In this way, the electrode pair may help prevent energy loss to surrounding tissue.

In some instances one or more electrodes may be connected to an electrosurgical generator, power supply, or other waveform generator that is configured to generate an alternating current. In some of these variations, two or more electrodes may be connected to the bipolar outputs of a generator. In other variations, one or more electrodes may be connected to a monopolar output of a generator. In some of these variations, a first electrode is attached to the active output of the generator, and a return electrode (e.g., a large metal plate or flexible metalized pad) may be temporarily attached or affixed to the patient and connected to the return output of the generator. In others of these variations, two or more electrodes may be attached to an active output of the generator, and a return electrode may be temporarily attached or affixed to the patient and connected to the return output of the generator. In still other variations, a first electrode may be attached to the active output of the generator, and a second electrode may be attached to the return output of the generator in a "focus monopolar" configuration.

Generally, at least a portion of each electrode may be exposed to the surrounding environment (e.g., through one or more apertures or openings in the catheter body). This exposed surface may be configured to contact surrounding tissue (e.g., a blood vessel wall) or fluids, and may act as an ablation surface such that current may be supplied to and/or carried from tissue via the ablation surface to facilitate ablation or vaporization of tissue. In some variations, the ablation surface may be temporarily covered (e.g., by a sheath or tubing) such that the ablation surface does not contact tissue. In these instances, the temporary covering may be moved or removed to expose the ablation surface to the surrounding environment. In other variations, the ablation surface may be temporarily recessed or held within the catheter, and in some of these instances may be advanced out of the catheter to contact tissue. The ablation surface need not be movable, and may instead be fixed relative to the catheter. Additionally or alternatively, in some variations an exposed electrode surface may comprise a porous coating that allows conduction of current thereto or therefrom while preventing direct contact between two electrodes, as will be described in more detail below. The electrodes may be made from any suitable material or combination of materials. In some variations the electrode may comprise one or more refractory metals. For example, an electrode may comprise tungsten, molybdenum, niobium, tantalum, rhenium, combinations or alloys thereof.

The electrode ablation surface may have any shape or size suitable for ablating tissue. For example, the ablation surface may be oval-shaped, circular, rectangular, triangular, pentagonal, hexagonal, polygonal, irregularly shaped, or the like. Alternatively or additionally, the ablation surface may be roughened or otherwise patterned, as will be described in more detail below. In variations where the ablation surface is exposed through one or more apertures or openings in the catheter body, these apertures or openings may at least partially define the size and shape of the ablation surface. In variations where the catheter comprises a nesting material, as will be described in more detail below, the nesting material may at least partially define the size and shape of the ablation surface. The size and shape of the ablation surface may help determine the size and shape of the resulting fistula. The ablation surface may have any suitable length (e.g., about 0.0625 in, about 0.1875 in, between about 0.05 in and about 0.2 in, between about 0.05 in and about 0.075 in, between about 0.15 in and about 0.2 in, and the like) and any suitable width (e.g., about 0.0313 in., about 0.0625 in, between about 0.025 in and about 0.075 in, between about 0.025 and about 0.05 in, between about 0.05 and about 0.075 in, and the like). In variations where the ablation surface is circular, cylindrical, or semi-spherical, the ablation surface may have any suitable radius (e.g., about 0.03 in, about 0.04 in, about 0.05 in, and the like). In variations where a portion of the electrode extends out of a portion of the catheter, as will be described in more detail below, the ablation surface may have any suitable height (e.g., about 0.25 mm, about 0.5 mm, about 0.75 mm, about 1 mm, between about 0.1 and about 1.5 mm, between about 0.25 and about 1 mm, between about 0.25 and about 0.75 mm, greater than about 1.5 mm, or the like).

When two or more electrodes are used in conjunction to form a fistula, the two or more electrodes may have different sizes. For examples, in some variations, a first electrode having a larger ablation surface (e.g., a rectangular ablation surface of about 0.2 inches by about 0.05 inches) may be placed in an artery, and a second electrode having a smaller ablation surface (e.g., a rectangular ablation surface of about 0.1 inches by about 0.05 inches) may be placed in a vein. In these variations, when an RF signal (e.g., a sinusoidal waveform, or the like) of a certain power (e.g., 40 W) is applied to the electrodes to form a fistula between the artery and the vein, the second electrode may have a larger current density than the first electrode by virtue of its smaller ablation surface. This may cause the formation of the fistula to begin in the vein, and propagate through the artery. Directional formation of fistula may help prevent extravasation (e.g., blood loss to surrounding tissue) in instances where a fistula is not fully formed between an artery and a vein (as partial fistula formation beginning in an artery may have a greater risk of extravasation than partial fistula formation beginning an a vein).

In some variations, the ablation surface may be flush with an outer surface of the catheter body. FIG. 2 illustrates one such variation of catheter (200) comprising an electrode body (202) having ablation surface (205). Also shown there are lead wire (204), proximal anchoring magnet (206), and distal anchoring magnet (208). As shown in FIG. 2, ablation surface (205) may be exposed through catheter (200), and may be substantially flush with the outer surface of catheter (200). While shown in FIG. 2 as having a cylindrical electrode body (202) with a rounded rectangular ablation surface (205), it should be appreciated that electrode body (202) may have any suitably-shaped ablation surface (205), such as those mentioned above. While catheter (200) is shown in FIG. 2 as comprising a proximal (206) and a distal (208) anchoring magnet, it should be appreciated that catheter (200) may have any alignment elements or combinations of alignment elements as described in more detail below, or may not comprise any alignment elements.

As shown in FIG. 2, ablation surface (205) may be flush with catheter (200), and thus may have a rounded surface. In other variations of the device described here, a catheter may comprise an electrode where one or more portions of the ablation surface may be flat. For example, FIGS. 18A and 18B illustrate end views two variations of catheters having flat ablation surfaces. FIG. 18A shows a first variation of catheter (1800) comprising a catheter body (1802) and an electrode (1804) comprising a flat ablation surface (1806). A flat ablation surface (1806) may help provide better tissue apposition between the electrode (1804) and tissue (not shown). Specifically, when two catheters, each comprising an electrode having a flat ablation surface (such as ablation surface (1806)), are placed in different blood vessels and are brought in closer approximation (e.g., via one or more of the alignment elements or shape-changing members described in more detail below), the two ablation surfaces may cause vessel tissue to at least temporarily flatten therebetween. This may increase the electrical isolation of the flattened tissue (e.g., current supplied to an active electrode will be more likely to pass through the flattened tissue as it travels to the ground electrode, rather than be lost to other fluids or surrounding tissue), which may aid in fistula formation.

Although the variation of ablation surface (1806) shown in FIG. 18A may not be completely flush with the outer surface of the catheter body (1802), the plane of the flat ablation surface (1806) shown there does not protrude beyond the edge of catheter body (1802). In other variations, however, a flat ablation surface may be recessed into the catheter body, or may protrude therefrom. For example, FIG. 18B shows another variation of catheter (1808) comprising a catheter body (1810) and an electrode (1812) comprising a flat ablation surface (1814). As shown there, the plane of the ablation surface (1814) may protrude a distance (x) from the catheter body (1810). This distance (x) may be any suitable distance, such as, for example about 0.25 mm, about 0.5 mm, about 0.75 mm, about 1 mm, between about 0.1 and about 1.5 mm, between about 0.25 and about 1 mm, between about 0.25 and about 0.75 mm, or the like. A protruding ablation surface (1814) may press into tissue as catheter (1808) is brought toward another catheter, which may help increase tissue apposition with the ablation surface, which may aid in tissue ablation. In some variations, the electrode may be configured such that distance (x) is adjustable. For example, in these variations, one or more portions of the device (e.g., a rod, lead wire, or other actuation mechanism) may adjust the protrusion of the device. For example, in some variations, distance (x) may be adjustable between about 0 mm and about 1.5 mm, between about 0 mm and about 1.0 mm, between about 0 mm and about 0.5 mm, between about 0.25 mm and about 0.75 mm and the like. It should also be appreciated that the ablation surface may be configured to move from a recessed position and a protruding position.

In some variations, one or more ablation surfaces of an electrode may be patterned, but need not be. FIG. 28A shows a first variation of electrode (2800) comprising a surface (2802). As shown there, surface (2802) may be flat, and may be made from a conductive material. Surface (2802) may act as an ablation surface when electrode (2800) is used with one or more of the catheters described here. For example, FIG. 28B shows a variation of catheter (2804) comprising electrode (2800) at least partially housed in a nesting material (2806) within catheter body (2808). As shown there, surface (2802) may act as an ablation surface. It should be appreciated while shown in FIG. 28B as comprising a plurality of coupling magnets (2810) (which will be described in more detail below) located both proximally and distally of electrode (2800), it should be appreciated that catheter (2804) may comprise any suitable alignment elements or combination of alignment elements as described in more detail below.

FIG. 29A shows a second variation of an electrode (2900) comprising a patterned surface (2902). As shown there, electrode (2900) may comprise a body (2904) made from a conductive material. A first side of body (2904) may comprise a plurality of channels (2906) which may define a plurality of projections (2908), each having a raised surface (2910). Channels (2906) may be at least partially filled with a non-conductive encapsulant material (not shown) such as, for example, one or more ceramic materials, parylene, one or more polymeric resins (e.g., polyetherimide, polyetheretherketone, one or more phenolic resins, or the like), silica, one or more metal oxides (e.g., aluminum oxide), combinations thereof, and the like. For example, FIG. 29B shows a variation of catheter (2912) comprising electrode (2900) at least partially housed in a nesting material (2913) within catheter body (2915). As shown there, an encapsulant material (2914) may fill the channels of the electrode (2900) such that the encapsulant material (2914) and raised surfaces (2910) form a flat patterned surface (2902). Patterned surface (2902) may be exposed through catheter body (2915), and may act as an ablation surface, as will be described immediately below. It should be appreciated while shown in FIG. 29B as comprising a plurality of coupling magnets (2916) (which will be described in more detail below) located both proximally and distally of electrode (2900), it should be appreciated that catheter (2912) may comprise any suitable alignment elements or combination of alignment elements as described in more detail below.

When patterned surface (2902) is used as an ablation surface, the raised surfaces (2910) of projections (2908) may be capable of conducting electrical energy to tissue, while the encapsulant material (2914) may prevent or resist the flow of energy therethrough. Since only a portion of the patterned surface (2902) may be conductive via raised surfaces (2910), the effective electrode area provided by patterned surface (2902) is decreased. When a power output is applied to an electrode, the decreased effective electrode area may increase the current density on the conductive portions of the electrode (e.g., the conductive raised surfaces (2910) of electrode (2900). Current may build on the edges of the raised surfaces (2910), and the increased current density may promote current arcing between electrodes, which may aid in the ablation or vaporization of tissue.

While shown in FIGS. 29A and 29B as being either triangular or squared in cross-sectional area, the projections (2908) (and their raised surfaces (2910)) may have any suitable cross-section shape or shapes, such as, for example, rectangles, trapezoids, circles, ovals, polygons, shapes with irregular geometry, or the like. Projections (2908) and channels (2906) may be formed in any suitable manner. In some variations, one or more channels may be formed (e.g., by cutting, etching, carving, or the like) in a block of material (such as electrode (2800) described above in regards to FIGS. 28A and 28B) to define projections (2908). In other variations, one or more projections may be formed separately from a base member, and then may be attached to the base member.

In variations where a catheter comprises a flat ablation surface, the flat ablation surface may have any suitable cross-sectional shape (e.g., a circle, oval, triangle, square, rectangle, pentagon, hexagon, other polygon, irregular shape, or the like). Additionally or alternatively, the ablation surface may be patterned, such as described in more detail above. FIG. 3 shows one variation of catheter (300) comprising an electrode body (310) with a hexagonal ablation surface (311) protruding from catheter (300). Also shown there are proximal anchoring magnet (302), distal anchoring magnet (304), lumen (308), and concentric electric conductor (314), each of which will be described in more detail below. Additionally, while flat ablation surfaces (1806) and (1814) are shown in FIGS. 18A and 18B respectively as being parallel to the catheter bodies ((1802) and (1804), respectively), it should be appreciated that a flat ablation surface may be angled relative to a catheter body. It should also be appreciated that electrode may have an ablation surface that protrudes from the catheter body but does not comprise a flat surface. For example, in some variations, such as ablation surface (103) of catheter (100) illustrated in FIGS. 1A-1C and described in more detail above, the ablation surface may be hemispherical.

In variations where one or more portions of an electrode body protrudes from the catheter body, one or more portions of the catheter may taper to help reduce trauma that may be caused by the protruding ablation surface (or edges thereof) as a catheter is advanced through a blood vessel. In some variations, the ablation surface itself may be tapered. In other variations, one or more additional components, such as the catheter body or an electrode nesting material (as will be described in more detail below), may taper to the ablation surface. For example, FIG. 4 depicts a variation catheter (400) comprising an electrode (402) having an ablation surface (404) protruding from the surface of the catheter (400). Also shown there is nesting material (406) partially covering the electrode (402). As shown in FIG. 4, nesting material (406) may taper from the surface of catheter (400) to ablation surface (404), which may help minimize tissue trauma.

As mentioned immediately above, in some variations one or more portions of an electrode may be at least partially covered or housed by a nesting material. Indeed, in some of these variations the entire electrode body except for the ablation surface is covered by a nesting material. The nesting material may serve a number of useful purposes. As described immediately above, the nesting material may help prevent damage done by the electrode to tissue as the catheter is advanced through a blood vessel. In some variations, the nesting material may hold an electrode in place relative to one or more other elements of a catheter (e.g., one or more alignment elements, or the like). Additionally, in some instances, the nesting material may insulate the electrode body from surrounding tissue or other portions of the catheter, which may protect or shield the other portions of the catheter. For example, thermal insulation provided by the nesting material may protect other catheter components from heat that may be generated by the electrode. Additionally or alternatively, electrical insulation provided by the nesting material may help minimize current loss to other parts of the catheter or surrounding tissue. The nesting material may be made of any heat and/or electrically resistant materials. Examples of suitable nesting materials include, but are not limited to, ceramic materials, parylene, one or more polymeric resins (e.g., polyetherimide, polyetheretherketone, one or more phenolic resins, or the like), silica, one or more metal oxides (e.g., aluminum oxide), combinations thereof, or the like. In some instances, the nesting material may be a machined solid or may be molded. In other instances, the nesting material may be plasma-sprayed, coated or otherwise deposited on one or more portions of the electrode. It should also be appreciated that in variations where one or more portions of the electrode is moveable relative to the catheter, the nesting material may or may not also be movable relative to the catheter. The nesting material and electrode may move in concert, but need not. In some of these variations, one or more pieces/portions of nesting material may move with the electrode, while one or more pieces/portions of nesting material remain fixed relative to the catheter. Additionally, the nesting material may be configured to house or otherwise hold one or more alignment elements (e.g., one or more magnets), as will be described in more detail below.

In some variations, a nesting material may provide directed heat dissipation, such that heat is directed towards the center of the ablation surface away from the edge of the ablation surface. For example, the nesting material may be made of various materials with different heat-transfer properties, where the nesting material near the edge of the ablation surface may be made of a material that is resistant to heat-transfer, while the nesting material near the center of the ablation surface may be made of a material that has efficient heat-transfer properties. Intermediate positions between the edge and center of the ablation surface may have intermediate heat-transfer properties. Alternatively, the nesting material may be made of a single material whose density varies from the edge to the center of the ablation surface, e.g., the material of the edge region may have a density that is greater than the density of the material at the center region. Any suitable heat and/or current nesting materials and configurations may be used to direct or otherwise regulate the temperature and/or current that may be a result of activating the electrode.

As mentioned above, a nesting material may help shield or insulate one or more portions of an electrode body from surrounding tissue. Although the catheter body may cover one or more portions of a nesting material, the catheter body need not. For example, FIG. 19 shows one variation of catheter (1900). Shown there are distal catheter body (1902), proximal catheter body (1904), and nesting material (1906) housing electrode (1908) and coupling magnets (1910). In these variations, proximal (1904) and distal (1902) catheter bodies may be attached to the nesting material (1906) such that a circumference of at least a portion of the nesting material (1906) is not covered by a catheter body. In these instances, the diameter of the nesting material (1906) and the electrode (1908) may be increased, which may allow the size of ablation surface of electrode (1908) to be increased without increasing the overall diameter of the catheter (1900)).

In other variations of the catheters described here, an ablation surface may be at least partially recessed into a surface of the catheter. In some instances, direct contact between an electrode surface and a blood vessel wall may yield carbon deposition on the surface during tissue ablation. As such, a recessed ablation surface may help ablate tissue while minimizing carbon build-up on the ablation surface by providing spacing between the ablation surface and the blood vessel wall. Specifically, when a catheter is placed against a blood vessel wall, blood or other fluid may be temporarily trapped within the recessed portion. The blood may provide an efficient conduction medium to help transfer the ablation energy to a blood vessel wall without carbon build-up on the ablation surface, which may help prevent or otherwise reduce degradation of the electrode. FIG. 5 shows a variation of catheter (500) comprising an electrode (502) with a recessed electrode ablation surface (504). Also shown there is nesting material (506) at least partially covering electrode (502). As noted above, nesting material (506) may help separate and insulate ablation surface (504) and electrode (502) from the remaining components of catheter (500). The size, shape, and depth of the aperture may be determined in part by the desired volume of blood that is to be held or otherwise trapped in the recessed portion of the catheter (500).

It should be appreciated that although shown in the variations above as having a single ablation surface, the electrodes described here may have more than one ablation surface. Each electrode may have one, two, three, or four or more ablation surfaces, and each ablation surface may have any suitable placement relative to the catheter body. For example, in some variations an electrode may have a first ablation surface on a first side of the catheter and second ablation surface located distal or proximal to the first ablation surface along the first side of the catheter. Depending upon the spacing between the first and second ablation surfaces, this may contribute to the formation of two fistulas, or one enlarged fistula. In other variations, the two or more ablation surfaces may be on different sides of the catheter, e.g., a first ablation surface may be on one portion of the catheter, and a second ablation surface may be located about 10°, about 20°, about 30°, about 45°, about 60°, about 90°, about 120°, about 150°, about 180°, about 200°, about 300°, etc. from the first ablation surface.

Additionally, in some variations, at least a portion of the electrode body may be housed inside of the nesting material. In these variations, the housed portion of the electrode may have any suitable size or shape. For example, in the variation of catheter (200) shown in FIG. 2, electrode body (202) comprises a cylindrical portion (204) housed within the catheter body. Alternatively, the housed portion may be an elongate shape having a rectangular, triangular, elliptical, ovoid, polygonal or irregular cross-section. In still other variations, the housed portion of the electrode may be a semi-cylinder, a quarter-cylinder, or another suitable fractional portion of a cylinder. For example, FIG. 6A shows one such variation of catheter (600) comprising an electrode body (602) having an ablation surface (603), lead wire (605), proximal anchoring magnet (604), distal anchoring magnet (606), and lumen (608). In this variation, the housed portion of electrode body (602) may be semi-cylindrical. Variations having a semi-cylindrical electrode body may allow for lumen (608) to pass thereby, as will be described in more detail. In other variations, the electrode may have an aperture through it, such that a lumen of the catheter may pass therethrough. For example, in the variation of catheter (300) shown in FIG. 3 and described in more detail below, electrode body (310) is shown as having an aperture defined therein, such that lumen (308) may pass through the electrode body (310).

While many of the catheter variations described above are illustrated as having an electrode or electrodes that are fixedly attached relative to the catheter body, it should be appreciated that the electrodes (or one or more portions thereof) described here may also be adjustable or otherwise moveable relative to the catheter body. For example, an electrode may be positioned such that an ablation surface thereof may be substantially flush with or recessed within the catheter as the catheter is advanced through a blood vessel to the target site, and may subsequently be adjusted to protrude from the catheter body. In some instances, the entire electrode body may be adjustable, while in other instances only a portion of the electrode is adjustable. Any suitable mechanism may be used to adjust the electrode, such as, for example, a spring mechanism.

FIGS. 7A and 7B illustrate a variation of a catheter (700) comprising a movable electrode (702) and sleeve (704). As shown there, electrode (702) may comprise a spring wire electrode, which may be movable between a retracted configuration, in which electrode (702) is retained within the catheter (as shown in FIG. 7A), and a protruding configuration, in which electrode (702) projects from the surface of catheter (700) (as shown in FIG. 7B). The electrode (702) may or may not be naturally biased to project from the catheter. When the electrode (702) is naturally biased to project from the catheter, such as in the variation shown in FIGS. 7A and 7B, a structure may be used to hold or maintain the electrode (702) in a retracted configuration. For example, sleeve (704) may be used to control the protrusion of electrode (702). Sleeve (704) may be advanced distally to hold electrode (702) in a retracted configuration, as shown in FIG. 7A. Sleeve (704) may then be withdrawn proximally to expose electrode (702), which may then naturally move to a protruding configuration, as illustrated in FIG. 7B. Electrode (702) may protrude any suitable amount from the surface of the catheter (700) (e.g., between about 0.1 mm to about 1 mm, about 0.25 mm, about 0.5 mm, about 0.75 mm, about 1.0 mm, and the like).

While shown in FIGS. 7A and 7B as being naturally biased into a protruding configuration, electrode may be manually adjustable between a retracted configuration and a protruding configuration. For example, FIG. 8 depicts one such variation of a catheter (800) with a leaf spring electrode (802) that may be actuated by wire (804). As shown there, wire (804) may be slidably disposed within rod (806). Movement of wire (804) may transition electrode (802) between a retracted configuration and a protruding configuration. The amount of protrusion of the electrode (802) may be determined at least in part by the amount of movement of the wire (806), allowing for additional user control in deployment of the electrode. In other variations, wire (804) may be attached to rod (806), and rod (806) may be movable within catheter (800) to advance or retract wire (804). In these variations, the amount of protrusion of the electrode (802) may be determined at least in part by the amount of movement of the rod (806).

In variations where the electrode comprises a spring electrode or another deployable electrode, one or more portions of the electrode may be covered by a nesting material, such as those described above. FIG. 20 shows one such variation of a catheter (2000) comprising a deployable electrode (2002). As shown there, catheter (2000) may comprise catheter body (2001), electrode (2002) and a distal coupling magnet array (2004). At least a portion of electrode (2002) may be covered/coated with an insulating material (2006), such that the uncovered portion (2008) of the electrode (2002) may act as an ablation surface. The insulated portion of the electrode (2002) may be coated in any suitable manner (e.g., plasma spraying, flame spring, dip coating, or the like), and insulating material (2006) may be any suitable material, such as one or more of the nesting materials described above. A rod, stiffened lead wire, or other actuation mechanisms (not shown) may be used to move the electrode (2002) between a low-profile configuration (not shown), in which the electrode (2002) is housed within or flush with the catheter body (2001), and a deployed configuration, as shown in FIG. 20. To move electrode (2002) to a deployed configuration, the actuation mechanism may compress the electrode (2002) such that it bends, flexes, or otherwise deforms away from the catheter body (2001). It should also be appreciated that in some instances, the electrode (2002) may naturally bend or flex away from catheter body (2001), and an actuation mechanism (or a sleeve) may be used to move the electrode (2002) to a low-profile configuration.

In variations in which a catheter comprises a deployable electrode, it should be appreciated that one or more ablation surfaces of the electrode may be patterned, as described in more detail above. FIG. 30 shows one such variation of a catheter (3000) comprising a deployable electrode (3002). As shown there, catheter may comprise an electrode (3002) having a first electrode portion (3003) and a second patterned electrode portion (3004), catheter body (3006), and nesting material (3008) housing coupling magnets (3010) and having a track (3012). Electrode (3002) may be advanced from a retracted position, in which electrode (3002) is contained within track (3012) of nesting material (3008). To deploy electrode (3002), first electrode portion (3003) may be configured to bend or flex away from the catheter body (3006), similar to electrode (2002) described above in relation to FIG. 20. Second electrode portion (3004) may be attached to first electrode portion (3003), such that second electrode portion (3004) extends from catheter body (3006) when first electrode portion (3003) bends or flexes away from catheter body (3006). Second electrode portion (3004) may comprise one or more patterned surfaces, such as patterned surface (2902) of electrode (2900) described above with respect to FIGS. 29A and 29B. In some variations, at least a portion of first electrode portion (3003) may be covered or otherwise coated with one or more insulating materials, such as one or more of the nesting materials described above. While shown in FIG. 30 as having two coupling magnets (3010) located distally from electrode (2900), it should be appreciated that catheter (3000) may comprise any alignment elements or combination of alignment elements, such as those described in more detail below.

As mentioned above, in variations where a catheter comprises an electrode, the catheter may additionally comprise a wire or other conductive structure which may electrically join the electrode to a current or ground source to carry current to or from the electrode. In some variations, as will be described in more detail below, one or more portions of the wire or conductive structure may act as an electrode for ablating tissue. A wire may be disposed inside the catheter, outside the catheter, or a combination thereof. In some variations where the wire is disposed externally to the catheter, the wire may be embedded in the wall of the catheter, attached along an external surface of the catheter, and/or at least partially covered by a sheath or another non-conductive material (such as one or more nesting materials as described in more detail above). For example, in the variation of catheter (100) shown in FIGS. 1A-1C and described in more detail below, wire (104) may at least partially be located along the external surface of the catheter. As shown there, wire may further be shielded from surrounding tissue by sleeve (106).

In other variations, the wire may be at least partially disposed within the catheter. In some of these variations, the wire may comprise a concentric electric conductor which may be disposed around one or more portions of the device. For example, in the variation of catheter (300) shown in FIG. 3 and described in more detail above, concentric electric conductor (314) may be connected to electrode (310). As shown there, concentric electric conductor (314) may be disposed around a portion of lumen (308). Concentric electric conductor (314) may or may not be a braided material, and may be made of any suitable conductive material, such as copper, gold, platinum, and the like.

In some variations, the wire may be electrically insulated by a non-conductive material, such as parylene, ceramic, polytetrafluroethylene, polyetheretherketone, fluorinated ethylene-propylene, or the like. Electric insulation may serve a number of useful purposes. In some instances, the insulation may help prevent current loss from the wire. In other instances, the insulation may protect the wire from inadvertently contacting tissue or other components of the device. It should be appreciated that any of the catheters described here may comprise any electrode or combination of electrodes, any wire or conductive material, and/or any insulating or nesting materials as described above.

The wire may be operatively connected to one or more generators for supplying RF energy to the electrode. The generator may supply any suitable current to the electrodes that is capable of ablating tissue. In some variations, the generator may be configured to supply power between about 10 W and about 300 W. In other variations, the generator may be configured to supply power between about 100 W and about 200 W. In some variations, the generator may be configured to generate a pulsed current. In some of these variations, the amplitude of the pulsed current may vary between pulses. In other variations the generator may be configured to generate an alternating current. In these variations, one or more electrodes may be attached to the bipolar or monopolar outputs of the generator, as described in more detail above. In variations where the generator is configured to generate an alternating current, the current may have any suitable frequency range, such as, for example about 300 kHz to about 9.5 MHz. It should also be appreciated that the generator may be configured to provide a plurality of power outputs. For example, in some variations a generator may be configured to supply a first output to fuse blood vessel tissue (as will be described in more detail below), and may be configured to supply a second output to ablate or vaporize tissue.

As mentioned above, one or more portions of a lead wire may act as an electrode for ablating or vaporizing tissue. For example, FIGS. 21A and 21B show one such variation of catheter (2100). As shown there, catheter (2100) comprises a distal catheter body (2102), proximal catheter body (2104), nesting material (2106) comprising coupling magnets (2108) and track (2110), and lead wire (2112). In these variations, at least a portion of lead wire (2112) may be uncovered (e.g., not electrically isolated via one or more insulating coatings, nesting materials, or other non-conductive materials), such that the exposed portion of the lead wire (2112) may act as an ablation surface from which current may be delivered to ablate, vaporize or otherwise remove tissue. Additionally, a distal portion of lead wire (2112) may be biased away from the catheter (2100), and may be moveable between three positions. In a first position (not shown), the lead wire (2112) may be held or otherwise housed within the catheter (2100), which may allow for low-profile advancement of the catheter (2100) through the vasculature. The lead wire (2112) may then be advanced (or in some instances, withdrawn) such that the bias of the lead wire (2112) causes a distal portion of the lead wire (2112) to project out of catheter (2100) through track (2110), as shown in FIG. 21A. In some instances, this bias may urge or otherwise press the lead wire (2112) against blood vessel tissue (not shown). A current may then be supplied to lead wire (2112) to ablate blood vessel tissue. As blood vessel tissue is ablated, the bias of the lead wire (2112) may continue to urge the distal portion of the lead wire (2112) through tissue, where it may come into contact with one or more portions of a second catheter (such as, for example, an electrode comprising a flat ablation surface such as those described above) in an adjoining blood vessel. Additionally, the lead wire (2112) may be further advanced (or withdrawn) during ablation to move the lead wire (2112) to a second position, as shown in FIG. 21B. As the lead wire (2112) is moved, it may move across blood vessel tissue to ablate a tract or path in the tissue, which may facilitate formation of the fistula. Following ablation, the lead wire (2112) may then be returned to its original low-profile configuration (or a different low-profile configuration), and the catheter may be repositioned or removed.

Figure 31A:
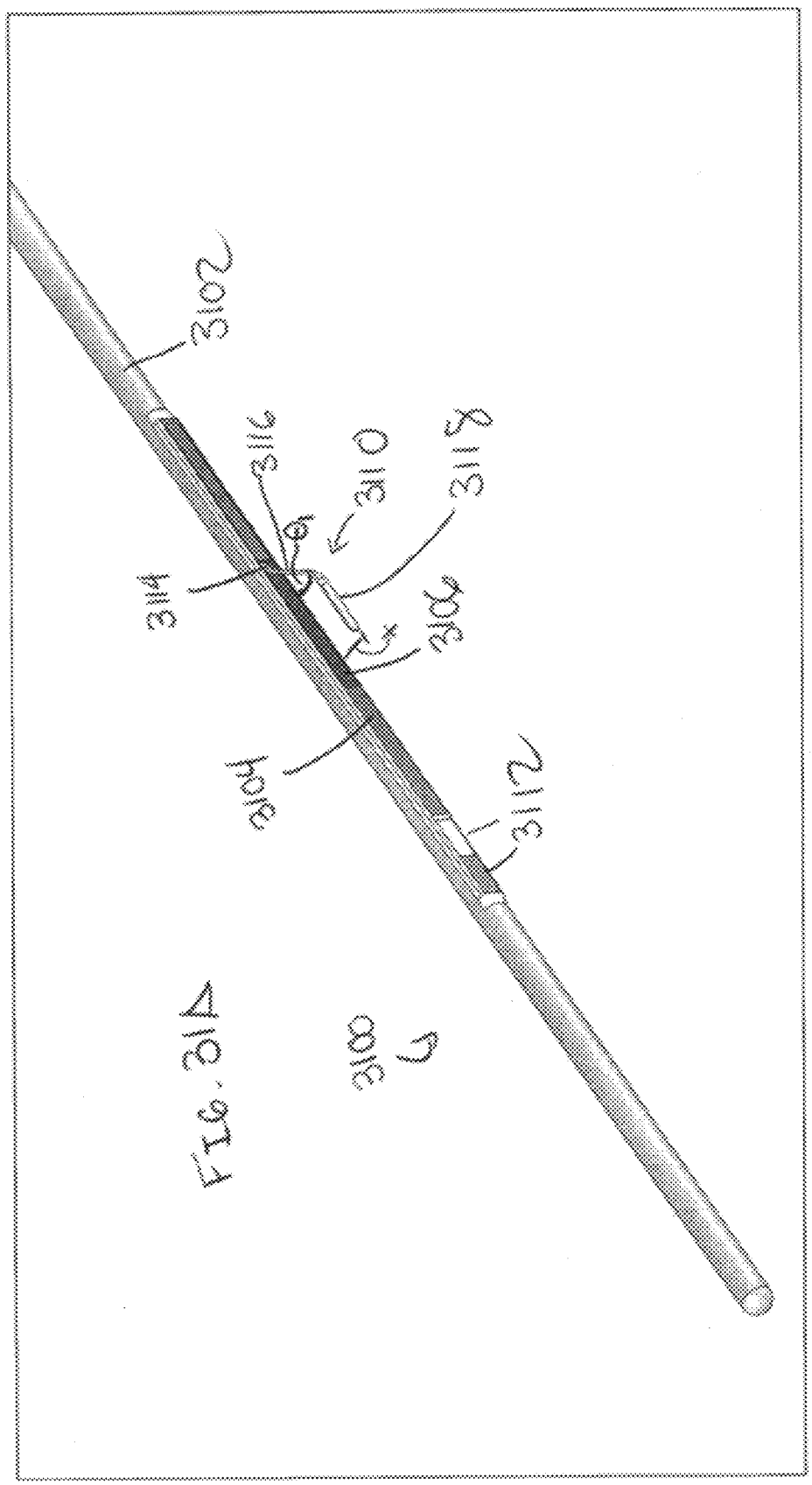

FIGS. 31A and 31B illustrate another variation of catheter (3100). Specifically, FIG. 31A shows a perspective view of catheter (3100), comprising catheter body (3102), nesting material (3104) with track (3106), coupling magnets (3108), and shaped lead wire (3110). FIG. 31B shows catheter (3100) with catheter body (3102) removed. Additionally shown in FIG. 31B are anchoring magnets (3112). Similar to the lead wire (2112) described above in relation to FIGS. 21A and 21B, at least a portion of lead wire (3110) may be uncovered and thus may act as an ablation surface to ablate or vaporize tissue. Additionally, the distal portion of lead wire (3110) may be configured to bias away from the catheter (3100), and may be moveable between three positions. In the first position (not shown), the lead wire (3110) may be held or otherwise housed within the catheter (3100) (e.g., within nesting material (3104) and/or catheter body (3102)), which may allow for low-profile advancement of the catheter (3100) through the vasculature. The lead wire (3110) may then be withdrawn (or in some instances, advanced) such that the bias of the lead wire (3110) may cause the distal portion of lead wire (3110) to bias away from catheter body (3102), as shown in FIGS. 31A and 31B. As illustrated there, lead wire (3110) may comprise a first segment (3114) housed at least partially within catheter body (3102), a first angled segment (3116) extending from a distal end of the first segment (3114), and a second angled segment (3118) extending from a distal end of the first angled segment (3116). First angled segment (3116) may extend from first segment (3114) at a first angle ($\theta_1$), such that when lead wire (3110) biases away from catheter body (3102), first angled segment (3116) angles away from catheter body (3102) at first angle ($\theta_1$). First angle ($\theta_1$) may be any suitable angle (e.g., about 30 degrees, about 45 degrees, about 60 degrees, between about 30 degrees and about 60 degrees, between about 15 degrees and about 75 degrees, or the like). Second angled segment (3118) may be angled relative to first angled segment (3116) at a second angle ($\theta_2$). Second angle ($\theta_2$) may be any suitable angle (e.g., about 100 degrees, about 135 degrees, about 170 degrees, between about 100 degrees and about 170 degrees, or the like). In the variation shown in FIGS. 31A and 31B, lead wire (3110) may be configured such that when lead wire (3110) biases second angled portion (3118) is approximately parallel to the longitudinal axis of catheter body (3102), and separated from the catheter body (3102) by a distance (x). Distance (x) may be any value suitable to extend at least partially through vascular tissue during ablation (e.g., less than 1 mm, between about 1 mm and about 2 mm, between about 1 mm and about 3 mm, greater than about 4 mm, and the like).

When catheter (3100) is placed inside of a blood vessel (not shown) and lead wire (3110) extends out from catheter (3100), the first (3116) and second (3118) angled sections of the lead wire (3110) may be biased into tissue of the blood vessel. When lead wire (3110) is used to ablate tissue, this bias may cause lead wire (3110) to press through or otherwise ablate blood vessel tissue. As lead wire (3110) passes through blood vessel tissue, it may come into contact with one or more portions of a second catheter (not shown) placed in an adjoining blood vessel, as will be described in more detail below. In some variations, the lead wire (3110) may be further withdrawn (or advanced) during ablation to slide the lead wire (3110) relative to the catheter into a third position (not shown). As the lead wire (3110) is moved, it may move across blood vessel tissue to ablate a tract or path in the tissue, which may facilitate formation of the fistula. Following ablation, the lead wire (3110) may then be returned to a low-profile (e.g., by withdrawing the lead wire (3110) relative to the catheter body (3102)), and the catheter may be repositioned or removed.

One or more portions of lead wire (3110) may be coated over otherwise covered with one or more insulating materials. For example, as shown in FIGS. 31A and 31B, an insulating material (3122) may at least partially cover lead wire (3110). Insulating material may cover any suitable portion or portions of lead wire. For example, in the variation shown in FIGS. 31A and 31B, an insulating material (3122) may cover first segment (3114) and first angled segment (3116), but not second angled segment (3118). In other variations, the insulating material (3122) may cover the first segment (3114) and only partially cover the first angled segment (3116), such that the second angled segment (3118) and a portion of the first angled segment (3116) remain uncovered. In these variations, the second angled segment (3118) and uncovered portion of the first angled segment (3116) may act as an ablation surface. When insulating material (3122) covers multiple segments of lead wire (3110), the same material may cover each segment, or different insulating materials may cover the different segments. Insulating material (3122) may comprise any suitable material or materials, such as those described above. In some variations, insulating material (3122) may comprise polyetheretherketone.

FIG. 32 shows another variation of catheter (3200) comprising a lead wire (3202) having a first segment (3204), a first angled segment (3206), and a second angled segment (3208). As shown there, catheter (3200) may comprise a catheter body (3210) having a recessed region (3212). Catheter (3200) may comprise a lumen (3214) or other passageway extending through catheter body (3210). Lumen (3214) may extend through catheter body (3210) both proximally and distally of recessed region (3212), or may only extend through catheter body (3210) only proximally of recessed region (3212). As with lead wire (3110) described above in relation to FIGS. 31A and 31B, at least a portion of lead wire (3202) be uncovered, and lead wire (3202) may be moveable from a low-profile configuration and a biased configuration in which first angled segment (3206) angles away from first segment (3204) and catheter body (3210). When in a low-profile configuration, the first (3206) and second (3208) angled segments may be at least partially constrained within lumen (3214). In some variations, at least a portion of first angled segment (3206) and/or second angled segment (3208) may be temporarily housed in a portion of lumen (3214) distally of recessed region (3212). In these variations, lead wire (3202) may be withdrawn relative to catheter body (3210) to release first angled segment (3206) and second angled segment (3208) from lumen (3214), which may allow these segments to bias away from catheter body (3210) as described above. In other variations, at least a portion of first angled segment (3206) and/or second angled segment (3208) may be temporarily housed in a portion of lumen (3214) proximally of recessed region (3212). In these variations, the lead wire (3202) may be withdrawn to release first angled segment (3206) and second angled segment (3208) from lumen (3214).

As shown in FIG. 32, an insulating material (3216) (such as one or more of the insulating materials described above) may cover first segment (3204) and may partially cover first angled segment (3206), leaving second angled segment (3208) and a portion of first angled segment (3206) exposed. In some variations, one or more insulating materials may also partially cover second angled segment (3208), but need not. The exposed portions of first (3206) and second (3208) angled segments may act as an ablation surface to ablate or vaporize tissue. Catheter body (3210) may also comprise one or more insulating nesting materials (not shown) or coatings which may help protect the catheter body (3210) from and in some instances redirect heat and energy produced by lead wire (3202) during ablation.

Additionally, in some variations, the lead wire (3202) may be further withdrawn (or advanced) during ablation to slide the lead wire (3202) relative to the catheter. As the lead wire (3202) is moved, it may move across blood vessel tissue to ablate a tract or path in the tissue, which may facilitate formation of the fistula. Following ablation, the lead wire (3202) may then be returned to a low-profile, for example, by withdrawing the lead wire (3202) such that first angled segment (3206) and second angled segment (3208) are pulled into lumen (3214).

As mentioned above, in some variations one or more portions of an ablation surface of an electrode of a first catheter may extend or otherwise be advanced through blood vessel tissue during ablation. When a second catheter is placed in an adjoining blood vessel, this advancement through blood vessel tissue may cause the ablation surface to contact one or more portions of the second catheter. When the second catheter comprises an electrode having an exposed conductive surface, direct contact between the electrodes of each catheter may cause the energy source (e.g., an electrosurgical generator) to shut off or otherwise cease tissue ablation. In other instances, contact between the electrode of the first catheter and the second catheter may damage one or more components of the second catheter. Accordingly, in some variations it may be desirable to configure a catheter to include one or more sections that may accommodate contact with an active electrode without ceasing ablation or otherwise damaging one or more portions of the catheter.

FIGS. 33A and 33B show one such variation of a catheter (3300). As shown there in FIG. 33A, catheter (3300) may comprise a catheter body (3302), nesting material (3304) with pocket (3306), coupling magnets (3308), and electrodes (3310). FIG. 33B shows catheter (3300) with catheter body (3302) removed. Additionally shown there are anchoring magnets (3312). Generally, pocket (3306) may be configured to receive a portion of an electrode from a second catheter. For example, when catheter (3300) is placed within a blood vessel (not shown), and a second catheter is placed in an adjoining blood vessel, catheter (3300) may be positioned relative to the second catheter such that pocket (3306) may be aligned with an electrode (not shown) of the second catheter. Alignment may result from attraction between alignment elements of catheter (3300) (e.g., coupling magnets (3308) and/or anchoring magnets (3312) and corresponding alignment elements of the second catheter, as will be described in more detail below. During ablation, the electrode of the second catheter may pass between the blood vessels, where it may be received by pocket (3306). Nesting material (3304) may be formed from or coated with an insulating material, such that energy delivered by the electrode does not damage catheter (3300) as electrode is received by pocket (3306).

Pocket (3306) may be configured to receive any suitable electrode, as described in more detail above. For example, in some variations, pocket (3306) may be configured to receive a portion of a lead wire, such as wire (2112) of catheter (2100) describe above in relation to FIGS. 21A and 21B, lead wire (3110) of catheter (3100) described above with respect to FIGS. 31A and 31B, lead wire (3202) described above in relation to FIGS. 32A and 32B, or the like. For example, in some variations, the coupling magnets and anchoring magnets of catheters (3300) and (3100) may be configured such that when catheters (3300) and (3100) are placed in adjoining blood vessels, the pocket (3306) of catheter (3300) may be substantially aligned relative to track (3106). When lead wire (3110) is advanced (or withdrawn) such that a distal portion of the lead wire (3110) is biased out of track (3106), lead wire (3110) may be activated to ablate vessel tissue, as described in more detail below. As lead wire (3110) ablates through tissue, one or more portions of the lead wire (3110) (e.g., second angled portion (3118))) may enter or otherwise be received by the pocket (3306).

While shown in FIGS. 33A and 33B as having electrodes (3310), catheter (3300) need not comprise any electrodes. In variations that do include electrodes (3310), electrodes (3310) may act as a passive ground electrode for an active electrode of a second catheter (e.g., lead wire (3110) of catheter (3100) described above) or vice versa, which may aid in tissue ablation. While shown in FIGS. 33A and 33B as having two electrodes (3310), it should be appreciated that the catheters described here may comprise any suitable number of electrodes (e.g., zero, one, two, or three or more electrodes). For example, FIG. 34 illustrates one such variation of a catheter (3400) comprising a single electrode (3402). Also shown there are catheter body (3404) and nesting material (3406) with pocket (3408) and housing electrode (3402) and coupling magnets (3410). Pocket (3408) may be configured to receive one or more portions of an electrode of a second catheter, as described in more detail above. While electrode (3402) is proximal to pocket (3408) in the variation of catheter (3400) shown in FIG. 34, in other variations electrode (3402) may be positioned distal to pocket (3408).

In some variations, a catheter may comprise a pocket formed in an electrode. FIGS. 35A and 35B show one such variation of catheter (3500). As shown in FIG. 35A, catheter may comprise a catheter body (3501) and nesting material (3502). Nesting material (3502) may house electrode (3504) and coupling magnets (3506) therein. FIG. 35B shows catheter (3500) with catheter body (3501) removed, and further shows anchoring magnets (3510). Pocket (3508) may be formed in electrode (3504), and may be configured to receive a portion of an electrode from a second catheter. In some variations, pocket (3508) may be electrically and/or thermally insulated by depositing one or more insulating coatings (e.g., a refractory metal oxide coating) onto the surfaces of pocket (3508), which may allow pocket (3508) to receive and contact at least a portion of an electrode without pocket (3508) providing a direct electrical connection. In other variations, pocket (3508) may be configured to allow for electrical conduction therethrough without direct physical contact with an external electrode. For example, in some of these variations, pocket (3508) may be covered or otherwise coated with a porous insulating coating (e.g., a porous metal oxide coating). When pocket (3508) receives an electrode (e.g., one or more of the lead wire electrodes described above), the porous coating may allow for electrical conduction through the pocket (3508) without direct electrode-to-electrode physical pocket, which may prevent short-circuiting or interruption of ablation.

Additionally, while the variations of catheters described immediately each comprise a pocket for receiving an electrode from a second catheter, it should be appreciated that the catheters described here need not comprise a pocket. Indeed, in some variations one or more portions of the device may be electrically insulated or partially electrically insulated to allow for direct contact with one or more electrodes of a second catheter. For example, FIG. 36 illustrates one such variation of catheter (3600). As shown there, catheter (3600) may comprise a catheter body (3602) and a nesting material (3604). Nesting material (3604) may house an electrode (3606) and coupling magnets (3608) therein. Electrode (3606) may further comprise one or more coated segments (3610). Coated segment (3610) may comprise an insulating coating (as described in more detail above) or a partially-insulating coating (e.g., a porous coating as described immediately above). Catheter (3600) may interact with a second catheter (not shown), such that when the catheters are placed in adjoining blood vessels, an electrode of the second catheter may extend through vessel tissue during ablation and contact coated segment (3610) without damaging or short-circuiting the device. While the coated segment (3610) of electrode (3606) may be recessed relative to the remainder of the electrode, it should also be appreciated that in some variations the coated segment (3610) may be flush relative to the uncoated portions of the electrode (3606)

Mechanical Cutting Elements

In some variations, a catheter may comprise one or more mechanical cutting elements. For example, in some variations a catheter may comprise a blade that may be advanced or otherwise extended from the catheter to cut or otherwise sever tissue. FIG. 22 shows one such variation of catheter (2200) comprising a nesting material (2201) comprising track (2202) and a blade (2204). Blade (2204) may have any suitable shape and configuration (e.g., single-edge, double-edge, pointed, rounded, or the like). Blade (2204) may be rotatably, translatably, or otherwise coupled to catheter (2200) such that it may be deployed through track (2202) to cut or otherwise sever tissue. In some variations, the blade (2204) may be configured to oscillate relative to catheter (2200) to cut or otherwise sever tissue. Blade (2204) may be deployed by any suitable mechanism (e.g., one or more mechanical actuators, magnet-based actuators, electronic actuators, or the like), and may be withdrawn into track (2202) to allow for low-profile advancement or withdrawal of the catheter. In some variations, as will be described in more detail below, the blade (2204) may be used to pierce or puncture one or more balloons in a corresponding catheter in another blood vessel. Additionally, in some variations, the blade (2204) may electrically connected to an electrosurgical generator such that blade (2204) may act as an electrode, like those electrodes described in more detail above.

Figure 37A:
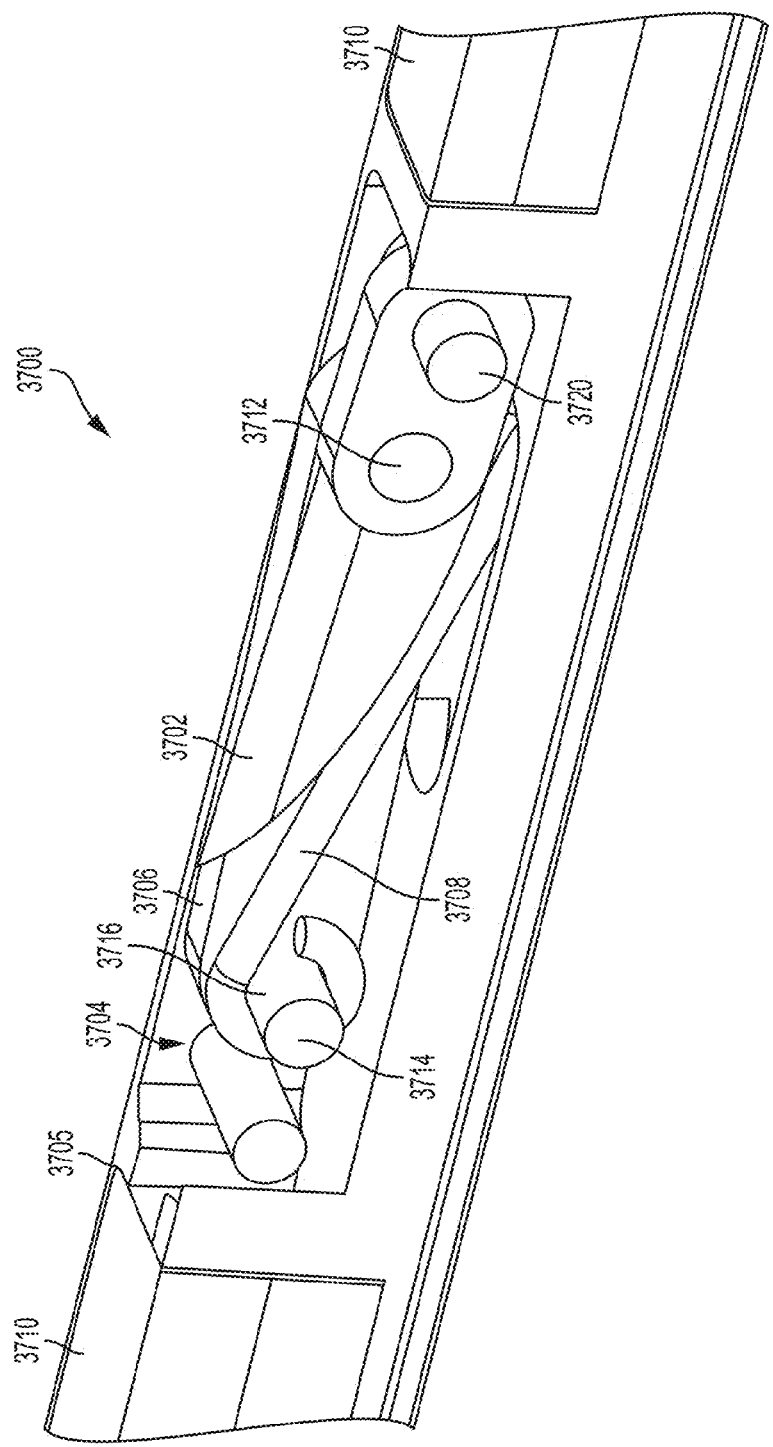

FIGS. 37A and 37B show cross-sectional perspective views of a variation of catheter (3700), and illustrate a mechanism by which a blade (3702) may be advanced out of catheter (3700). Catheter (3700) may comprise a recess (3704) in catheter body (3705). Blade (3702) may be moveable from a low-profile configuration, in which blade (3702) is housed in recess (3704) (as shown in FIG. 37A) to a cutting configuration, in which blade (3702) is advanced out of recess (3704) (as shown in FIG. 37B). Catheter (3700) may comprise a rotation arm (3706) and an activation wire (3708), which may help move blade (3702) between the retracted and cutting configurations, as will be described in more detail below. Also shown in FIGS. 37A and 37B are coupling magnets (3710) located proximal and distal of blade (3702), although it should be appreciated that catheter (3700) need not comprise any alignment element or may comprise any suitable alignment elements or combinations of alignment elements as described in more detail below.

As shown in FIGS. 37A and 37B, rotation arm (3706) may be pivotally connected to blade (3702) at a first pivot point (3712) at or near a first end of rotation arm (3706), and may also be pivotally connected to the catheter body (3705) at a second pivot point (3714) at or near a second end of rotation arm (3706). The pivot points described here may comprise one or more pins, projections, other structures that allow for rotational movement between two members. For example, as shown in FIGS. 37A and 37B, second pivot point (3714) may comprise a pin (3716). In some variations, the second pivot point (3714) may additionally be configured to move along the longitudinal axis of the catheter body (3705). For example, pin (3716) of second pivot point (3714) may be slidably disposed in a track (3718) within catheter body (3705), such that pin (3716) may both rotate and slide relative to track (3718) and catheter body (3705). Blade (3702) may further be pivotally connected to the catheter body (3705) at a third pivot point (3720). Additionally, activation wire (3708) may be connected to rotation arm (3706) at or near its second end. For example, in the variation of catheter (3700) shown in FIGS. 37A and 37B activation wire (3708) may be attached to a portion of pin (3716).

Activation wire (3708) may be manipulated to move blade (3702) between a retracted position (as shown in FIG. 37A) and an extended cutting position (as shown in FIG. 37B). Activation wire (3708) may be pulled proximally relative to the longitudinal axis of the catheter (3702), which may cause second pivot point (3714) to slide proximally relative to the catheter body. As second pivot point (3714) moves proximally toward third pivot point (3720), the rotation arm (3706) and blade (3702) may each rotate away from catheter body (3705), as shown in FIG. 37B. When catheter (3700) is placed in a blood vessel, rotation of blade (3702) into a cutting position may cause blade (3702) to cut or otherwise sever vessel tissue. To return blade (3702) to a retracted position, the activation wire (3708) may be advanced distally relative to the catheter (3700), which may move second pivot point (3714) away third pivot point (3720), which may cause rotation arm (3706) and blade (3702) to rotate back toward the catheter body. It should also be appreciated that in some variations, catheter (3700) may be configured such that distal advancement of the activation wire causes rotation arm (3706) and blade (3702) to rotate blade to an extended position, while proximal withdrawal of the activation wire causes rotation arm (3706) and blade (3702) to rotate blade (3702) to a retracted position.

Figure 38A:
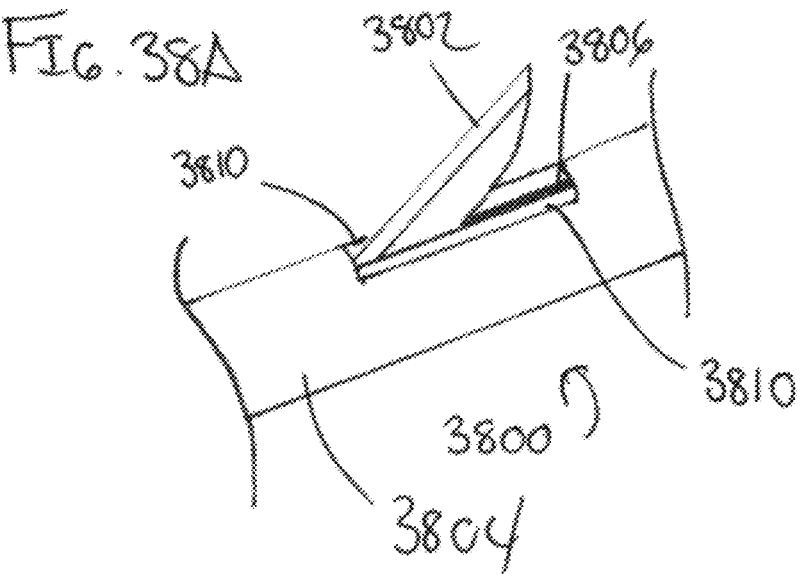
FIGS. 38A and 38B depict a perspective view and a cross-sectional side view, respectively, of a variation of a catheter comprising a blade.
Figure 38B:
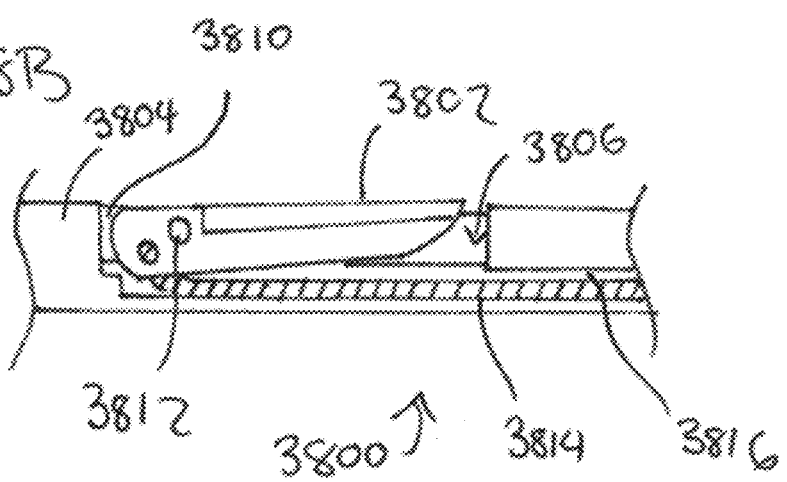

FIGS. 38A and 38B depict another variation of a catheter (3800) comprising a blade (3802). As shown in a perspective view in FIG. 38A, catheter (3800) may comprise a catheter body (3804), and a recess (3806) in catheter body (3804) through which blade (3802) may extend. Also shown there are guide plates (3810) on both sides of recess (3806), and activation wire (3814). FIG. 38B shows a cross-sectional side view taken along the longitudinal axis of catheter (3800). As shown there, blade (3802) may be pivotally attached to one or more of guide plates (3810) at pivot point (3812). In some variations, the pivot point (3812) may comprise one or more pins or projections, as described immediately above.

As shown in FIG. 38B, a distal portion of activation wire (3814) may be attached to blade (3802), and may extend through a lumen (3816) or other passageway in the catheter body (3804). A proximal portion of activation wire (3814) may be manipulated to withdraw or advance activation wire (3814) within lumen (3816), and this movement may cause blade (3802) to rotate relative to pivot point (3812). In the variation shown in FIGS. 38A and 38B, withdrawal of the activation wire (3814) may cause the blade (3802) to rotate outwardly from catheter body (3804) (as shown in FIG. 38A), while advancement of activation wire (3814) may cause blade (3802) to rotate to a retracted position (such as shown in FIG. 38B).

When catheter (3800) is advanced into a blood vessel (not shown), the catheter (3800) may be advanced with blade (3802) in a retracted position within the catheter body (3804). When catheter (3800) is positioned within the blood vessel, a user may withdraw or otherwise retract pull wire to rotate the blade (3802) to an extended position, whereby blade (3802) may cut or otherwise sever tissue. When blade (3802) is in an extended position, catheter may optionally be moved relative to the blood vessel to further cut or otherwise sever tissue. Additionally or alternatively, pivot point (3812) may be moveable relative to the catheter body (3804), such that pivot point (3812) and blade (3802) may be translated along the longitudinal axis of the catheter body (3804). Following the cutting action by the blade (3802), the activation wire (3814) may be advanced to return blade (3802) to a retracted position. Catheter (3800) may optionally be repositioned and reactivated to cut or sever tissue at another location, or catheter (3800) may be removed from the blood vessel. While catheter (3800) is illustrated above as being configured such that withdrawal of activation wire (3814) extends blade (3802) from catheter body (3804) and advancement retracts blade (3802) into catheter body (3804), it should be appreciated that catheter (3800) may be configured such that advancement of activation wire (3814) may extend blade (3802) from catheter body (3804) and withdrawal of the activation wire (3814) may retract blade (3802) into the catheter body (3804).

FIGS. 39A-39C illustrate yet another variation of a catheter (3900) comprising a blade (3902). FIG. 39A shows a perspective view of a portion of catheter (3900) with blade (3902) in an extended position, extending from a recess (3904) in catheter body (3906). FIGS. 39B and 39C show cross-sectional side views of catheter (3900) along its longitudinal axis. As shown there, blade (3902) may be attached to a first wire portion (3908) and a second wire portion (3910). First wire portion may be attached to or otherwise engage a translation wire (3912) at connection point (3914). In some of these variations, first wire portion (3908) and second wire portion (3910) may comprise a shape-memory material, and may be configured such that first wire portion (3908) and second wire portion (3910) bias blade (3902) away from translation wire (3912) and toward an extended position, as shown in FIG. 39C. To move blade (3902) from an extended position to a retracted position, as shown in FIG. 39B, second wire portion (3910) may be pulled away from connection point (3914) in the direction of arrow (3916). This may cause first (3908) and second (3910) wire portions to at least partially straighten, which may withdraw blade (3902) into catheter body (3906). Second wire portion (3910) may be locked or otherwise fixed relative to translation wire (3912) to hold blade (3902) in a retracted position.

To use blade (3902) to aid in forming a fistula, catheter (3900) may be advanced into a blood vessel (not shown) with blade (3902) in a retracted position. Once positioned (e.g., using one or more alignment elements, visualization methods, or the like), blade (3902) may be moved to an extended position. To do this, second wire portion (3910) may be unlocked relative to translation wire (3912), which may allow first (3908) and second (3910) wire portions to return to their outwardly biased positions, thereby extending blade (3902) to an extended position, as shown in FIG. 39C. In some variations, a user may advance or otherwise move second wire portion (3910) toward connection point (3914) to help bias blade (3902) in an extended position. As blade (3902) extends from catheter body (3906) it may cut or otherwise sever tissue. In some variations, second wire portion (3910) may be locked or otherwise fixed relative to translation wire (3912) to hold blade (3902) in an extended position. Once extended from catheter body (3906), translation wire (3912) may be advanced or withdrawn relative to catheter body (3906) to translate blade (3902) along the longitudinal axis of the catheter, which may allow blade (3902) to cut a larger tract of tissue. Additionally or alternatively, catheter (3900) may be advanced or withdrawn relative to the blood vessel with blade (3902) extended to cut a larger tract of tissue. The second wire portion (3910) may then be withdrawn relative to translation wire (3912) and connection point (3914) to return blade (3902) to a retracted position, and the catheter (3900) may be repositioned or removed.

It should be appreciated that the above-described variations of catheters comprising blades may include any of the additional device features described hereinthroughout. For example, the catheters may comprise one or more alignment elements. In these variations, the catheters may comprise one or more anchoring magnets and/or one or more coupling magnets. Additionally or alternatively, the catheter may comprise one or more shape-changing elements and/or one or more markers, as will be described in more detail below.

Laser Energy

In some variations, the catheters described here may be configured to deliver laser energy to tissue to vaporize or otherwise remove tissue during fistula formation. Generally, variations of these catheters may comprise an optical fiber which may run from a proximal portion of the catheter to a distal portion of the catheter. A proximal portion of the optical fiber may operatively connected (e.g., via a SMA connector, or the like) to a laser generator. Laser energy produced by the laser generator may propagate or otherwise pass through the optical fiber, and may be delivered from optical fiber to tissue to vaporize tissue. In some variations the catheter may comprise one or more lenses, mirrors, diffuser, and/or other components which may redirect light from the optical fiber toward tissue.

The laser generator may be configured to produce any suitable laser energy. In some variations, it may be desirable to produce light energy having a wavelength with high water absorption, which may promote energy absorption by vessel tissue. In some variations, the laser generator may be configured to generate infrared energy. Examples of suitable wavelengths include, but are not limited to, about 730 nanometers, between about 680 nanometers and about 780 nanometers, about 820 nanometers, between about 750 nanometers and about 870 nanometers, about 930 nanometers, between about 880 nanometers and about 980 nanometers, about 970 nanometers, between about 920 nanometers and about 1020 nanometers, about 1200 nanometers, between about 1150 nanometers and about 1250 nanometers, about 1450 nanometers, between about 1400 nanometers and about 1500 nanometers, about 1950 nanometers, between about 1900 nanometers and about 2000 nanometers, about 2900 nanometers, between about 2850 nanometers and about 2950 nanometers or the like. Examples of suitable laser generators include, but are not limited to, diode lasers, diode-pumped lasers, Nd-YAG lasers, and the like.

Figure 43:
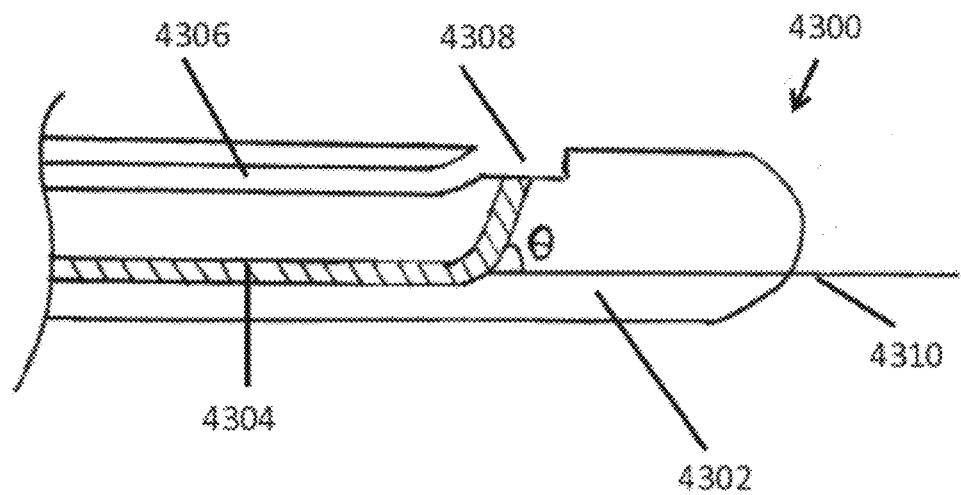
FIGS. 43 and 44 depict variations of catheters comprising optical fibers.

FIG. 43 shows a distal portion of one variation of catheter (4300) which may be configured to deliver laser energy to tissue. As shown there, catheter (4300) may comprise catheter body (4302), optical fiber (4304), and irrigation lumen (4306). As shown there, optical fiber (4304) may run along the longitudinal axis (4310) of catheter body (4302), and a distal portion of the optical fiber (4304) may bend to direct the distal end of the optical fiber (4304) out of a side of the catheter body (4302). The distal portion of the optical fiber (4304) may bend at any angle (θ) relative to the longitudinal axis (4310) of the catheter body (4302). In some variations, angle (θ) may be about 45 degrees. In other variations, angle (θ) may be about 90 degrees. In still other variations, angle (θ) may be between about 45 degrees and about 90 degrees. In yet other variations, angle (θ) may be less than about 45 degrees, or greater than about 90 degrees.

When the distal end of the optical fiber (4304) is directed toward the side of the catheter body (4302), laser energy may be passed through optical fiber (4304) and out the side of catheter body (4302), where it may vaporize, ablate, or otherwise remove tissue. In some variations, it may be desirable to pass a gas (e.g., carbon dioxide) or fluid (e.g., saline) between the distal end of the optical fiber (4304) and tissue during tissue vaporization. Accordingly, in some variations, one or more fluids may be passed through catheter body (4302) via irrigation lumen (4306) and be delivered between the optical fiber (4304) and tissue (not shown). The gas or fluid may be introduced continuously or intermittently during tissue vaporization, and may help to minimize or otherwise prevent excessive heating or damage to surrounding tissue.

Additionally, in some variations, it may be desirable to space the output of the optical fiber (4304) from tissue. In some instances, spacing the output of the optical fiber from tissue may affect the power density of the laser energy provided and/or the size of the fistula formed. In some variations, the catheter may comprise a space (4308) between the end of the optical fiber (3404) and the side wall of the catheter body (4302). Space (4308) may separate the end of the optical fiber (3404) from the side wall of the catheter body (4302) by any suitable amount (e.g., about 0.5 mm, about 1 mm, about 1.5 mm, between about 0.5 mm and about 1.5 mm, greater than about 1.5 mm, and the like). Additionally, in variations where an irrigation lumen (4306) is used to deliver a gas or fluid between the output of the optical fiber (4304) and tissue, gas or fluid may be delivered into or through space (4308).

Figure 44:
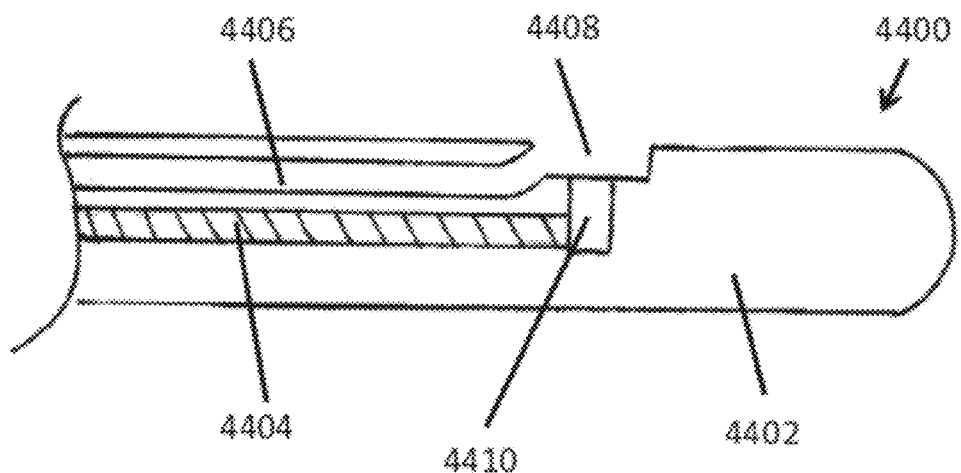

As mentioned above, in some variations, a catheter may comprise one or more lenses, diffusers, mirrors, or the like, for altering or otherwise redirecting light passing through an optical fiber. For example, FIG. 44 shows one variation of a catheter (4400) comprising a diffuser (4410) which may redirect laser energy provided through an optical fiber (4404). As shown there, catheter (4400) may comprise a catheter body (4402), an irrigation lumen (4406), optical fiber (4404), and diffuser (4410). Diffuser (4410) may be attached at or near the distal end of the optical fiber (4404), and may redirect light from optical fiber (4404) out of the side of catheter body (4402). In some variations, a space (4408) within catheter body (4402) may separate an output of diffuser (4410) from tissue. Additionally, irrigation lumen (4406) may be positioned to pass fluid between diffuser (4410) and tissue (not shown), as described immediately above.

Alignment Elements

In some variations, the catheters described here may comprise one or more alignment elements to help align or otherwise reposition the catheters when placed in the vasculature. For example, in some instances alignment elements may help bring two or more catheters (and with them, two or more blood vessels) in closer approximation. In other instances, the alignment elements may help ensure that one or more catheters are in proper axial or rotational alignment relative to another catheter (or catheters). Ensuring proper position of catheters and blood vessels may help facilitate formation of a fistula with one or more of the fistula-forming elements described above. In some variations, catheters may comprise mechanical alignment features, such as protrusions, grooves, flat surfaces, and the like, that may or may not interact with one or more alignment features on another catheter. Additionally or alternatively, a catheter may have one or more magnetic components that may interact with one or more magnetic components of another catheter or one or more magnets positioned externally from the body. In still other variations, the catheter may comprise one or more markers that may help a user to align one or more catheters. In still other variations, a catheter may comprise one or more shape-changing members for adjusting the positioning of a catheter. It should be appreciated that each catheters described here may comprise any alignment element or combination of alignment elements described below, and in variations where the catheter comprises a fistula-forming element, may comprise any fistula forming element or combination of elements described in more detail above.

Magnets

As mentioned above, a catheter may comprise one or more magnetic alignment components. These magnetic alignment components may be attracted to one or more additional elements (e.g., one or more portions of a second catheter, one or more magnets or other components placed externally from the body) to help position or align the catheter within a vessel. For example, one or more magnets placed outside of the body may interact with the magnetic alignment components of a catheter to help facilitate advancement of the catheter through the vasculature, as will be described in more detail below. In other instances, a catheter may comprise one or more "anchoring" magnetic alignment elements that act to attract the catheter toward one or more portions of a second catheter, thereby bringing the catheters in closer approximation. In other variations, a catheter may comprise one or more "coupling" magnetic alignment elements, which may act to rotationally (and/or axially) orient and/or mate a surface of the catheter with one or more surfaces or portions of a second catheter.

A catheter may comprise any number of individual magnets (e.g., zero, one, two, three, four, five, six, seven, or eight or more, etc.). Each magnetic component may be any suitable magnet or magnetic material. For example, in some variations, a catheter may comprise one or more rare-earth magnets (e.g., neodymium magnets or samarium-cobalt magnets) and/or one or more selectively-activated electromagnets. In variations where a catheter comprises a plurality of magnets, these magnets may be grouped into one or more arrays. These magnetic arrays may located inside or outside of a catheter (or a combination thereof), and may be positioned anywhere along the length of the catheter. When two or more catheters comprise magnets or magnet arrays, each magnet or magnet array may be configured or arranged to align with one or more magnets or magnet arrays from a second catheter. Each magnet may be fixed in or on a catheter by any suitable method. For example, in some variations one or more magnets may be embedded in, adhered to or friction fit within a catheter. Each magnet may have any suitable diameter (e.g., about 0.075 in., about 0.080 in., about 0.029 inch, about 0.110 inch, or the like) or length (e.g., about 5 mm, about 10 mm, about 15 mm, about 20 mm, or the like), and may be separated from adjoining magnets by any suitable distance (e.g., about 1 mm, about 5 mm, and the like). In some variations, the magnets of an array may have alternating polarity (e.g., each magnet will have the opposite polarity as any adjacent magnets), matching polarity, or combinations thereof. In other variations, one or more portions of the catheter may be made from a magnetic material, and/or may be embedded with one or more magnetic particles/materials.

Each magnet may have any suitable shape for placement inside or outside of the catheter. Magnets may be cylindrical, semi-cylindrical, tube-shaped, box-shaped, or the like. For example, in the variation of catheter (200) shown in FIG. 2 and described in more detail above, catheter (200) may comprise a proximal anchoring magnet array (206) and a distal anchoring magnet array (208), the magnets of each of which are cylindrical. Alternatively, in the variation of catheter (600) shown in FIG. 6A, catheter (600) may comprise a proximal anchoring magnet array (604) and a distal anchoring magnet array (606), the magnets of each of which are semi-cylindrical. In these variations, a lumen and/or lead wire (such as lumen (608) and lead wire (605)) may pass by or along the anchoring magnet arrays, because the semi-cylindrical magnets only take up a portion of the interior of catheter (600).

While the magnets of proximal (604) and distal (606) magnet assemblies are shown in FIG. 6A as being configured such that the apex of each semi-cylinder is aligned with ablation surface (603), it should be appreciated that the magnets may be positioned in any manner relative to a fistula forming component. For example, FIG. 6B shows another variation of catheter (610) comprising electrode body (612) having ablation surface (613), proximal anchoring magnet array (614), distal anchoring magnet array (616), lead wire (615) and lumen (618). In this variation, the apex of each magnet of the proximal (614) and distal (616) anchoring magnet arrays may be perpendicular to ablation surface (613). Altering the orientation of the magnets relative to the ablation surface (613) may affect the strength of the magnetic force between catheter (610) and another catheter (not shown) when placed in a blood vessel. It should be appreciated that each individual magnet or anchoring magnet array may have any rotational positioning relative to ablation surface (613), which may or may not be the same as the rotational position as another magnet or array of magnets.

In some variations, one or more magnets may have one or more lumens or passageways therethrough, which may allow one or more other components (e.g., a lead wire, actuation mechanism, lumen, combinations thereof and the like) of catheter to pass through the magnets. For example, in the variation of catheter (300) shown in FIG. 3, catheter (300) comprises proximal and distal anchoring magnet arrays ((302) and (304) respectively) having tube-shaped magnets. As shown there, concentric electrical conductor (314) may pass through the magnets of proximal anchoring magnet array (302), and lumen (308) may pass through the magnets of the proximal and distal anchoring magnet arrays ((302) and (304) respectively).

In some variations, one or more magnetic alignment components may comprise one or more box-shaped magnets (e.g., a magnet with a substantially rectangular cross-section). FIG. 23 shows one such variation of catheter (2300). Shown there is tip (2302), distal anchoring magnet array (2304), proximal anchoring magnet array (2306), and nesting material (2308) comprising coupling magnets (2310), electrode body (not shown) with ablation surface (2312) and marker (2316). Catheter (2300) further comprises a catheter body (or a plurality of catheter segments, such as those described above), but the catheter body is not illustrated in FIG. 23 so as to highlight the internal components of catheter (2300). Additionally, while shown in FIG. 23 as comprising coupling magnets (2310) and marker (2316) (each of which will be described in more detail below), catheter (2300) need not.

As shown in FIG. 23, distal anchoring magnet array (2304) comprises a cylindrical anchoring magnet (2318) and a box-shaped anchoring magnet (2314), while proximal anchoring magnet array (2306) comprises a box-shaped anchoring magnet (2314). It should be appreciated that the anchoring magnet arrays may have any suitable combination of magnets, such as one or more of the magnets described above. In variations that comprise one or more box-shaped magnets, such as box-shaped magnets (2314) of catheter (2300), the box-shaped magnets may help bring the catheter in closer approximation with a second catheter, but may also help rotationally orient the catheter relative to the second catheter. Specifically, when two box-shaped magnets are associated with separate catheters, the attractive strength between the two magnets may be greatest when the magnets are aligned. For example, in the variation of catheter (2300) shown below, a front surface (2320) of box-shaped magnet (2314) may align with a front surface of another box-shaped magnet (not shown) of a catheter in another blood vessel. Specifically, the attractive force between the magnets may be greatest when the front surfaces are aligned with each other, and thus the magnets may naturally rotate or facilitate rotation to the aligned position.

In variations where a catheter comprises a nesting material, the nesting material may house one or more coupling magnets for temporarily magnetically coupling a surface or portion of the nesting material to one or more portions of another catheter or device. Specifically, the coupling magnets may be configured such that the attractive force between two catheters is greatest when a surface of each catheter is aligned with the other. For example, in the variation of catheter (2300) shown in FIG. 23 above, nesting material (2308) comprises coupling magnets (2310). In these instances, the longitudinal axis of the coupling magnets (2310) may be substantially transverse to the longitudinal axis of the catheter. Additionally, coupling magnets (2310) may have a flat mating surface which may attract a flat mating surface of a coupling magnet of another catheter (not shown). As described in more detail above in regards to flat ablation surfaces, the flat mating surfaces of a coupling magnet may act to flatten tissue between two catheters, which may aid in ablation by the ablation surface.

Figure 24A:
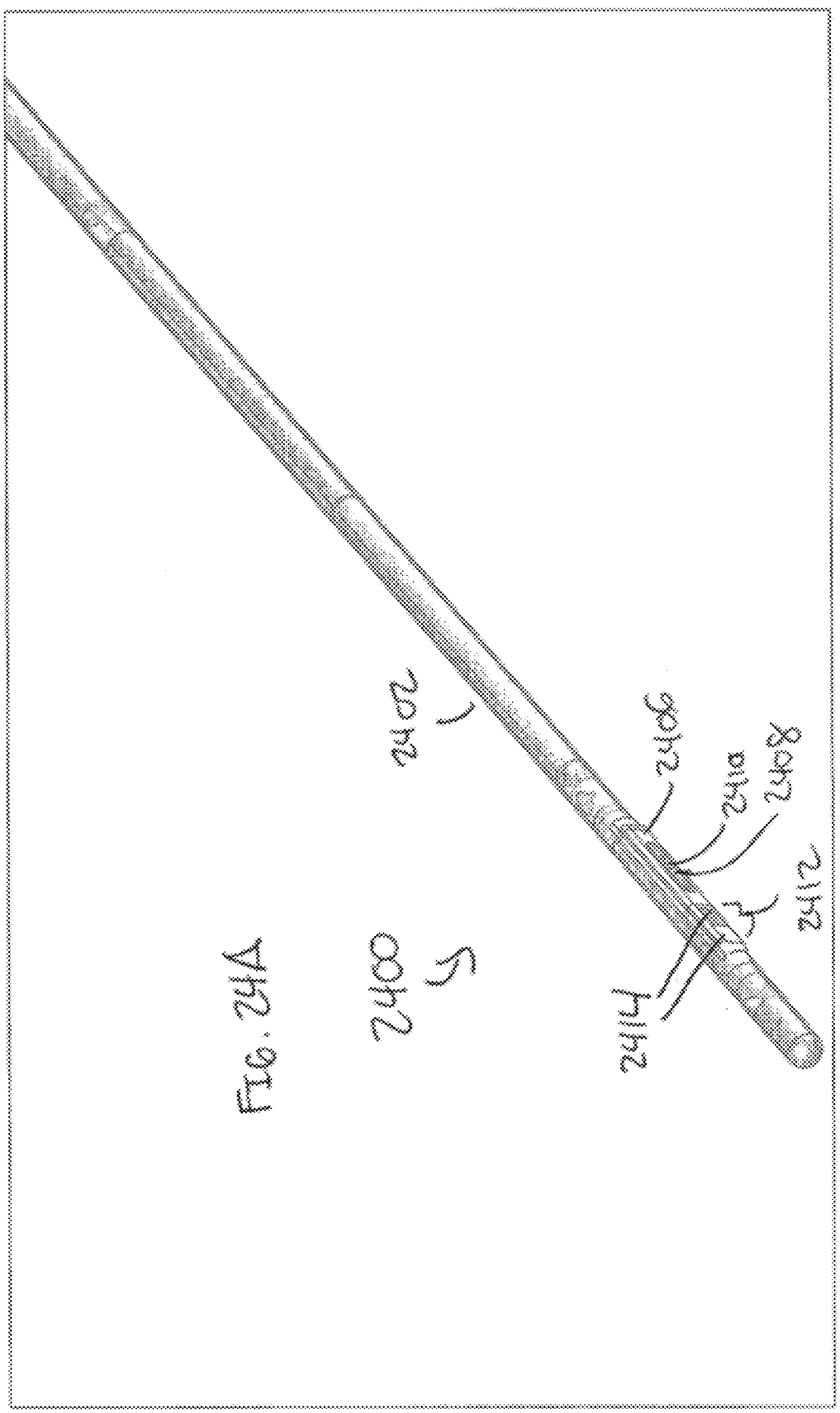

While nesting material (2308) is shown in FIG. 23 as housing a single coupling magnet (2310) on either side of ablation surface (2312), it should be appreciated that a catheter may comprise any suitable number of coupling magnets. FIGS. 24A and 24B show two such variations of catheters comprising coupling magnets. FIG. 24A shows a first variation of catheter (2400). Shown there is catheter body (2402) and nesting material (2406) housing an electrode (2408) and a distal coupling magnet array (2412), wherein the electrode (2408) comprises ablation surface (2410). While shown in FIG. 24A as comprising two coupling magnets (2414), distal coupling magnet array (2412) may comprise any suitable number of coupling magnets (2414) (e.g., one, two, or three or more). In other variations, a nesting material may comprise a plurality of coupling magnet arrays. For example, FIG. 24B shows a variation of catheter (2416) comprising catheter body (2418), nesting material (2420) housing electrode (2422) with ablation surface (2424), proximal coupling magnet array (2426) and distal coupling magnet array (2428). Each of the coupling magnet arrays may comprise any suitable number of coupling magnets (2430), as mentioned immediately above.

In some variations, such as catheters (2400) and (2416) described above in relation to FIGS. 24A and 24B, the catheter may be configured that a fistula-forming element may be placed in close proximity to the distal end of the catheter body. These variations may find particular utility when it is desirable to form a fistula near a tissue structure, blockage, or other impediment that limits the ability of the blood vessels to be brought in closer approximation.

In variations where a catheter comprises an array of electromagnets, the electromagnets may be independently activated or may be activated as a group. For example, electromagnets of a magnet array may be activated one at a time to help ensure a certain alignment orientation with respect to another magnetic device, e.g., proximal magnets may be activated prior to activating distal magnets, every other magnet may be activated in sequence, etc. Alternatively, two or more magnets may be activated simultaneously to promote secure attachment to another magnetic device.

Shape-Changing Elements

In some variations, the catheter may comprise one or more shape-changing elements for approximating two or more blood vessels. In these variations, the shape-changing element may have a first configuration during advancement of the catheter through the vasculature. Once the catheter reaches a target location, the shape-changing element may be altered to a second configuration, which may alter the overall shape of the catheter. As the catheter changes shape, the catheter may move or reconfigure one or more portions of the blood vessel, which may help bring that portion or portions of the blood vessel in closer approximation to one or more portions of a second blood vessel. The shape of a catheter may be altered in any suitable manner. In some variations, a catheter may comprise one or more pull wires, which may pulled or push to deflect or otherwise alter the shape of the catheter. In other variations, a catheter may comprise one or more shaped wires which may alter the shape of the catheter, as will be described in more detail below.

Figure 25C:
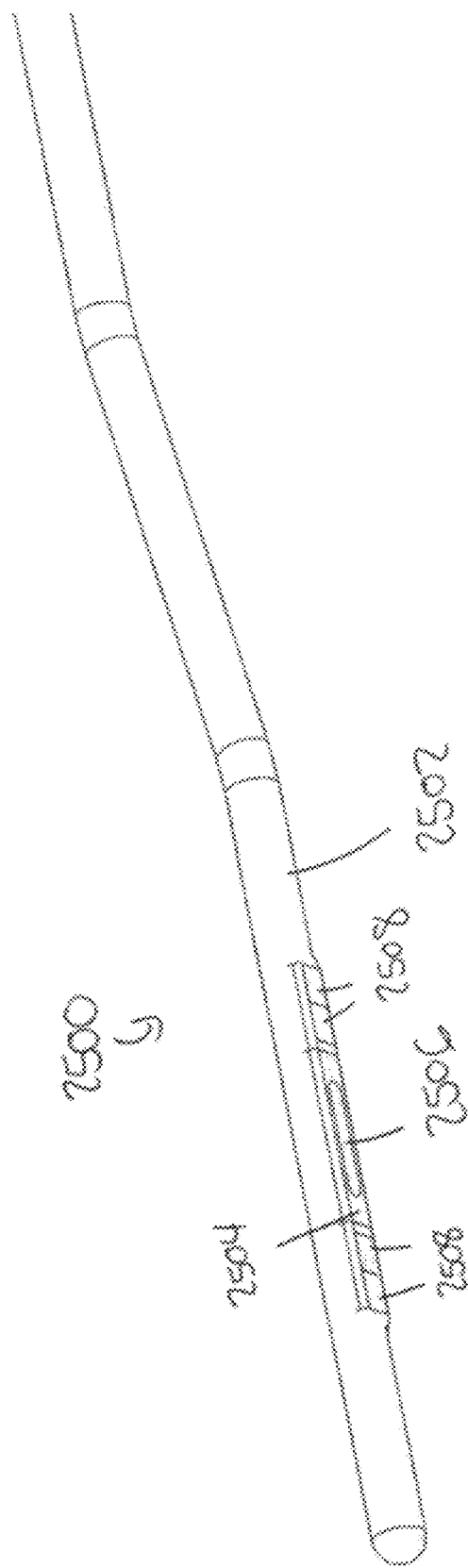

FIGS. 25A-25D illustrate one variation of catheter (2500). Specifically, FIG. 25A shows a partial cross-sectional area of catheter (2500). Shown there is catheter body (2502), nesting material (2504) housing coupling magnets (2508) and an electrode body (not shown) comprising ablation surface (2506), shaped lead wire (2510), straightening cannula (2512), and torque-transmitting sheath (2514). A portion of catheter body (2502) is not shown in FIG. 25A to help illustrate the other elements of catheter (2500). While shown in FIG. 25A as having an electrode housed within nesting material (2504) to define ablation surface (2506), catheter (2500) may comprise any suitable fistula-forming element, such as those described in more detail above. Furthermore, while shown in FIG. 25A as comprising a plurality of coupling magnets (2508), catheter (2500) need not. In variations where the catheter does comprise one or more magnets, the catheter may comprise any magnets or combination of magnets, such as those described above. Finally, catheter (2500) may or may not comprise a torque-transmitting sheath (2514), which may help rotate the catheter, as will be described in more detail below.

Figure 25D:
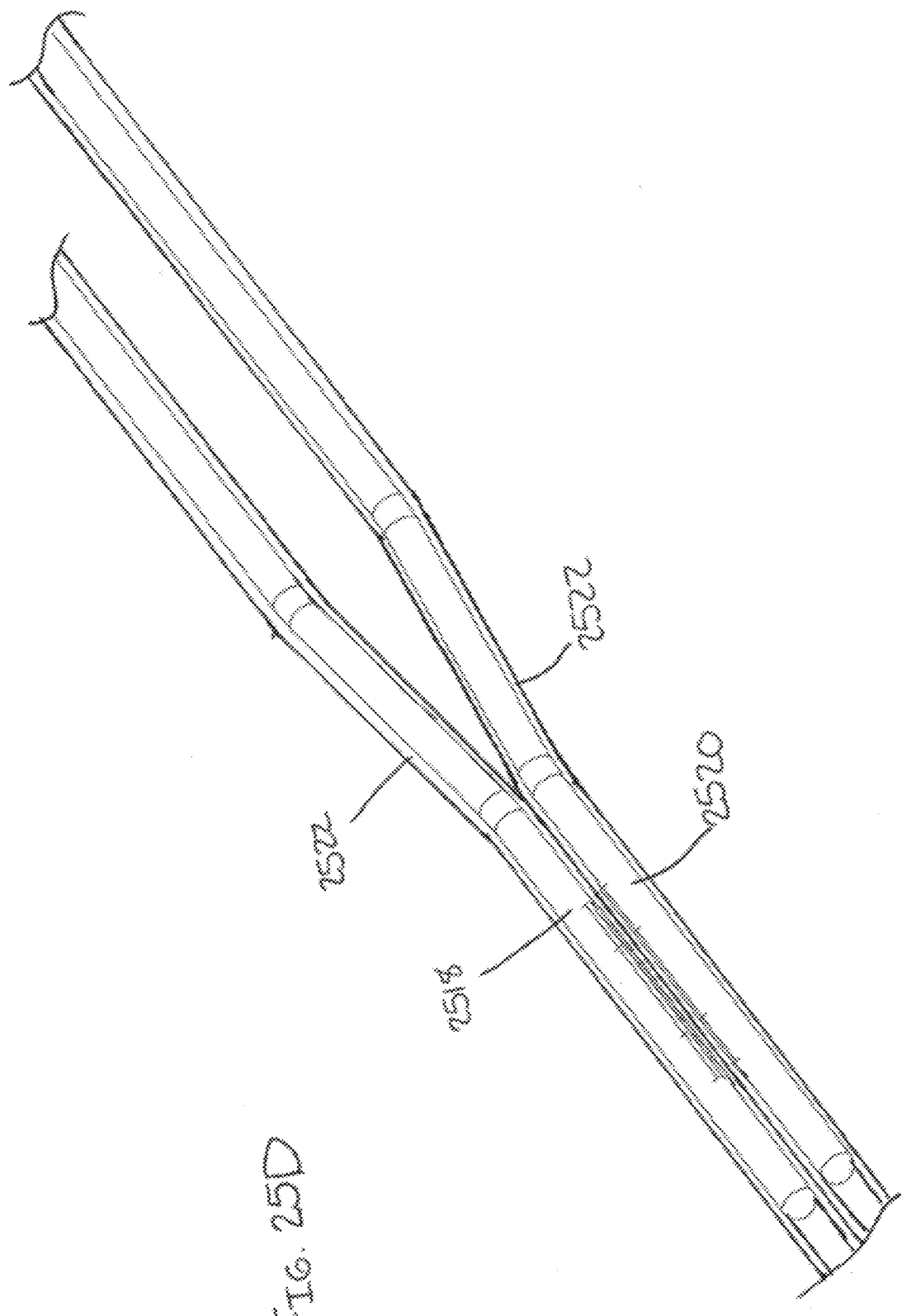

Shaped lead wire (2510) may be used to alter the shape of catheter (2500). Specifically, shaped lead wire (2510) may be pre-formed with one or more bends or curves. A straightening cannula (2512) may be advanced over lead wire (2510) to temporarily straighten or otherwise constrain the bends and curves of the shaped lead wire (2510), thereby rendering the distal portion of the catheter (2500) substantially straight, as shown in FIG. 25B. Catheter (2500) may be advanced into a blood vessel (not shown), at which point the straightening cannula (2512) may be withdrawn. Once withdrawn, shaped lead wire (2510) may return to its original configuration, which may cause catheter (2500) to change shape, as shown in FIG. 25C. When catheter (2500) is placed in a blood vessel, this shape change may alter the shape of one or more blood vessels. For example, FIG. 25D shows one variation in which two catheters (2518) and (2520) are placed in adjoining blood vessels (2522). As shown there, catheters (2518) and (2520) may comprise the components of catheter (2500) described immediately above. When the straightening cannulas (not shown) for each of catheters (2518) and (2520) have been withdrawn, the lead wires of each catheter may take on a bent/curved configuration, which may cause the distal portions of each of catheters to bend or flex toward each other, thereby bringing a portion of the blood vessels (2522) closer together as shown in FIG. 25D. One or more fistula-forming elements may then be activated to form a fistula between the adjoining blood vessels (2522).

Shaped lead wire (2510) may act as a lead wire to carry current to or from an electrode, but need not. Indeed, in some variations, a device may comprise a shaped wire and a separate lead wire. In variations where a catheter does not comprise an electrode, the catheter may comprise a shaped wire but no lead wire. It should also be appreciated that in some variations, a shaped member may be located outside of catheter. In some of these variations, the shaped member may be at least partially covered by one or more sheaths or other coverings, such as those described above. It should also be appreciated that any suitable shaped structure may be used to alter the shape of the catheters described here.

In variations where a catheter comprises one or more expandable structures (e.g., a balloon or the like), as will be described in more detail below, the expandable structure may be used in conjunction with a shape-changing member to help position a catheter within a vessel. For example, in the variation of catheter (2500) described above with respect to FIGS. 25A-25D, catheter (2500) may further comprise one or more expandable structures (not shown), such as one or more inflatable balloons. These expandable structures may be expanded inside of a blood vessel to temporarily hold catheter (2500) in place relative to the vessel. When shaped lead wire (2510) and straightening cannula (2512) are used to move catheter body (2502) between a bent and a straight configuration, contact between the expandable structure and the surrounding tissue may help to move the blood vessel with the catheter body (2502). In some variations, catheter (2500) may comprise a single expandable structure, which may be located proximal or distal to the bend of the shaped lead wire (2510). In other variations, catheter (2500) may comprise one or more expandable structures on either side of the bend of the shaped lead wire (2510). In variations where a shaped lead wire comprises multiple bends, expandable structures may be positioned proximal and/or distal all, some, or none of the bends. It should also be appreciated that the expandable structures may be used in conjunction with any suitable shape-changing element (e.g., a shaped wire, a pull wire, or the like), and may be used to provide temporary attachment and/or fixation between the catheter body and vessel tissue in any suitable manner.

Markers

The catheters described here may comprise one or more markers that may allow for visualization of one or more portions of a catheter during positioning and/or orientation thereof. In some variations, the marker may be directly visualized. In other variations, the marker may be indirectly visualized (e.g., via ultrasound, fluoroscopy and/or X-ray visualization). Markers may be located anywhere relative to the catheter, e.g., one or more surfaces of the catheter, inside of the catheter. In some variations, one or more portions of the catheter may be made from an echogenic or radiographic material. A marker may be attached to the catheter by any suitable method, for example, by mechanical attachment (e.g., embedded in a portion of the catheter, circumferential circumscription, or the like), adhesive bonding, welding, soldering, combinations thereof or the like.

Figure 14C:
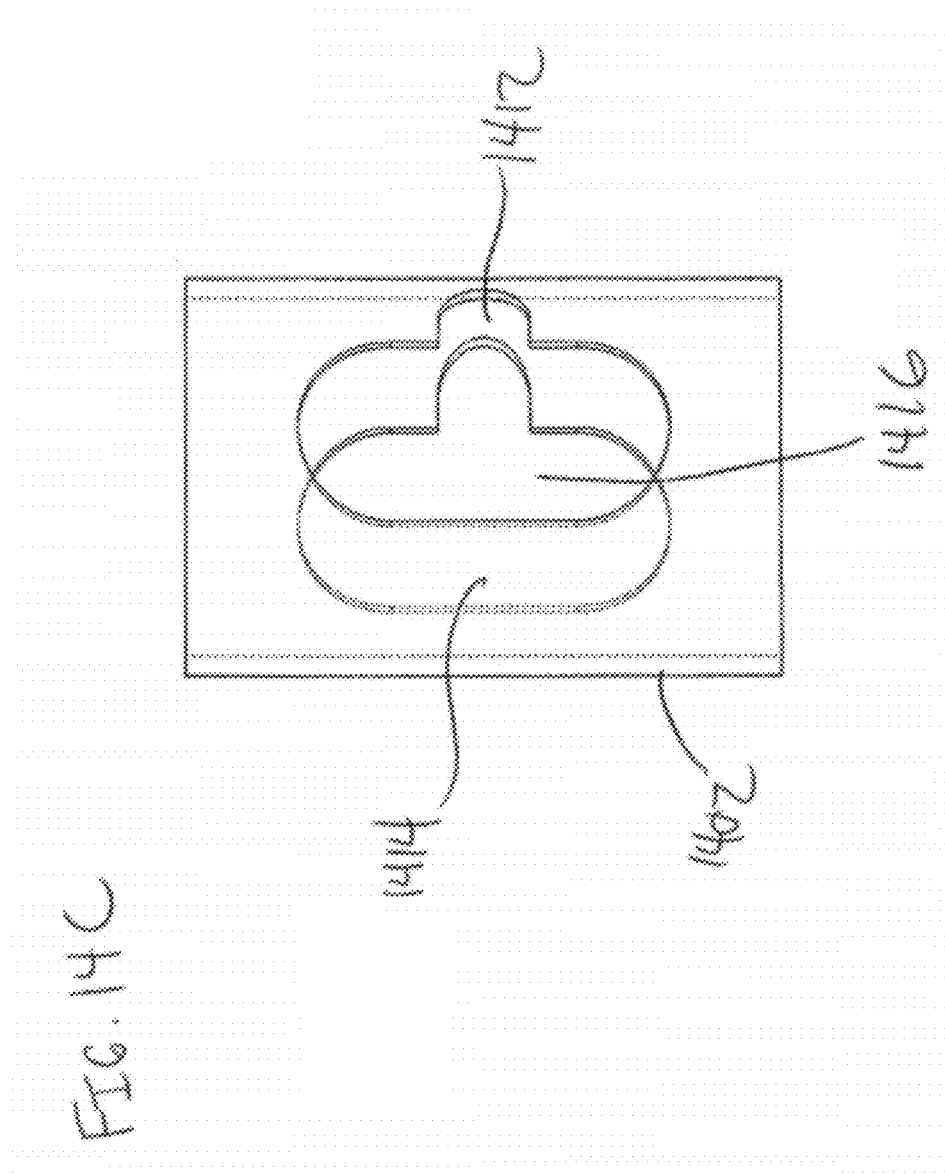
FIGS. 14C and 14D depict side views of a marker band.
Figure 14D:
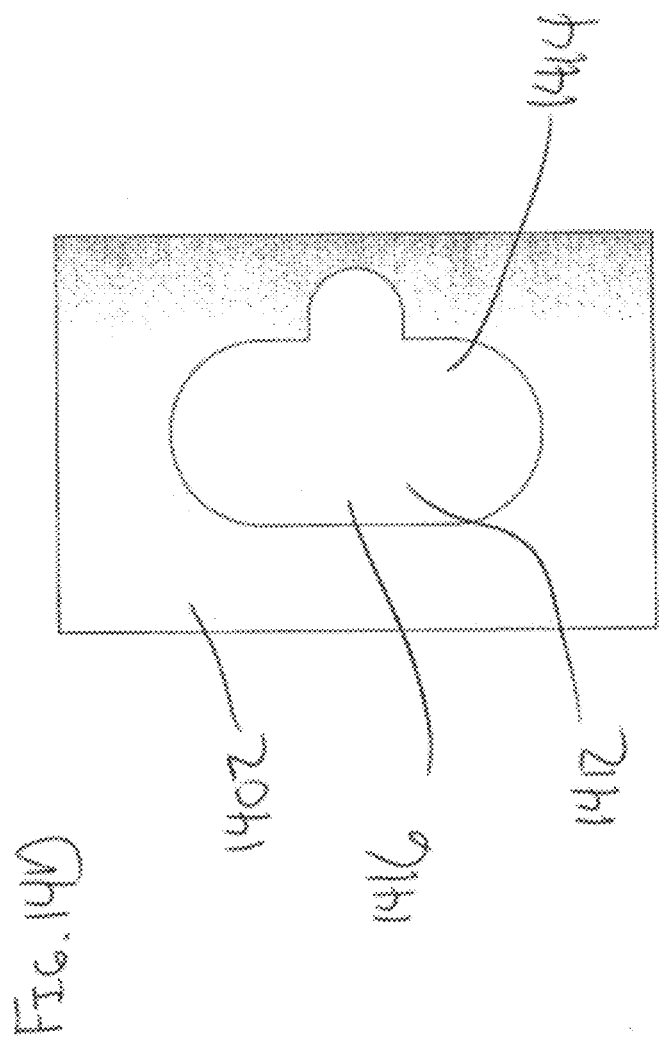

FIGS. 14A-14D illustrate one variation of catheter (1400) comprising marker bands (1402). Also shown in FIG. 14A are anchoring magnets (1410), and electrode (1404) partially covered by nesting material (1406) and comprising ablation surface (1408). Catheter (1400) may comprise any suitable number of marker bands (1402), and each marker band (1402) may be positioned at any suitable location in or on catheter (1400). Marker bands (1402) may comprise cut-out regions that may help a practitioner determine the position of a catheter via one or more imaging techniques. Specifically, FIG. 14B shows a perspective view of one marker band (1402) comprising a first cut-out region (1412) and a second cut-out region (1414). First (1412) and second (1414) cut-out regions are shown in FIGS. 14B-14D as having the same shape, but need not. When marker band (1402) is visualized (e.g., via ultrasound or fluoroscopy), a user may be able to see the negative space formed by the overlapping segment (1416) of first (1412) and second (1414) cut-out regions. The shape of this overlapping segment (1416) may change as catheter (1400) (and with it, marker band (1402)) is rotated. Eventually, rotation of marker band (1402) may reach a point where first (1412) and second (1414) cut-out regions completely or substantially overlap, as shown in FIG. 14D. When marker band (1402) reaches this "aligned" configuration (or when two markers on associated catheters are each in an "aligned" configuration), a user may know that the catheter is in a rotational orientation suitable for activating a fistula-forming element. For example, in the variation of catheter shown in FIG. 14A, the ablation surface (1408) may be positioned relative to marker bands (1402) such that the ablation surface (1408) faces a direction perpendicular to the cut-out regions. When used in conjunction with a second catheter (not shown) having a second set of marker bands (not shown), the marker bands of each catheters may be used to rotationally and/or axially position the catheters such that that one or more fistula forming elements are properly positioned to form a fistula.

While shown in FIGS. 14A-14D as having bi-lobular shapes, the cut-out regions may be any shapes or combination of shapes, e.g., rectangular, circular, elliptical, multi-lobular shapes, alphanumeric symbols, any shape with one or more axes of symmetry (e.g., bilateral symmetry), and the like. In some variations, the cut-out regions may have a directional shape, which may have a tapered portion that indicates the location of the ablation surface of an electrode, e.g., a polygon with a vertex at an acute angle, arrow, and the like. First and second cut-out regions may have the same shape as each other, or may each have different shapes. Other orientation markers or indicators may be provided on the catheter and/or electrode as desired and described below. While shown in FIGS. 14A-14D as comprising marker bands, it should be appreciated that the catheters described here may comprise any marker that is capable of indirect visualization.

In other variations, the catheter may comprise one or more visual markers that may help align two or more catheters relative to each other. For example, FIGS. 15A and 15B illustrate one variation of catheter (1500) comprising a lateral stripe (1504) which may help orient catheter (1500). Specifically lateral stripe (1504) may be a visual marker with a known location relative to a fistula-forming element (1508). For example, in the variation shown in FIGS. 15A and 15B, lateral stripe (1504) is longitudinally aligned with fistula-forming element (1508). When the distal end of catheter (1500) is placed in the body (and thus cannot be directly visualized), the lateral stripe (1504) (which may at least partially remain outside of the body) may give a visual indication as to the rotational orientation of the fistula-forming element (1508). When two catheters (1500) are placed in two blood vessels (not shown), as illustrated in FIG. 15B, the relative positioning of laterals stripes (1504) may give an indication of the relative positioning of the two catheters. For example, as shown in FIG. 15B, when the lateral stripes (1504) of each catheter (1500) are directly across from each other, the fistula-forming elements (1508) of each catheter (1500) may be in an appropriate orientation for activation of the fistula-forming elements. Lateral stripe (1504) may be applied to catheter (1500) in any suitable manner (e.g., via ink marking, texturing, application of one or more colored adhesives, etc.).

External Positioning

In some variations of the catheters described here, a catheter may comprise one or more balloons or other expandable structures. These expandable structures may serve one or more functions. In some instances, an expandable structure may help appose an electrode surface (or other fistula-forming element) against one or more vessel walls. This apposition may help temporarily flatten or otherwise relocate tissue, and may act to displace blood from the area. Additionally, during fistula formation, the expandable member may continue to urge the fistula forming element against tissue as it is removed from the vessel wall. In some variations, the expandable structure may be configured to help provide apposition between the catheter and a vessel wall, while still allowing for blood flow through the blood vessel. In some instances, one or more expandable structures may help modify or otherwise alter the size or shape of a fistula. In still other instances, the expandable structures may be used to dilate, contract, or otherwise displace a portion of one or more blood vessels. In some of these variations, this displacement may help bring a portion of the blood vessel closer to a skin surface. In still other variations, as mentioned above, one or more expandable structures may be used to hold a catheter in place relative to a blood vessel, and may aid in repositioning the blood vessel.

As mentioned above, in some variations of the catheters described here, the catheter may comprise one or more balloons. For example, FIGS. 9A-9D depict various illustrations of catheters comprising a balloon. In some variations, the balloon may be configured to push a portion of a catheter (e.g., an ablation surface or other fistula forming element) into contact with a blood vessel wall. For example, FIG. 9A depicts one variation of catheter (900) comprising balloon (902), and an electrode body (not shown) having an exposed ablation surface (904). Balloon (902) may have an undeployed collapsed configuration (not shown) for low-profile advancement and a deployed expanded configuration (as shown in FIG. 9A). In the variation shown in FIG. 9A, balloon (902) may be non-concentrically mounted on the catheter (900) away from ablation surface (904) such that expansion of balloon (902) within a blood vessel may bias, press, or otherwise push ablation surface (904) against a blood vessel wall. In variations where the catheter has a flat ablation surface, expansion of the balloon (902) may help flatten tissue against the ablation surface. Additionally, the balloon (902) may aid in fistula formation by continuing to urge the ablation surface (904) against and through the blood vessel wall as tissue is ablated, vaporized or otherwise removed. In still other instances, expansion of the balloon (902) may help displace blood from the vicinity of ablation surface (904), which in turn may minimize current loss to blood during ablation. In instances where a catheter comprises a recessed electrode, as described in more detail above, expansion of a balloon may displace some blood from the area while causing other blood to be trapped within the recessed portion. In instances where catheter (900) comprises one or more shape-changing elements, engagement between the balloon (902) and the surrounding blood vessel (not shown) may help to hold the catheter (900) in place and may further aid in repositioning the vessel tissue when the catheter (900) changes shape.

It should be appreciated that while shown in FIG. 9A as having a balloon (902), the catheters described here may achieve one or more of these functions using any suitable expandable structure or structures (e.g., one or more expandable cages, meshes, scaffolds, struts, or the like). The balloons described here may have any suitable shape or shapes (e.g., cylindrical, semi cylindrical, circular, trapezoidal, rectangular, fractional portions thereof, and the like), and may be made of any suitable material or combination of materials (e.g., one or more non-elastic, elastic, or semi-elastic materials).

Additionally, while the balloon (902) shown in FIG. 9A as being mounted on an opposite side of catheter (900) from the ablation surface (904), it should be appreciated that the balloon (902) may be positioned in any manner relative to the catheter (900). For example, in some variations a balloon (or other expandable structure) may be positioned such that expansion thereof creates a directional distension of a blood vessel. For example, FIG. 9B depicts one such variation of a catheter (910) comprising a balloon (912) and ablation surface (914) of an electrode (not shown). As shown there, balloon (912) may be positioned on catheter (910) such that the balloon (912) expands in a direction approximately orthogonal relative to the direction in which the ablation surface (914) faces. When catheter (910) is placed in a blood vessel and ablation surface (914) is aligned with another catheter an adjoining blood vessel, expansion of balloon (912) may cause directional distension of a blood vessel toward the skin overlying the blood vessel, which in turn may cause that skin to distend. This distension may give a user a visual indication of placement of the balloon (912), thereby allowing a user or operator to locate the balloon and blood vessel from outside the body. This visualized location may provide a site through which a user may externally access the blood vessel (e.g., by puncturing with a needle or the like).

In some instances, a balloon or other expandable structure may help alter and/or regulate the flow of blood through a blood vessel. For example, in some variations, expansion of a balloon may dilate one or more portions of a blood vessel, which may encourage increased blood flow through that portion of the blood vessel. In other variations, an expandable element may temporarily occlude a blood vessel, or may reduce blood flow therethrough. In some of these variations, the expandable element may comprise one or more electrodes, which may be used to help reduce blood flow through a portion of a blood vessel. FIG. 9C shows one such variation of catheter (930) comprising an ablation surface (932) and balloon (934). As shown there, balloon (934) is positioned concentrically around catheter (930), and may comprise a plurality of electrodes (936) disposed on the balloon (934). Although shown in FIG. 9C as being located distally on catheter (900) relative to ablation surface (932), it should be appreciated that balloon (934) may be placed proximally relative to ablation surface (932) and/or may be non-concentrically mounted away from ablation surface (932). Indeed, in some variations (as described in more detail below), catheter may comprise balloon both proximal to and distal to the ablation surface, each of which may comprise one or more electrodes. While shown in FIG. 9C as having a plurality of circumferentially disposed electrodes (936), balloon (934) may comprise any suitable number of electrodes (e.g., zero, one, two, three, or four or more) and each electrode may fully or partially circumscribe balloon (934).

Balloon (934) may be expanded within a blood vessel to temporarily occlude the vessel. Additionally, one or more of the electrodes (936) may be activated to partially constrict the blood vessel and reduce flow through at least a portion of the vessel. Specifically, electrical energy may be delivered to the vessel wall to induce necrosis and/or a proliferative cellular response, which may reduce the inner diameter of the blood vessel, thereby reducing the blood flow therethrough.

The balloons described immediately above may be used to alter or otherwise regulate blood flow relative to a fistula. FIG. 9D illustrates one example of how catheter (930) may be used to affect blood flow relative to a fistula. As shown there, catheter (930) may be advanced in an arterial vessel (940) that is in close proximity to a corresponding venous vessel (942). A second catheter (not shown) may be placed in venous vessel (942), and one or more alignment elements (not shown) may be used help approximate the arterial (940) and venous (942) vessels. Ablation surface (932) may be activated (alone, or in conjunction with one or more electrodes of the other catheter) to form an arterio-venous fistula, through which blood may flow (as represented by arrow (932)). Arrow (941) indicates the direction of blood flow in arterial vessel (940) and arrow (943) indicates the direction of blood flow in venous vessel (942). As shown in FIG. 9D, catheter (930) may be advanced in a retrograde (i.e., against the blood stream) direction into an arterial vessel (940), such that balloon (934) is located upstream of the ablation surface (932) and the resulting fistula. In these instances, balloon (934) may be expanded in arterial vessel (940) to at least partially occlude the vessel and temporarily prevent or reduce arterial blood flow therethrough, which in turn may help prevent current loss during fistula formation. Additionally, electrodes (936) may be activated to damage or scar surrounding tissue, which may reduce flow therethrough. This may be used to help prevent one or more potential complications with fistula formation, such as steal syndrome. For example, steal syndrome may occur when a fistula is formed between an artery and a vein, and blood flows through the resulting fistula at a rate the results in insufficient blood flowing distally/downstream of the fistula in the artery. This can result in tissue necrosis, and may necessitate an additional surgical procedure to prevent the loss of a limb. Accordingly, electrodes (936) may be activated to reduce flow through a vein, which may reduce flow through the fistula, and may thereby reduce the likelihood of steal syndrome.

While shown in FIG. 9D as being advanced in a retrograde fashion and located upstream of the ablation surface (932), balloon (934) may alternatively be located downstream of ablation surface (932) and the resulting fistula. In some of these variations, catheter (930) may be advanced in an anterograde (i.e., with the flow of blood) fashion into arterial vessel (940). In other variation, a catheter may be advanced in a retrograde fashion, but a balloon may instead be located proximally on catheter relative to the ablation surface. In still other variations, a catheter may be moved within the blood vessel to change the positioning of a balloon between an upstream position and a downstream position, and vice versa. When a balloon is placed downstream in an arterial vessel (940), the balloon may be expanded to dilate the vessel (940) to increase blood flow therethrough or may be constricted using one or more electrodes to decrease blood flow therethrough. Dilating the downstream portion of the arterial vessel (940) may divert blood flow away from the fistula, while constriction of the downstream portion may encourage increased blood flow through the fistula. It should be appreciated that one or more balloons and/or electrodes may be placed in a venous vessel upstream or downstream relative to a fistula to dilate and/or constrict portions of the venous vessel. Arterial and/or venous dilation or constriction may help aid fistula maturation and/or prevent venous hypertension, as will be described in more detail below.

While shown in FIGS. 9A-9D as having a single balloon, it should be appreciated that the catheters described here may have any suitable number of balloons, expandable members, or combinations thereof. Indeed, the catheters described may comprise a plurality of expandable members for positioning the catheter within a blood vessel, urging an electrode ablation surface against a blood vessel wall, and/or regulating the blood flow in the vicinity of the targeted vascular site. FIG. 10A depicts one such variation of a catheter (1000) comprising an ablation surface (1006), a first balloon (1002) located proximal to the ablation surface and comprising circumferential electrodes (1008), and a second balloon (1004) located distal to the ablation surface. While only the first balloon (1002) is shown in FIG. 10A as having electrodes (1008), it should be appreciated that any of balloons (e.g., none of the balloons, only the first balloon (1002), only the second balloon (1004), or both the first (1002) and second (1004) balloons) may comprise any suitable number of electrodes (e.g., one, two, three, or four or more electrodes). The first (1002) and second balloons (1004) may be independently actuated to regulate blood flow within a blood vessel. For example, catheter (1000) may be inserted into a vein (not shown), in which the direction of blood flow is represented by arrow (1001). Second balloon (1004) may be expanded to dilate the downstream portion of the vein, while the circumferential electrodes (1008) of first balloon (1002) may be activated to constrict the vein. In other instances the catheter (1000) may be inserted in the opposite direction (or the balloons may be otherwise positioned) such that the second balloon (1004) may be used to dilate the upstream portion, and first balloon (1002) may constrict the downstream portion. In still other instances, the balloon may be configured to dilate both the upstream and downstream portions, or may be configured to constrict both the upstream and downstream portions. Again, it should be appreciated that any expandable structure or structures may be utilized by the catheters.

Figure 10C:
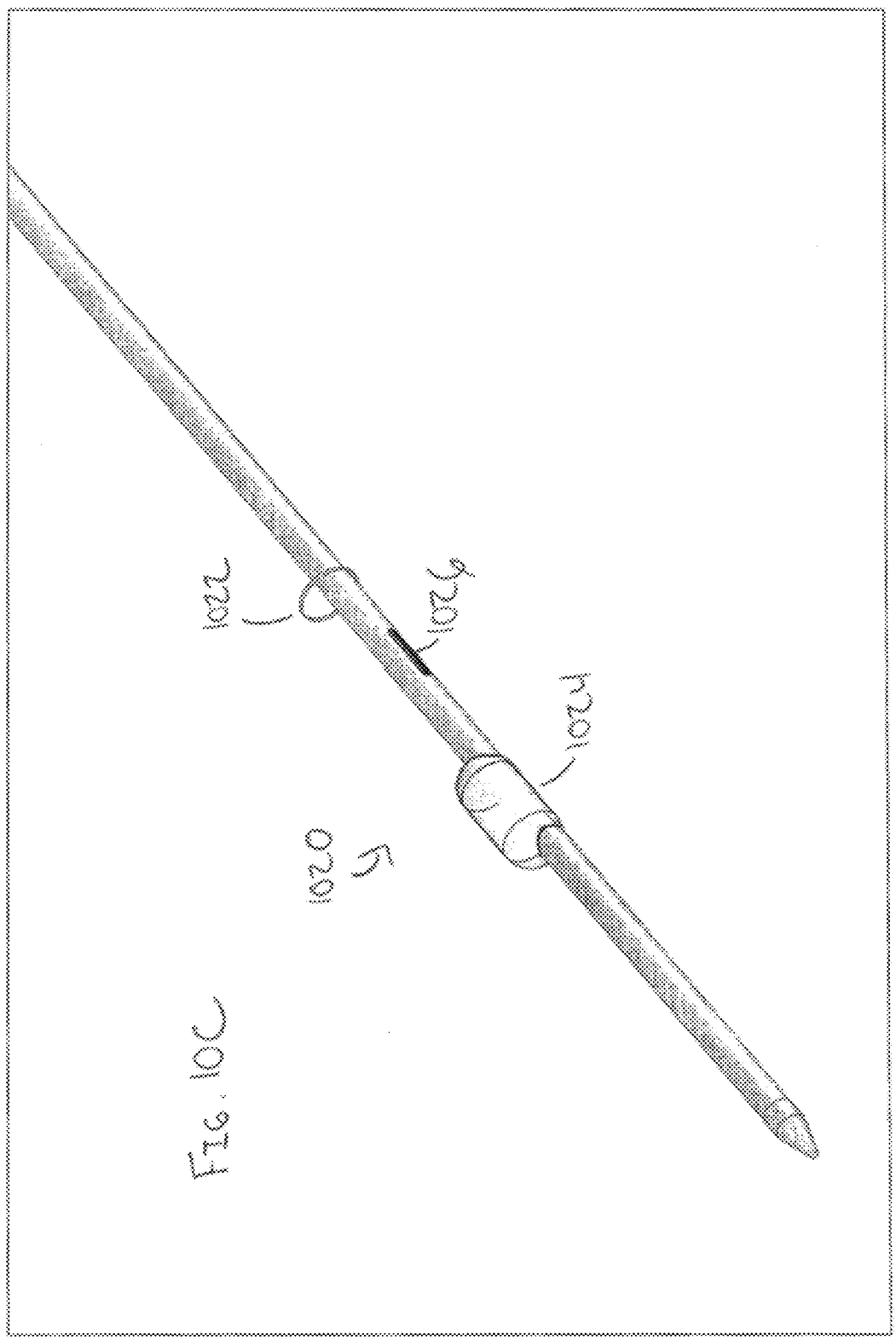

FIG. 10B shows another variation of catheter (1010) comprising an electrode with ablation surface (1016), a proximal balloon (1012) and a distal balloon (1014). Proximal balloon (1012) may comprise a fixed volume body and may further comprise a circumferential band electrode (1018) around a portion of the balloon (1012). Circumferential band electrode (1118) may expand or collapse with an expandable member. FIG. 10C illustrates still another variation of a catheter (1020) with a distal balloon (1024), a proximal expandable wire loop (1022), and an ablation surface (1026). Wire loop (1022) may be movable between an undeployed, low-profile configuration (not shown), and a deployed, expanded configuration (as shown FIG. 10C). Wire loop (1022) may be moved between the undeployed and deployed configuration using any suitable mechanism (e.g., hinged radial struts, a coiling mechanism, etc.), and RF energy may be applied to the wire loop (1022) to induce tissue necrosis, as described above.

In some variations, once a fistula has been formed, one or more balloons or other expandable structures may be used to modify the size or shape of a fistula. For example, FIG. 11 illustrates one such variation of catheter (1100). As shown there, catheter (1100) may comprise an electrode ablation surface (1102) and a lateral extension balloon (1104). Lateral extension balloon (1104) may be configured to expand in two or more directions, and may be used to alter the size or shape of a fistula. Specifically, ablation surface (1102) (or another suitable fistula-forming element) may be used to form a fistula (not shown) between two vessels (not shown), and catheter (1100) may be subsequently moved to position the lateral extension balloon (1104) adjacent or near the fistula. Balloon (1104) may be then be expanded, and a portion of balloon (1104) may push into the fistula, thereby altering its size and/or shape. Balloon (1104) may be a fixed volume structure, or may be made from one or more elastic or semi-elastic materials. It should also be appreciated that the lateral extension balloon (1104) may comprise two or more separate balloons. Additionally, lateral extension balloon (1104) may comprise pleats (1106) or other surface modification to regulate the degree of expansion, which may also provide traction or a frictional attachment to the blood vessel wall at the target vascular site. For example, in the variation shown in FIG. 11, pleats (1106) may engage tissue surrounding the fistula to help move or adjust that tissue.

In other variations of the catheters described here, a catheter may comprise one or more balloons that may be configured to allow blood flow therethrough. For example, FIG. 12 shows another variation of catheter (1200) comprising a plurality of ring-shaped balloons (1202). Also shown there is electrode ablation surface (1204). In these variations, expansion of the balloons (1202) may allow for the increased apposition and blood displacement between ablation surface (1204) and a vessel wall (not shown), as described in more detail above. Additionally, the lumens (1208) within each of the ring-shaped balloons (1202) may allow for blood to pass therethrough. In this way, catheter (1200) may be left inside of a blood vessel (not shown) for an extended period of time without substantially affecting blood flow therethrough. For example, in some instances it may be necessary to leave catheter (1200) in a blood vessel for an extended period of time, during which it may not be feasible to block all blood flow through the blood vessel. It should be appreciated that one or more of the balloons (1202) may also be configured to dilate one or more portions of a blood vessel, and/or may comprise one or more electrodes to help constrict a blood vessel, as described in more detail above.

In some variations, one or more balloons of a catheter may carry or be inflated with a contrast material to help in visualization of the catheter. In some variations, one or more of these balloons may be pierced or otherwise punctured to release the contrast agent into the blood vessel, which may be used to evaluate whether a fistula has been properly formed. For example, FIGS. 26A and 26B illustrates one such variation of catheter (2600). As shown there, catheter (2600) may comprise a catheter body (2602) with distal balloon (2604), central balloon (2606), and proximal balloon (2608). Catheter (2600) may additionally comprise one or more shape-changing elements or alignment elements, such as those described above. Additionally, while shown FIGS. 26A and 26B as having three balloons, the catheter (2600) may comprise any suitable number of balloons (e.g., one, two, three, or four or more). Each of balloons (2604), (2606) and (2608) are shown in FIGS. 26A and 26B as being concentrically mounted around catheter body (2602), but they may be mounted in any suitable manner or manners, such as described in more detail above.

When catheter (2600) is placed in a blood vessel (not shown), distal (2604), central (2606), and proximal (2608) balloons may be inflated. These balloons may be inflated using any suitable fluid or fluids (e.g., saline, water, one or more contrast solutions, or the like). In some variations, all three balloons are inflated with the same fluid. In other variations, the distal (2604) and proximal (2608) balloons are inflated with a first fluid (e.g., a first contrast solution), while the central balloon (2606) is inflated with a second fluid (e.g., a second contrast solution having a higher or lower contrast level). In yet other variations, each balloon is inflated with a different solution. When the balloons are inflated, proximal (2608) and/or distal balloon (2604) may engage an interior surface of the blood vessel to prevent fluid flow thereby. For example, in instances where proximal balloon (2608) is placed in a blood vessel upstream relative to the flow of blood, inflation of proximal balloon (2608) may temporarily stop blood flow through the blood vessel.

In some instances, a second catheter (2610) may be placed in an adjoining blood vessel (not shown), as illustrated in FIG. 26B. Second catheter (2610) may comprise a catheter body (2611), and a nesting material (2614) housing a lead-wire electrode (2612), such as described in more detail above). While shown in FIG. 26B as comprising a lead-wire electrode (2612), it should be appreciated that second catheter (2610) may comprise any suitable fistula-forming element such as those described in more detail above. In some of these instances, the catheter (2600) and the second catheter (2610) may be aligned (e.g., using one or more alignment elements such as those described above) such that the nesting material (2614) may be in axial and rotational alignment with the central balloon (2606), and current may be applied to lead-wire electrode (2612) to ablate vessel tissue between the catheters, thereby forming a fistula (not shown). During or after fistula formation, one or more portions of the lead-wire electrode (2612) may puncture, pierce, or otherwise penetrate the central balloon (2606) to release one or more fluids therefrom. When this fluid comprises one or more contrast solutions, this fluid may be viewed (e.g., fluoroscopically) as it passes through the fistula. In this way, as the contrast fluid passes between the blood vessels, a user may be able to determine that the fistula has been formed in a manner that allows fluid flow therethrough. While central balloon (2606) is discussed above as being punctured, it should be appreciated that any balloon or balloons of the catheter (2600) may be pierced or punctured by a fistula-forming element.

Catheter Body

The catheters described hereinthroughout may be any elongate body suitable for advancement through at least a portion of the vasculature. The catheters may be hollow, partially hollow, and/or partially solid. One or more portions of the catheter may be flexible or semi-flexible, one or more portions may be rigid or semi-rigid, and/or one or more portions of the catheter may be changed between flexible and rigid configurations. Flexible portions of the catheter may allow the catheter to be navigated through tortuous blood vessels to reach a desired target site. The catheters described here may be made of any material or combination of materials. For example, the catheters may comprise one or more metals or metal alloys (e.g., e.g., nickel titanium alloys, copper-zinc-aluminum-nickel alloys, copper-aluminum-nickel alloys, and the like) and/or one or more polymers (e.g., silicone, polyvinyl chloride, latex, polyurethane, polyethylene, PTFE, nylon, and the like). Catheters may have any suitable dimensions. For example, catheters may have any suitable length that allows the catheter to be advanced from a point external to the body to a target location. Catheters may have any diameter suitable for intravascular use, such as, for example, about 5.7 French, about 6.1 French, about 7 French, about 8.3 French, between about 5 French and about 9 French, between about 5 French and about 7 French, between about 6 French and about 9 French, or the like.

Some variations of the catheters described here may have a lumen, slit, or passageway extending at least partially through the length of the catheter. Lumens may be used to pass one or more devices (e.g., a guidewire) and/or one or more substances (e.g., contrast solution, perfusion fluid, one or more drug-containing solutions, etc.) through a portion of the device. For example, the variation of catheter (300) shown in FIG. 3 and described in more detail above comprises a lumen (308) passing therethrough. Although shown in FIG. 3 as passing concentrically through magnets, it should be appreciated that a lumen may have any positioning relative to other components of the device. For example, in the variation of catheter (600) shown in FIG. 6A, lumen (608) may extend next to one or more magnets of the proximal (604) and distal (606) anchoring magnets. In still other variations, a lumen may be attached to or otherwise run along an exterior surface of the catheter.

When housed at least partially inside of the catheter body, a lumen may pass between any portion or portions of the catheter. For example, in the variations described immediately above, the lumens may exit out the distal-most tip of the catheter. In other variations, one end of a lumen may be located at an intermediate portion of the catheter. In some variations, a lumen may be divided into a number of sublumens. For example, FIGS. 16A and 16B show a perspective view and a partially-transparent view, respectively, of one variation of catheter (1600). Shown there is catheter (1600) with main lumen (1610) which subdivides into first (1602), second (1604), third (1606), and fourth (1608) lumens at a distal tip (1601) of the catheter. Main lumen (1610) may be divided into any suitable number of lumens (e.g., two, three, four, or five or more), and each of these lumens may have ends at any suitable points on the catheter. In variations where a main lumen is split into two or more lumens, the two or more lumens may provide one or more fluids or other substances to two or more points simultaneously.

The catheters described herein throughout may have any suitable tip portion. In some variations, the tip may be rounded or otherwise blunted so as to help minimize tissue trauma during advancement of the catheter. Additionally or alternatively, the distal tip may be at least partially tapered. A tapered tip may assist the catheter in navigating through the vasculature and/or may help dilate the blood vessels during advancement. The tip of the catheter may be integral with the rest of the catheter body, or may be a separate component joined to the catheter body. In some of these variations, the tip of the catheter may be releasably attached (e.g., via screw-fit, snap-fit, friction-fit or the like) to the catheter, which may allow a user to select a tip portion that is appropriate for a given patient or blood vessel.

The tip portion of the catheter may help guide a catheter through the vasculature. In some variations, a lumen may run through the catheter to a tip of the catheter. In these variations, a guidewire may be threaded through the lumen, and the catheter may be advanced over the guidewire to a target location. In other variations, a guidewire may be fixedly attached to the tip of the catheter. For example, in the variation of catheter (1600) shown in FIGS. 16A and 16B and described in more detail above, tip (1601) may comprise a guidewire (1612) that is attached to and extends from tip (1601). Guidewire (1612) may be advanced into the vasculature to help guide the catheter to a target location. In still other variations, a tip may comprise a rapid exchange portion. For example, in the variation of catheter (100) shown in FIGS. 1A-1C above, the tip of catheter (100) comprises rapid exchange portion (100) having first and second apertures ((112) and (114) respectively) that are in communication with one another. A guidewire (not shown) may be threaded through the first (112) and second (114) apertures, such that the rapid exchange portion (100) (and with it, catheter (100)) may be advanced along the guidewire to a target location. While shown in FIGS. 1A-1C as being located at the tip of catheter (100), it should be appreciated that the rapid exchange portion (100) may be located at any suitable point along the length of the catheter (100).

Some variations of the catheters described here may comprise a torsion-transmitting sheath. As the length of a catheter is increased, one or more rotational forces applied to a proximal end may have a reduced ability to rotate the distal end of the catheter. To help prevent torsion-transmission problems, the catheter may comprise a torque-transmitting sheath disposed on or in the catheter. A torsion-transmitting sheath may be made from any stiff or stiffened materials that may resist rotational forces (e.g., stainless steel, shape memory allows, and various plastics), which may allow the practitioner to adjust the location and the rotational orientation of the distal portion of the catheter when it is inserted into a blood vessel.

In some variations, the catheter may comprise one or more suctions ports. In these variations, the suction ports may be used to remove blood or other fluids from a portion of a blood vessel. For example, FIGS. 27A-27D illustrate one variation of a catheter (2700) comprising suction ports (2702). FIG. 27A shows a perspective view of catheter (2700), comprising suction ports (2702), sleeve (2704), nesting material (2706) housing a spring electrode (2708) and coupling magnets (2710), proximal balloon (2712), and distal balloon (2714). While shown in FIG. 27A as having spring wire electrode (2708) and coupling magnets (2710), catheter (2700) may comprise any suitable combination of fistula-forming elements and/or alignment elements, such as those described in more detail above. Sleeve (2704) may be advanced to cover one or more components of the catheter (2700), as illustrated in FIG. 27B, which may help facilitate low-profile advancement of catheter (2700) through tissue.

When catheter (2700) is placed in a blood vessel, suction ports (2702) may be used in conjunction with proximal (2712) and distal (2714) balloons to temporarily remove blood and/or any other fluids from a portion of a blood vessel prior to or during fistula formation. For example, FIGS. 27C and 27D illustrate one method by which catheter (2700) may be used to form a fistula (not shown). As shown in FIG. 27C, catheter (2700) may be advanced into vein (2716), while a second catheter (2718) may be advanced into artery (2720). Second catheter (2718) may comprise a flat electrode ablation surface (not shown), may comprise another suitable fistula-forming element such as those described in more detail above, or may not comprise any fistula-forming element. During advancement of catheter (2700), sleeve (2704) may be in an advanced position in which sleeve (2704) covers one or more elements of the catheter (2700). For example, sleeve (2704) may cover spring wire electrode (2708) (not shown in FIGS. 27C and 27D) to hold spring wire electrode in a low-profile configuration.

Once the catheters have been advanced, sleeve (2704) may be withdrawn to reveal one or more components of the catheter. For example, when sleeve (2704) is withdrawn, spring wire electrode (2708) (not shown in FIGS. 27C and 27D) may extend from catheter toward second catheter (2718) (and in some instances, toward one or more fistula-forming elements of the second catheter (2718)). Additionally, one or more alignment elements may help position catheter (2700) relative to second catheter (2718). For example, coupling magnets (2710) may be attracted to and align with one or more coupling magnets (not shown) of the second catheter (2718) to orient the spring wire electrode (not shown in FIGS. 27C and 27D) relative to the second catheter (2718), as shown in FIG. 27C. Once the catheters are in place and properly aligned, the proximal (2712) and distal (2714) balloons may be inflated, as shown in FIG. 27C. In some instances, the balloons (2712) and (2714) may hold catheter (2700) in place relative to the blood vessel. Additionally, each balloon may temporarily seal that portion of the blood vessel relative to the rest of the blood vessel.

Once the proximal (2712) and distal (2714) balloons have been inflated, vacuum or other suction may be applied to the suction ports (2702) such that any fluid between the proximal (2712) and distal (2714) balloons are removed from the vein (2716). In instances where the proximal (2712) and distal (2714) balloons create a seal within vein (2716), the suction may also cause a portion of the vein (2716) to collapse around catheter (2700), as shown in FIG. 27D. At this point, current may be supplied to the spring wire electrode (2708) (and in some instances carried away by a ground electrode of the second catheter (2718) to ablate and/or vaporize tissue between the catheters. In other instances, current may be supplied to an active electrode (not shown) of the second catheter (2718) and carried away by the spring wire electrode (2708). Additionally, because any blood or other fluids have been removed from the vein (2716) via suction portions (2702), there may be a reduction in current loss to surrounding fluids during tissue ablation. While catheters (2700) and (2718) are shown in FIGS. 27C and 27D as being placed in a vein (2716) and artery (2720) respectively, it should be appreciated that these catheters may be placed in any suitable blood vessels. In some variations, catheter (2700) may be placed in an artery while second catheter (2718) may be placed in a vein. In still other variations, both catheters are placed in veins. It should also be appreciated that both catheters may comprise suction ports.

Proximal Adaptors

The catheters described here may comprise one or more proximal adaptors and/or handles at a proximal end thereof. These elements may help advance or align the catheters, activate one or more fistula-forming elements, and/or deliver one or more fluids or substances into or through the catheter. FIGS. 13A and 13B show two variations of adaptors suitable for use with the catheters described here. FIG. 13A shows one variation of catheter (1300) comprising an adaptor (1302). Catheter (1300) may comprise any suitable fistula-forming element(s) and/or alignment feature(s), such as those described above. As shown there, adaptor (1302) comprises a first port (1306), a second port (1308), and a third port (1312). Although shown in FIG. 13A as having three ports, adaptor may comprise any suitable number of ports (e.g., zero, one, two, three, or four or more), and each port may serve any useful function (e.g., the introduction of one or more elements or substances into or through the catheter). For example, in the variation shown in FIG. 13A, first port (1306) may be used to introduce a fluid or substance (e.g., contrast agents, flush agents, therapeutic agents, and/or intravenous fluids) into a lumen (not shown), and may be connected to a liquid or gaseous fluid source (e.g., a fluid pump, a syringe, etc.). Similarly, second port (1308) may allow for the introduction of an electrosurgical lead (1320) for driving an electrical current to an electrode (not shown). In variations where the catheter (1300) does not comprise an electrode, any suitable control element (e.g., a pushrod, pull-wire, or the like) may enter the catheter via a port to control fistula formation. Finally, third port (1312) may allow for one or more devices (e.g., a guidewire) to pass through the catheter via hemostasis valve (1316). While shown in FIG. 13A as having a hemostasis valve (1316), third port (1312) need not have such a valve. It should be appreciated that each of the ports of a proximal adaptor may converge into a single lumen, or may provide access to different lumens. Additional ports may be provided as desired for other functions, such as a visualization port, an actuator port, a suction port, and the like. Ports may have any suitable connection form factor, such as a threaded connector, luer connector, or the like.

FIG. 13B shows another variation of catheter (1318). As shown there, catheter (1318) comprises the same proximal adaptor as the variation of catheter (1300) shown in FIG. 13A, and thus the same reference labels are used for the variation shown in FIG. 13B. Additionally shown in FIG. 13B is sleeve (1322) which may be provided over a portion catheter, and may be used to regulate the contact between an electrode ablation surface (1304) and a vessel wall (not shown). The position of sleeve (1322) may be controlled at least in part by a hub (1324). A user may manipulate hub (1324) to move sleeve (1322) proximally or distally relative to catheter (1300). This in turn may cause sleeve (1322) to either cover or expose electrode ablation surface (1304).

Some variations of adaptors comprise one or more alignment features that may help the practitioner to orient one catheter with respect to another. For example, the variation of adaptor (1502) shown in FIGS. 15A and 15B and described in more detail above may comprise an alignment projection (1506), where the rotational orientation of the alignment projection (1506) maps to a corresponding rotational orientation of the electrode ablation surface of the fistula-forming assembly. For example, when two catheters (1500) are placed in two adjoining blood vessels (not shown), the alignment projections (1506) of each catheter (1500) may be aligned with each other to align the respective fistula-forming components (1508) on each catheter.

It should be appreciated that any of the catheters described here comprise any combination of fistula-forming elements, alignment elements, catheter bodies, proximal adaptors, and/or expandable structures as described above, and catheter or combination of catheters may be used to form a fistula in any suitable manner.

Systems

Also described here are systems for forming a fistula between blood vessels. Generally, the system may comprise a first catheter, which may comprise one or more fistula-forming elements. The first catheter may comprise any of the fistula-forming elements or combination of fistula-forming elements as described in more detail above. For example, in some variations, the first catheter may comprise one or more electrodes, which may be comprise any of the electrode structures described in more detail above. In some variations, the first catheter may comprise one or more mechanical cutting elements, such as one or more of the blades described in more detail above. Additionally or alternatively, the first catheter may comprise one or more optical fibers which may be used to deliver laser energy to tissue. In variations where the first catheter comprises an electrode-based fistula-forming element, the system may comprise one or more ground electrodes, which may in some variations may be positioned externally of a patient.

In some variations, the first catheter may comprise one or more alignment elements. In some variations, the first catheter may comprise one or more shape-changing elements which may be used to alter the shape of the first catheter. In some of these variations, the first catheter may comprise a shaped wire and/or one or more pull wires, as described in more detail above. Additionally or alternatively, the first catheter may comprise one or more markers, such as those described in more detail above. Additionally or alternatively, the first catheter may comprise one or more magnets. In these variations, the first catheter may comprise any combination of alignment magnets and/or coupling magnets. In some variations, the first catheter may comprise one or more magnet arrays proximal to a fistula-forming element. Additionally or alternatively, the first catheter may comprise one or more magnet arrays distal to a fistula forming element.

The first catheter may comprise any suitable catheter body, as described in more detail above. In some variations, the first catheter may comprise one or more lumens extending at least partially through the catheter body. In some variations, the first catheter may be configured to be advanced over or along a guidewire. In some variations, the first catheter may comprise a lumen through a guidewire may pass. In other variations, the first catheter may comprise a rapid exchange portion. Additionally, in some variations the first catheter may comprise one or more expandable elements, as described in more detail above. In some variations, the first catheter may comprise one or more balloons. In some of these variations, the first catheter may comprise one or more balloons proximal to the fistula-forming element, and/or may comprise one or more balloons distal to the fistula-forming element.

In some variations, the system may further comprise a second catheter. In some variations, the second catheter may comprise a fistula-forming element, but need not. In variations where the second catheter does comprise a fistula-forming element, the second catheter may comprise any of the fistula-forming elements or combination of fistula-forming elements as described in more detail above. For example, in some variations, the second catheter may comprise one or more electrodes, which may be comprise any of the electrode structures described in more detail above. In some variations, the second catheter may comprise one or more mechanical cutting elements, such as one or more of the blades described in more detail above. Additionally or alternatively, the second catheter may comprise one or more optical fibers which may be used to deliver laser energy to tissue. The fistula-forming element of the second catheter may be the same as or different from the fistula-forming element of the first catheter.

In some variations, the first catheter may comprise an electrode which is configured to extend through vessel tissue during fistula formation (e.g., one or more of the wire electrodes or other deployable electrodes described in more detail below), the second catheter may be configured to receive or otherwise contact one or more portions of the first catheter's electrode during ablation. In some variations, the second catheter may comprise one or more recesses or pockets for receiving a portion of the first catheter's electrode, as described in more detail above. In some variations, an electrode of the second catheter may be configured to receive an electrode of the first catheter during fistula formation. In some variations, the electrode or other receiving surface may comprise one or more insulating coatings, such as those described in more detail above.

In some variations, the second catheter may comprise one or more alignment elements. In some variations, the second catheter may comprise one or more shape-changing elements which may be used to alter the shape of the second catheter. In some of these variations, the second catheter may comprise a shaped wire and/or one or more pull wires, as described in more detail above. Additionally or alternatively, the second catheter may comprise one or more markers, such as those described in more detail above. Additionally or alternatively, the second catheter may comprise one or more magnets. In these variations, the second catheter may comprise any combination of alignment magnets and/or coupling magnets. In some variations, the second catheter may comprise one or more magnet arrays proximal to a fistula-forming element. Additionally or alternatively, the second catheter may comprise one or more magnet arrays distal to a fistula forming element. In variations where both the first and the second catheter comprise alignment elements, the catheters may comprise the same configuration of alignment elements, or may comprise different configurations of alignment elements.

The second catheter may comprise any suitable catheter body, as described in more detail above. In some variations, the second catheter may comprise one or more lumens extending at least partially through the catheter body. In some variations, the second catheter may be configured to be advanced over or along a guidewire. In some variations, the second catheter may comprise a lumen through a guidewire may pass. In other variations, the second catheter may comprise a rapid exchange portion. Additionally, in some variations the second catheter may comprise one or more expandable elements, as described in more detail above. In some variations, the second catheter may comprise one or more balloons. In variations where the second catheter comprises a fistula-forming element, the second catheter may comprise one or more balloons proximal to the fistula-forming element, and/or may comprise one or more balloons distal to the fistula-forming element.

Methods

The methods described here may be utilized to create a fistula between two closely-associated blood vessels (e.g., between a vein and an artery, between two veins, etc.). Generally, in these methods one or more fistula-forming elements may be activated to bore through, perforate, or otherwise create a passageway between the two blood vessels such that blood may flow directly between the two adjoining blood vessels. When such a fistula is formed, hemostasis may be created without the need for a separate device or structure (e.g., a suture, stent, shunt, or the like) connecting or joining the blood vessels.

Generally, the methods described here comprise accessing a first blood vessel with a first catheter, and advancing the first catheter to a target location within a blood vessel. In some of these methods, a second blood vessel is accessed with a second catheter, and advanced to a target location within the second vessel. In some of these methods, a first catheter is advanced into an artery, and the second catheter is advanced into a vein. In other methods, a first catheter is advanced into a first vein, and a second catheter is advanced into a second vein. In still other methods, a first catheter is advanced into a first artery and a second catheter is advanced into a second artery. The first and/or second catheters may be advanced in any suitable manner, such as using a Seldinger technique or other similar technique. Advancement may or may not occur under indirect visualization (e.g., via fluoroscopy, x-ray, or ultrasound). The first and second catheters may be advanced in the same manner, or may be advanced in different manners. In variations where one of the catheters is configured for advancement over a guidewire (e.g., catheter (100) described above in relation to FIGS. 1A-1C) the catheter may be advanced along a guidewire. In variations where one of the catheters has a guidewire fixedly attached to its tip (e.g., catheter (1600) described above in relation to FIGS. 16A and 16B), the guidewire may be advanced through the vasculature to a target location. In other variations, one or more external magnets may help advance or position a catheter at a target site. For example, FIGS. 17A and 17B show a perspective view and a side view, respectively, of an external magnet (1700) that may be used to help advance catheter (1702) within a blood vessel (1704). External magnet (1700) may interact with any suitable portion of the catheter (e.g., a fixed guidewire (1706), one or more magnetic alignment elements, etc.) to create an attractive force between the catheter (1702) and the external magnet (1700). This attractive force may be used to pull, push, or otherwise manipulate the catheter during advancement.

Once the first and/or second catheters have been advanced into the respective blood vessels, the catheters may be adjusted to affect the positioning of the catheters within the blood vessels and/or the positioning of the blood vessels relative to each other. In variations where a first catheter has been advanced into a first blood vessel and a second catheter has been advanced into a second blood vessel, the first and second catheters may be adjusted to bring at least a portion of the first and second catheters toward each other, which may act to bring blood vessels in closer approximation. In some variations, each of the first or second catheters may comprise one or more magnetic alignment elements, such as those described in more detail above. The magnetic alignment elements may result in an attractive force between the first and second catheters, which may pull the catheters toward each other. In some instances, this attractive force may be sufficient to compress tissue between the first and second catheters. For example, in variations where the first and second catheters comprise flat ablation surfaces, as described above, the attractive force may flatten and/or compress vessel tissue between the ablation surfaces. In other variations, the first and/or second catheter may comprise one or more shape-changing member, such as those described in relation to catheter (2500) in FIGS. 25A-25D, and the method comprises changing the shape of the first and/or second catheters using the shape-changing members. Changing the shape of the first and/or second catheters may help approximate the first and second blood vessels, as described above. Additionally, the shape change may also act to compress tissue between the first and second blood vessels, as mentioned above.

In some variations, adjusting the first and second catheters may comprise aligning the catheters axially and/or rotationally. For example, the catheters may be oriented such that a fistula-forming element of either the first or second catheter is positioned to form a fistula in a certain location. In variations where both the first and second catheters comprise fistula-forming elements (e.g., an active electrode and a ground electrode), the catheters may be oriented to align these fistula-forming elements. The catheters may be aligned in any suitable manner. In variations where the first and/or second catheters comprise one or more markers, such as those described above, the markers may be viewed (e.g., via fluoroscopy, x-ray, or the like) to ensure that the catheters have the proper axial and/or radial orientation relative to each other. Additionally, in variations where the first and/or second catheters comprise one or more magnetic alignment elements (e.g., one or more coupling magnets, as described in more detail above), the magnetic alignment elements may be used to axially and/or rotationally orient the first catheter relative to the second catheter.

Additionally, in some variations, one or more balloons or expandable members, such as those described above, may be used to help position the first and/or second catheters, or may act to hold the first and/or second catheters in place within the blood vessels. For example, in some variations, expansion of a balloon or expandable member of one of the catheters may engage the interior of a blood vessel, which may hold that catheter in place within the blood vessel. In other methods, the expansion of the balloon or expandable member can bias or otherwise press a fistula-forming element against blood vessel tissue, which may aid fistula formation.

Once the catheter or catheters have been positioned and adjusted, one or more fistula-forming elements may be used to create a fistula between the two blood vessels. For example, in some variations, one of the first and second catheters comprises a fistula-forming element (e.g., an electrode, a cutting blade, or the like), while the other catheter does not comprise a fistula-forming element. In other variations, both catheters comprise a fistula-forming element. In some of these variations, the fistula-forming elements of the first and second catheters act to form different fistulas. In other variations, the fistula-forming elements of the first and second catheters interact to form the same fistula. For example, in some variations the first and second catheters each comprises at least one electrode. In these methods, current may be supplied to the electrode or electrodes of one of the catheters, may be carried away by the electrode or electrodes of the other catheter, and may ablate or otherwise vaporize tissue as the current passes therethrough. Any suitable combination of electrodes as described above may be utilized to form the fistula. In other methods, such as those described above, formation of a fistula comprises puncturing or piercing a balloon of the first or second catheter, which may release one or more contrast solutions into the blood vessels. Additionally, in some variation, a balloon may be used to modify a fistula after the fistula has been formed.

Additionally, one or more balloons may be activated to affect the blood flow relative to the fistula. For example, in variations where an arterio-venous fistula is formed, it may be beneficial to dilate one or more portions of the artery and/or veins. Specifically, the portion of the artery upstream of an arterio-venous fistula may be expanded to increase flow through the fistula. Alternatively or additionally, a portion of a vein downstream from a fistula may be dilated to help increase flow through the fistula. In some variations, one or more portions expandable members may comprise an electrode for inducing necrosis or swelling in a portion of a blood vessel to decrease flow therethrough. For example, in some variations a portion of a vein upstream from a fistula may be at least partially occluded to minimize venous hypertension.

It should be appreciated that any of the catheters described above may be used to form a fistula using the methods above. For example, in some variations, a first catheter may be advanced into a first blood vessel, and the first catheter may comprise one or more fistula forming elements, such as those described in more details above. For example, in some variations, the first catheter may comprise one or more blades or other mechanical cutting elements. In some of these variations, the first catheter may comprise one or more of the blade mechanisms of catheters (2200), (3700), (3800) and/or (3900) described above in relation to FIGS. 22, 37, 38, and 39 respectively. In other variations, the first catheter may comprise one or more electrodes. The electrode may comprise one or more ablation surfaces, such as those described in more detail above. In some variations, the electrode may comprise a lead wire, wherein a portion of the lead wire acts as an ablation surface. For example, the first catheter may comprise one or more of the lead wire electrodes of catheters (2100), (3100), and/or (3200) described above in relation to FIGS. 21, 31 and 32, respectively. In still other variations, the first catheter may comprise one or more optical fibers or other members for delivering laser energy to blood vessel tissue. It should be appreciated that in some variations the first catheter may comprise a combination of two or more fistula forming elements. The fistula forming member of the first catheter may be activated or otherwise used to form a fistula between the first blood vessel and a second adjoining blood vessel.

In some variations, a second catheter may be placed in the second blood vessel. In some variations, the second catheter may comprise a fistula forming element (such as one or more of the fistula forming elements described in more detail above), but need not. In variations where the first catheter comprises one or more electrodes, second catheter may also comprise one or more electrodes. In some of these variations, current may be passed between the electrodes of the first catheter and the electrode of the second catheter during tissue ablation. In variations where the fistula forming element of the first catheter is configured to extend or otherwise move through blood vessel tissue during tissue fistula formation (e.g., a blade or other mechanical cutting device, one or more of the electrodes described above), the second catheter may comprise one or more sections or elements for contacting or otherwise receiving the fistula forming element of the first catheter as is passes through tissue. For example, in some variations, the second catheter may comprise one or more pockets or coated portions, such as those described above in relation to catheters (3300), (3400), (3500), and (3600) and FIGS. 33A-33B, 34, 35A-35B, and 36, respectively. In some of these variations, the pocket or coated portion may be configured to receive or otherwise contact an electrode of the first catheter as it passes through vessel tissue. In some variations, the electrode of the first catheter may be positioned such that it comes into contact with one or more electrodes of the second catheter. In some of these variations, the electrode may comprise one or more coated portions. In some of these variations, the coated portions may comprise a porous coating, such that current may pass through the porous coating between the electrodes, but direct physical contact between the two electrodes may be prevent. Additionally or alternatively, in some variations the second catheter may comprise one or more balloons (e.g., such as distal balloon (2604), central balloon (2606), and proximal balloon (2608) of catheter (2600) described above in relation to FIGS. 26A and 26B), such that advancement of a fistula forming element (e.g. an electrode, a mechanical cutting blade) may puncture or otherwise pierce one or more of the balloons. In some variations, this may release one or more fluids (e.g., a contrast solution) therefrom.

In some variations, it may be desirable to directionally form a fistula such that an opening is formed in a first blood vessel prior to formation of a second blood vessel. For example, in variations where a fistula is formed between an artery and a vein, it may be desirable to begin fistula formation in the vein. In these variations, an opening may be formed in a vein before an opening may be formed in the artery. If during fistula formulation one or more catheters malfunctions such that a complete fistula is not formed, this directional fistula formation may prevent the formation of an opening being formed in the artery without a corresponding opening being formed in the vein. When an opening is formed in an artery without completely forming a fistula, the arterial pressure may push blood into the extravascular space around the blood vessels, which in some instances may require a surgical procedure to fix. Conversely, formation of an opening in a vein without fully forming a fistula may result in some extravascular bleeding, but the venous pressure may be low enough such that significant bleeding does not occur, which may allow the blood vessel to heal itself. While described above as being used to directionally form a fistula from a vein to an artery, it should also be appreciated that in some instances it may be desirable to directionally form a fistula from an artery to a vein, from a first vein to a second vein, or from a first artery to a second artery. In still other variations, the catheters may be configured to form the fistula through the first and second blood vessels substantially simultaneously.

In order to directionally form a fistula from a first blood vessel (e.g., a vein) to a second blood vessel (e.g., an artery), a first catheter comprising a fistula forming element may be placed in the first blood vessel. The fistula forming element may be any suitable fistula forming elements as described in more detail above. In some variations, a second catheter may be placed in the second blood vessel. In variations where the fistula forming element comprises a blade or other mechanical cutting mechanism, the blade may activated to pierce, puncture, or otherwise through tissue of the first blood vessel. As the blade passes through tissue of the first blood vessel, it may also cut tissue of the second blood vessel. In variations where the first catheter comprises one or more electrodes, the electrodes may directionally form a fistula from the first blood vessel to the second blood vessel. In some variations, the electrode may be connected to a current generator (e.g., via the monopolar output of the current generator), and an ablation surface may be directed toward the second blood vessel. In some of these variations, a ground electrode may be placed external to the patient, and current may be applied to the tissue via the electrode of the first catheter. The tissue of the first blood vessel, being located closer to the electrode, may be ablated or vaporized more quickly than tissue of the second blood vessel. Additionally, in variations where the electrode is configured to extend through tissue, the electrode may first contact and ablate tissue of the first blood vessel prior to contacting and ablating tissue of the second blood vessel. Additionally, in some variations this directional fistula formation may form a larger opening in the first blood vessel than the opening formed in the second blood vessel. This may be useful in instances where the first blood vessel is a vein and the second blood vessel is an artery. Because a larger opening may provide less resistance to blood flow than a smaller opening, forming a larger opening in the vein may promote flow from the artery to the vein, which may reduce the likelihood the blood extravasates through fistula into the extravascular space.

As mentioned above, when a first catheter is placed in a first blood vessel and a second catheter is placed in a second catheter, first and second catheters may be aligned using one or more alignment elements. The first and second catheters may comprise any alignment elements or combination of alignment elements as described in more detail above. In some variations, the first and/or second catheters may comprise one or more coupling magnets proximal to a fistula forming element. Additionally or alternatively, the first and/or second catheters may comprise one or more coupling magnets distal to a fistula forming element. Additionally or alternatively, the first and/or second catheters may comprise one or more anchoring magnets proximal to a fistula forming element. Additionally or alternatively, the first and/or second catheters may comprise one or more anchoring magnets distal to a fistula forming element. When the first catheter is placed in a first blood vessel and the second catheter is placed in a second blood vessel, the alignment elements of the first and second catheters may interact to help bring the first and second blood vessels in closer approximation. In other instances, the alignment elements may be used to direct a fistula forming element (such as those describe above) of the first catheter toward tissue of the second vessel and/or one or more portions (e.g., a fistula forming element, a pocket, or the like) of the second catheter.

In some instances, it may be desirable to hold a first blood vessel in place relative to a second blood vessel. Accordingly, in some methods described here, at least a portion of a first blood vessel may be joined or fixed relative to at least a portion of a second blood vessel. In some variations, the first and second blood vessels may be joined prior to formation of the fistula. In other variations, a portion of a first blood vessel may be joined to a second blood vessel during fistula formation. In yet other variations, the first and second blood vessels may be joined following fistula formation. When a first blood vessel is joined to or fixed relative to a second blood vessel prior to fistula formation, this connection may help to minimize relative movement between the first and second blood vessels during fistula formation. Additionally, a connection between a first and second blood vessel may help prevent relative movement between the first and second blood vessels following fistula formation, which may reduce the likelihood that blood may extravasate out of fistula and into the extravascular space.

In methods where a first blood vessel is joined or otherwise fixed relative to a second blood vessel, the blood vessels may be joined in any suitable manner. In some variations, one or more catheters may be configured to deliver electrical, ultrasonic, or laser energy to the blood vessels to fuse a portion of a first blood vessel with a portion of a second blood vessel. In some instances, this application of energy may result in denaturization of proteins in the vessel walls, and the denatured proteins from each vessel wall may intertwine after application of the energy, which may act to fuse the blood vessels together.

Figure 40A:
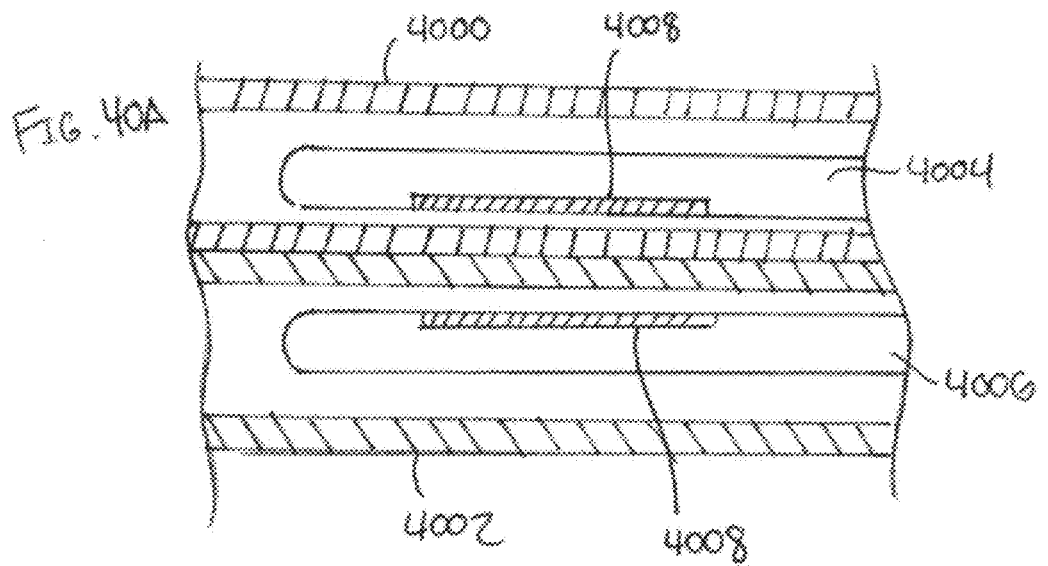
FIGS. 40A-40B, 41, and 42 depict variations of devices and methods for joining a first blood vessel to a second blood vessel.
Figure 40B:
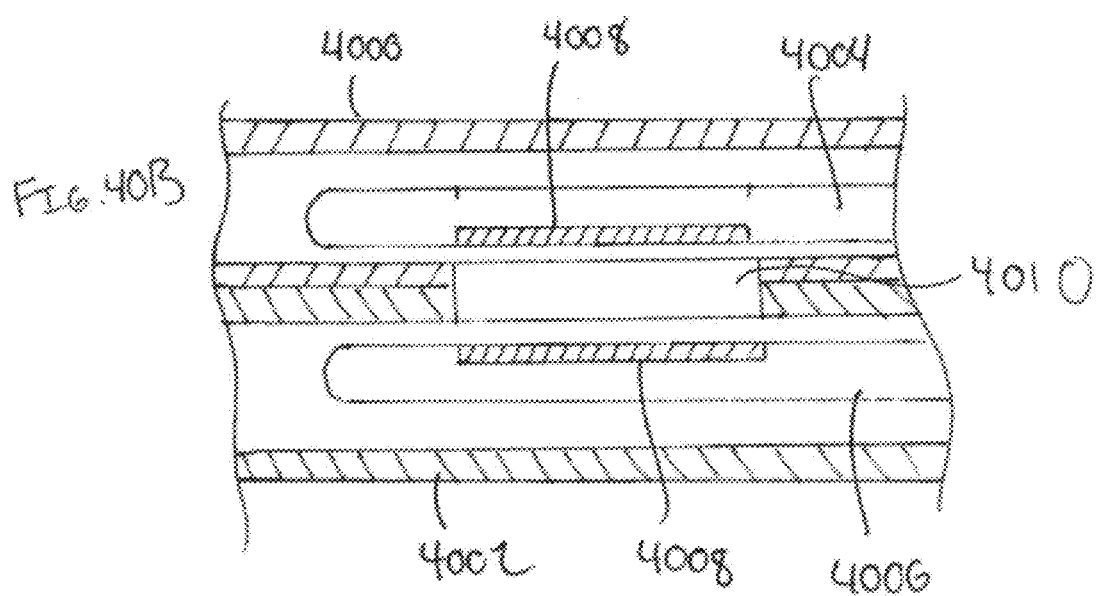

FIGS. 40A and 40B show one method by which a first blood vessel (4000) may be joined to a second blood vessel (4002). First blood vessel (4000) may be an artery or a vein, and second blood vessel (4002) may be an artery or a vein. As shown in FIG. 40A, a first catheter (4004) may be advanced into the first blood vessel (4000) and a second catheter (4006) may be advanced into the second blood vessel (4002). First (4004) and second (4006) catheters may each comprise electrodes (4008). In some variations, once advanced into the blood vessels, the first (4004) and second (4006) catheters may be manipulated to bring the first blood vessel (4000) in closer approximation to the second blood vessel (4002). In some variations, the first and second catheters one or more alignment elements (not shown), such as described in more detail above, may help to bring the blood vessels in closer approximation. Once positioned, energy may be delivered to the vessel tissue via one or more of the electrodes (4008), which may create a fused region (4010) of vessel tissue. Fused region (4010) may act to hold first blood vessel (4000) in place relative to the second blood vessel (4002). Electrodes (4008) may form a fused region (4010) of any suitable size or shape. In some variations, electrodes (4008) may be configured to form a rectangular fused region (4010). In other variations, electrodes may be configured to form a circular or oval fused region (4010).

In other variations, one or more biocompatible adhesives may be applied to a first blood vessel and a second blood vessel. In some variations, a needle or other delivery device may be introduced through the skin to a position near the first and second blood vessels, and may inject the adhesive to connect the first blood vessel and second blood. In these variations, a first catheter comprising one or more alignment elements may be placed in the first blood vessel, a second catheter comprising one or more alignment elements may be placed in the second blood vessel, and the alignment elements (e.g., one or more magnets and/or one or more shape-changing portions) may act to bring the first and second blood vessels in closer approximation, such that the adhesive bonds with the first and second blood vessels to hold them in an approximated position.

Figure 41:
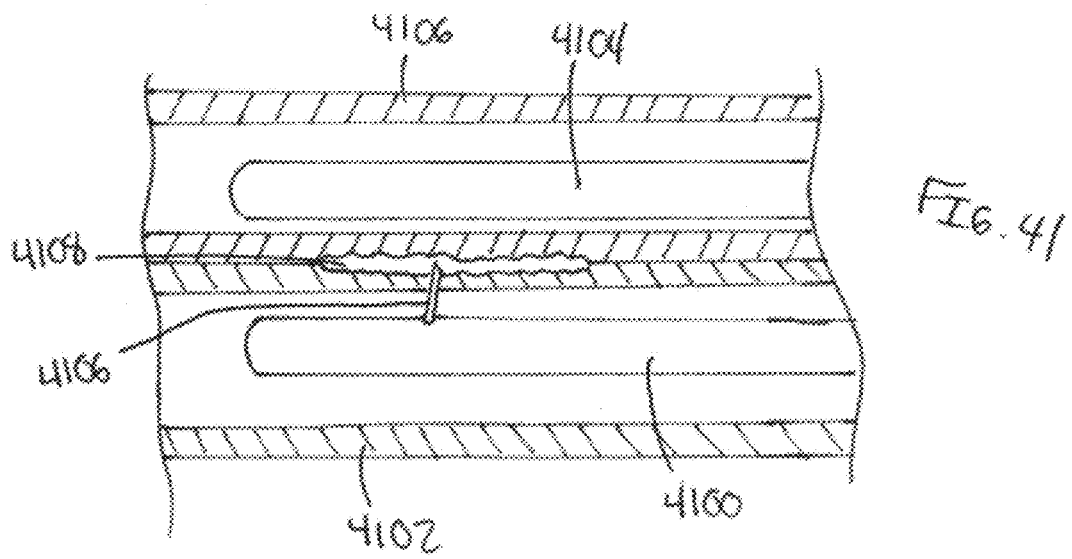

In other variations, a catheter placed in one of the blood vessels may be used to deliver one or more biocompatible adhesives. FIG. 41 shows one such method, in which a first catheter (4100) may be introduced into a first blood vessel (4102). In some variations, a second catheter (4104) may be introduced into a second blood vessel (4106). In these variations, first (4100) and second (4104) catheters may each comprise one or more alignment elements, which may act to bring the blood vessels in closer approximation as described in more detail above. First catheter (4100) may be comprise a needle (4106), which may be advanced from first catheter (4100) to puncture through tissue of the first blood vessel (4102). When a distal end of needle (4106) is advanced out of blood vessel (4102), an adhesive (4108) may be delivered out of needle (4106) between first (4102) and second (4106) blood vessels to join the blood vessels together.

Figure 42:
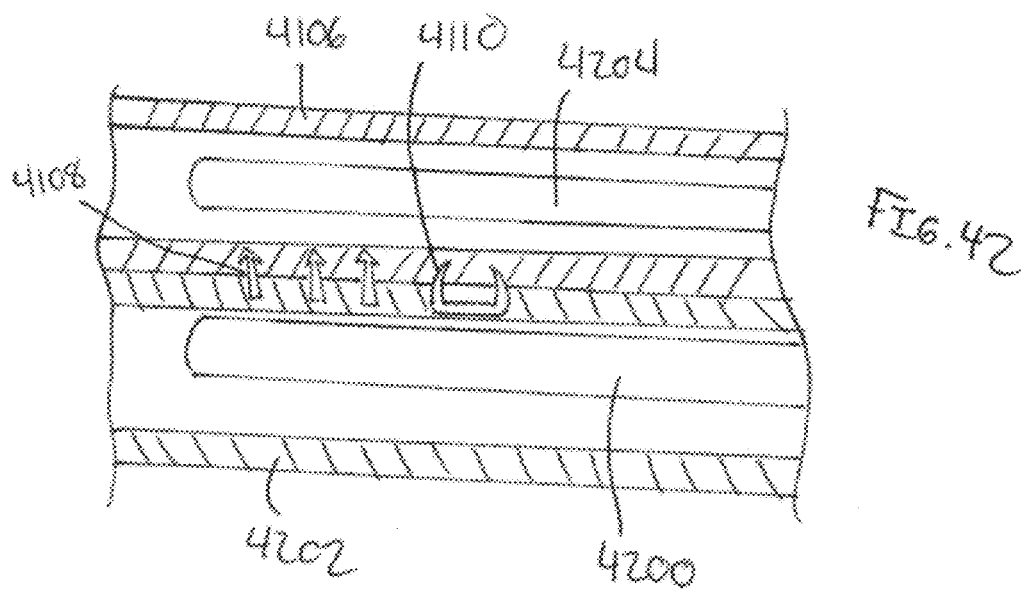

In still other variations, a catheter may deliver one or more barbs, staples, or other implants to connect a first blood vessel to a second blood vessel. FIG. 42 shows one such method, in which a first catheter (4200) may be introduced into a first blood vessel (4202). In some variations, a second catheter (4204) may be introduced into a second blood vessel (4206). In these variations, first (4200) and second (4204) catheters may each comprise one or more alignment elements, which may act to bring the blood vessels in closer approximation as described in more detail above. First catheter (4200) may be configured to deploy one or more barbs (4108), staples (4110), or other implants therefrom. The barbs (4108), staples (4110) or other implants may be delivered at least partially through tissue of the first blood vessel (4202) and at least partially through tissue of the second blood vessel (4206) and may act to hold the tissue of the first blood vessel (4202) in place relative to the tissue of the second blood vessel (4206). While shown in FIG. 42 as being used to deliver both barbs (4108) and staple (4110), catheter (4200) may be configured to deliver one or more barbs, one or more staples, one or more additional implants, or a combination thereof.

When one or more catheters are used to join or otherwise connect a first blood vessel to a second blood vessel, it should be appreciated that the one or more of the same catheters may also be used to form a fistula between the first and second blood vessels. In some variations, the same mechanism that is used to join the first and second blood vessels may also be used to form a fistula. For example, in variations where a catheter comprises an electrode, the same electrode may be used to both fuse vessel tissue (e.g., when a first power output is applied to electrode) and to create a fistula between the two blood vessels (e.g., when a second power output is applied to the electrode). In other variations, a catheter may comprise a first component for joining two blood vessels and a separate fistula forming element, such as those described in more detail above.

We claim:

1. A system for forming a fistula between two blood vessels comprising:
   a first catheter, comprising a catheter body, a lead wire and at least one alignment element, wherein the lead wire is moveable between a low-profile configuration and an extended position wherein at least a portion of the lead wire extends away from the catheter body, and wherein the lead wire is spring biased toward the extended position.

2. The system of claim 1 further comprising a second catheter.

3. The system of claim 2 wherein the second catheter comprises a recessed region.

4. The system of claim 3 wherein the recessed region is a pocket configured to receive at least a portion of the lead wire when the lead wire extends away from the catheter body of the first catheter.

5. The system of claim 4 wherein the second catheter comprises at least one alignment element, and wherein the at least one alignment element of the first catheter and the at least one alignment element of the second catheter are configured to align the first catheter and the second catheter such that the lead wire at least partially enters the pocket when the lead wire extends away from the catheter body of the first catheter.

6. The system of claim 4 wherein the pocket is formed in a nesting material housed at least partially within the catheter body of the second catheter.

7. The system of claim 4 wherein the pocket is formed in an electrode housed at least partially within the catheter body of the second catheter.

8. The system of claim 4 wherein the pocket is at least partially coated by an insulating material.

9. The system of claim 8 wherein the insulating material is porous.

10. The system of claim 1 wherein the lead wire comprises a first segment housed at least partially inside of the catheter body of the first catheter, a first angled segment extending from a distal end of the first segment, and a second angled segment extending from a distal end of the first angled segment.

11. The system of claim 10 wherein at least one insulating material covers the first segment and the first angled segment of the lead wire.

12. The system of claim 10 wherein at least one insulating material covers the first segment of the lead wire and partially covers the first angled segment of the lead wire.

13. A method of forming a fistula between a first blood vessel and a second blood vessel comprising:
 advancing a first catheter into the first blood vessel, wherein the first catheter comprises a catheter body, a lead wire and at least one alignment element, wherein the lead wire is moveable between a low-profile position and an extended position wherein at least a portion of the lead wire extends away from the catheter body, and wherein the lead wire is spring biased toward the extended position;
 advancing a second catheter into the second blood vessel, wherein the second catheter comprises at least one alignment element;
 positioning the first catheter and the second catheter such that the lead wire is aligned with the second catheter;
 moving the lead wire from a low-profile position to an extended position; and
 ablating tissue with the lead wire to form the fistula.

14. The method of claim 13 wherein the second catheter comprises a pocket, wherein positioning the first catheter and the second catheter comprises aligning the lead wire with the pocket.

15. The method of claim 13 wherein the second catheter comprises a balloon, and wherein ablating tissue with the lead wire comprises puncturing the balloon with the lead wire.

16. The method of claim 13 wherein the first blood vessel is a vein and the second blood vessel is an artery.

17. The method of claim 13 further comprising placing a ground electrode external to the first blood vessel and the second blood vessel, and wherein ablating tissue comprises passing current between the lead wire and the ground electrode.

18. The method of claim 13 wherein the lead wire comprises a first segment housed at least partially inside of the catheter body of the first catheter, a first angled segment extending from a distal end of the first segment, and a second angled segment extending from a distal end of the first angled segment.

19. The method of claim 18 wherein at least one insulating material covers the first segment and the first angled segment of the lead wire.

20. The method of claim 18 wherein at least one insulating material covers the first segment of the lead wire and partially covers the first angled segment of the lead wire.

21. The method of claim 13 wherein the first catheter comprises a shape-changing element, and further comprising repositioning the first blood vessel by changing the shape of the first catheter with the shape-changing element of the first catheter.

22. The method of claim 21 wherein the second catheter comprises a shape-changing element, and further comprising repositioning the second blood vessel by changing the shape of the second catheter with the shape-changing element of the second catheter.

23. The method of claim 22 wherein the second catheter comprises at least one expandable member, and wherein positioning the first and second catheters comprises expanding the at least one expandable member of the second catheter to hold the second catheter in place relative to the second blood vessel.

24. The method of claim 21 wherein the first catheter comprises at least one expandable member, and wherein positioning the first and second catheters comprises expanding the at least one expandable member of the first catheter to hold the first catheter in place relative to the first blood vessel.

* * * * *